(12) United States Patent
Lichter et al.

(10) Patent No.: US 8,852,626 B2
(45) Date of Patent: *Oct. 7, 2014

(54) CONTROLLED-RELEASE CNS MODULATING COMPOSITIONS AND METHODS FOR THE TREATMENT OF OTIC DISORDERS

(75) Inventors: Jay Lichter, Rancho Santa Fe, CA (US); Carl Lebel, Malibu, CA (US); Fabrice Piu, San Diego, CA (US); Qiang Ye, San Diego, CA (US); Luis A. Dellamary, San Marcos, CA (US); Andrew M. Trammel, Olathe, KS (US); Jeffrey P. Harris, La Jolla, CA (US)

(73) Assignees: Otonomy, Inc., San Diego, CA (US); The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/425,217

(22) Filed: Mar. 20, 2012

(65) Prior Publication Data
US 2012/0190671 A1 Jul. 26, 2012

Related U.S. Application Data

(63) Continuation of application No. 12/494,156, filed on Jun. 29, 2009, now abandoned.

(60) Provisional application No. 61/076,567, filed on Jun. 27, 2008, provisional application No. 61/082,450, filed on Jul. 21, 2008, provisional application No. 61/094,384, filed on Sep. 4, 2008, provisional application No. 61/101,112, filed on Sep. 29, 2008, provisional application No. 61/140,033, filed on Dec. 22, 2008, provisional application No. 61/164,812, filed on Mar. 30, 2009.

(51) Int. Cl.
| | |
|---|---|
| A61F 9/02 | (2006.01) |
| A61K 9/00 | (2006.01) |
| A61K 45/06 | (2006.01) |
| A61K 31/195 | (2006.01) |
| A61K 9/06 | (2006.01) |
| A61K 47/14 | (2006.01) |
| A61K 47/38 | (2006.01) |
| A61K 31/00 | (2006.01) |
| A61K 47/10 | (2006.01) |
| A61K 31/5513 | (2006.01) |
| A61K 31/167 | (2006.01) |
| A61K 47/44 | (2006.01) |

(52) U.S. Cl.
CPC .............. *A61K 31/00* (2013.01); *A61K 9/0046* (2013.01); *A61K 45/06* (2013.01); *A61K 31/195* (2013.01); *A61K 9/06* (2013.01); *A61K 47/14* (2013.01); *A61K 47/38* (2013.01); *A61K 47/10* (2013.01); *A61K 31/5513* (2013.01); *A61K 31/167* (2013.01); *A61K 47/44* (2013.01)

USPC .......... 424/437; 424/468; 424/469; 424/497; 604/514; 514/772.1

(58) Field of Classification Search
CPC .................................................. A61K 9/0046
See application file for complete search history.

(56) References Cited

U.S. PATENT DOCUMENTS

| | | |
|---|---|---|
| 4,478,822 A | 10/1984 | Haslam et al. |
| 5,292,516 A | 3/1994 | Viegas et al. |
| 5,503,848 A | 4/1996 | Perbellini et al. |
| 6,177,434 B1 | 1/2001 | Kopke et al. |
| 6,201,065 B1 | 3/2001 | Pathak et al. |
| 6,316,011 B1 | 11/2001 | Ron et al. |
| 6,392,036 B1 | 5/2002 | Karlsson et al. |
| 6,649,621 B2 | 11/2003 | Kopke et al. |
| 6,740,664 B2 | 5/2004 | Cagle et al. |
| 7,001,615 B1 | 2/2006 | Singh et al. |
| 7,524,834 B2 | 4/2009 | Karlsson et al. |
| 8,030,297 B2 | 10/2011 | Lichter et al. |
| 2002/0045668 A1 | 4/2002 | Dang et al. |
| 2003/0092776 A1 | 5/2003 | Ron et al. |
| 2003/0229333 A1 | 12/2003 | Ashton |
| 2004/0082509 A1 | 4/2004 | Bonny |
| 2004/0101560 A1 | 5/2004 | Sawchuk et al. |
| 2005/0147585 A1 | 7/2005 | Schwarz |
| 2005/0152982 A1 | 7/2005 | Appel et al. |
| 2005/0214338 A1 | 9/2005 | Guitton et al. |
| 2006/0013858 A1 | 1/2006 | Trune |
| 2006/0046970 A1 | 3/2006 | Bowman et al. |
| 2006/0063802 A1 | 3/2006 | Guitton et al. |

(Continued)

FOREIGN PATENT DOCUMENTS

| | | |
|---|---|---|
| WO | WO 97/38698 | 10/1997 |
| WO | WO 99/24051 | 5/1999 |

(Continued)

OTHER PUBLICATIONS

Ahn et al., "Lipoic acid rescues DBA mice from early-onset age-related hearing impairment," Neuroreport 19(13):1265-9, 2008.

Arnold et al., "Novel slow- and fast-type drug release round-window microimplants for local drug application to the cochlea: an experimental study in guinea pigs," Audiol Neurootol 10(1):53-63, 2005.

Auris Medical, press release reporting initiating of phase I/II clinical trial with AM-101, Feb. 22, 2007.

Auris Medical, press release reporting results of phase I/II clinical trial with AM-111, Jun. 21, 2006.

(Continued)

*Primary Examiner* — Hasan Ahmed
(74) *Attorney, Agent, or Firm* — Wilson, Sonsini, Goodrich & Rosati

(57) ABSTRACT

Disclosed herein are compositions and methods for the treatment of otic disorders with CNS modulating agent compositions and compositions administered locally to an individual afflicted with an otic disorder, through direct application of these compositions and compositions onto or via perfusion into the targeted auris structure(s).

9 Claims, 4 Drawing Sheets

(56) References Cited

U.S. PATENT DOCUMENTS

| | | |
|---|---|---|
| 2006/0205789 A1 | 9/2006 | Lobl et al. |
| 2006/0264897 A1 | 11/2006 | Lobl et al. |
| 2006/0269602 A1 | 11/2006 | Dasch et al. |
| 2007/0178051 A1 | 8/2007 | Pruitt et al. |
| 2008/0103118 A1 | 5/2008 | Clement et al. |
| 2009/0297533 A1 | 12/2009 | Lichter et al. |
| 2009/0306225 A1 | 12/2009 | Lichter et al. |
| 2009/0324552 A1 | 12/2009 | Lichter et al. |
| 2010/0004225 A1 | 1/2010 | Lichter et al. |
| 2010/0015228 A1 | 1/2010 | Lichter et al. |
| 2010/0015263 A1 | 1/2010 | Lichter et al. |
| 2010/0016218 A1 | 1/2010 | Lichter et al. |
| 2010/0016450 A1 | 1/2010 | Lichter et al. |
| 2010/0021416 A1 | 1/2010 | Lichter et al. |
| 2010/0022661 A1 | 1/2010 | Lichter et al. |
| 2010/0036000 A1 | 2/2010 | Lichter et al. |
| 2010/0197800 A1 | 8/2010 | Friedman et al. |
| 2011/0166060 A1 | 7/2011 | Simons et al. |

FOREIGN PATENT DOCUMENTS

| | | |
|---|---|---|
| WO | WO-99-32151 | 7/1999 |
| WO | WO 02/056890 A1 | 7/2002 |
| WO | WO 03/034979 | 5/2003 |
| WO | WO 03/017990 | 6/2003 |
| WO | WO 03/071986 | 9/2003 |
| WO | WO 2006/099325 | 9/2006 |
| WO | WO 2007/031098 | 3/2007 |
| WO | WO 2007/031280 | 3/2007 |
| WO | WO 2007/037874 | 4/2007 |
| WO | WO 2007/037886 | 4/2007 |
| WO | WO 2007/038949 | 4/2007 |
| WO | WO 2007/089490 | 8/2007 |
| WO | WO 2008/076556 | 6/2008 |

OTHER PUBLICATIONS

Battaglia et al., "Combination therapy (intratympanic dexamethasone + high-dose prednisone taper) for the treatment of idiopathic sudden sensorineural hearing loss," Otol Neurotol 29(4):453-60, 2008.

Campbell et al., "Oral-D-methionine (MRX-1024) significantly protects against cisplatin-induced hearing loss: a phase II study in humans," Abst $32^{nd}$ Ann MidWinter Res Meeting, ARO Abstracts 32:7, Feb. 14-19, 2009.

Chen and Nathans, "Estrogen-related receptor beta/NR3B2 controls epithelial cell fate and endolymph production by the stria vascularis," Dev Cell 13(3):325-37, 2007.

Chen et al., "Design and preparation of thermosensitive in situ gel of dexamethasone sodium phosphate," J Guangdong Coll Pharm 23(5):518-21, 2007 (English abstract).

Chen et al., "Evaluation of thermosensitive in situ gel using dynamic rheological experiment," Chin Pharm J 43(6):444-447, 2008 (English abstract).

Chen et al., "In vivo distribution and pharmacokinetics of dexamethasone sodium phosphate thermosensitive in situ gel following intratympanic injection," Sichuan Da Xue Xue Bao Yi Xue Ban 37(3):456-9, 2006 (English translation).

Chen et al., "Preparation and characterization of dexamethasone acetate-loaded solid lipid nanoparticles," Chinese J Pharm 39(4):261-264, 2008 (English abstract).

Chen et al., "Study on dexamethasone thermosensitive in situ gel for treating deafness," Chin Pharm J 41(9):685-688, 2006 (English abstract).

Ciprodex, product label, 2009.

Couloigner et al., The Laryngoscope, 1998, The American Laryngological, Rhinological, and Otological Society, vol. 108, pp. 592-598.

Deflorio et al., The Journal of Emergency Medicine, 2006, Elsevier, vol. 31, No. 4, pp. 377-379.

Derin et al., "The effects of L-carnitine on presbyacusis in the rat model," Clin Otolaryngol Allied Sci 29(3):238-41, 2004.

Dourmishev et al., "Waardenburg syndrome," Intl J Dermatol 39:656-663 (1999).

Endo et al., "Novel strategy for treatment of inner ears using a biodegradable gel," Laryngoscope 115(11):2016-20, 2005.

Feng et al., Zhonghua er Bi Yan Hou Tou Jing Wai Ke Za Zhi, Jun. 2007;42(6):443-6 (English Abstract).

Feng et al., Zhonghua Yi Xue Za Zhi, Aug. 28, 2007;87(32):2289-91 (English Abstract and Translation).

Fernandez et al., "Self-curing controlled release systems for steroids. Application of prednisolone-based polymeric systems to ear diseases," Biomaterials 26(16):3311-8, 2005.

Friedman et al., "GRM7 variants confer susceptibility to age-related hearing impairment," Hum Mol Genet 18(4):785-96, 2009.

Garduno-Anaya et al., "Dexamethasone inner ear perfusion by intratympanic injection in unilateral Ménière's disease: a two-year prospective, placebo-controlled, double-blind, randomized trial," Otolaryngol Head Neck Surg 133(2):285-94, 2005.

GB0823378.5 combined search and examination report dated Feb. 24, 2009.

GB0823378.5 Examination Report dated Oct. 23, 2009.

GB0907065.7 combined search and examination report dated Nov. 16, 2009.

GB0912650.9 combined search and examination report dated Oct. 23, 2009.

Gubbels et al., "Functional auditory hair cells produced in the mammalian cochlea by in utero gene transfer," Nature 455(7212):537-41, 2008.

Guyot et al., "Intratympanic application of an antiviral agent for the treatment of Ménière's disease," Orl J Otorhinolaryngol Relat Spec 70(1):21-6; discussion 26-7, 2008.

Hall et al., "Anti-Pneumocystis Activities of Aromatic Diamidoxine Prodrugs," Antimicrobial Agents & Chemotherapy, 1998, American Society for Microbiology 42(4):666-674 (1998).

Hargunani et al., "Intratympanic injection of dexamethasone: time course of inner ear distribution and conversion to its active form," Otol Neurotol 27(4):564-9, 2006.

Harris et al., "Prevention of noise-induced hearing loss with Src-PTK inhibitors," Hear Res 208(1-2):14-25, 2005.

Harris et al., "Treatment of corticosteroid-responsive autoimmune inner ear disease with methotrexate: a randomized controlled trial," JAMA 290(14):1875-83, 2003.

Hill et al., "Cisplatin-induced ototoxicity: effect of intratympanic dexamethasone injections," Otol Neurotol 29:1005-11, 2008.

Hoffer et al., "Transtympanic management of tinnitus," Otolaryngol Clin North Am 36(2):353-8, 2003.

Hori et al., Internal Medicine, Society for, 2003, vol. 42, No. 11, pp. 1153-1154.

Hoshino et al., "The non-steroidal anti-inflammatory drugs protect mouse cochlea against acoustic injury," Tohoku J Exp Med 216(1):53-9, 2008.

Inaoka et al., "Local application of hepatocyte growth factor using gelatin hydrogels attenuates noise-induced hearing loss in guinea pigs," Acta Otolaryngol 129(4):453-7, 2009.

Jia et al., "Intratympanic dexamethasone for refractory sudden deafness," Lin Chung Er Bi Yan Hou Tou Jing Wai Ke Za Zhi 22(7):309-11, 2008 (English translation).

Karolewicz and Pluta, "Thermosensitive polymers in drug form technology II. Possibilities of use of thermosensitive polymers as active substance carriers," Poimery W Medycinic 38(1):15-26, 2008 (English language abstract).

Kazama et al., "Lithium effectively complements vasopressin V2 receptor antagonist in the treatment of hyponatraemia of SIADH rats," Nephrol Dial Transplant 22(1):68-76, 2007.

Keithley et al., "GDNF protects the cochlea against noise damage," Neuroreport 9(10):2183-7, 1998.

Kim et al., "Effects of tumor necrosis factor alpha antagonist, platelet activating factor antagonist, and nitric oxide synthase inhibitor on experimental otitis media with effusion," Ann Otol Rhinol Laryngol 115(8):617-23, 2006.

Kitahara et al., "Up-regulation of cochlear aquaporin-3 mRNA expression after intra-endolymphatic sac application of dexamethasone," Neurol Res. 25(8):865-70, 2003.

(56) References Cited

OTHER PUBLICATIONS

Lamm and Arnold, "The effect of prednisolone and non-steroidal anti-inflammatory agents on the normal and noise-damaged guinea pig inner ear," Hear Res 115(1-2):149-61, 1998.
Lavreysen and Dautzenberg, "Therapeutic potential of group III metabotropic glutamate receptors," Curr Med Chem 15(7):671-84, 2008.
Lee et al., "Novel therapy for hearing loss: delivery of insulin-like growth factor 1 to the cochlea using gelatin hydrogel," Otol Neurotol 28(7):976-81, 2007.
Lee et al., "Regional delivery of vancomycin using pluronic F-127 to inhibit methicillin resistant Staphylococcus aureus (MRSA) growth in chronic otitis media in vitro and in vivo," J Control Release 96(1):1-7, 2004.
Liu et al., "Permeability of different Dexamethasone drugs through round window membrane," Zhonghua Er Bi Yan Hou Tou Jing Wai Ke Za Zhi 41(3):211-5, 2006 (English abstract).
McCarthy et al., "Alport syndrome: a review," Clinical Eye and Vision Care 12:139-150 (2000).
McGuinness and Shepherd, "Exogenous BDNF rescues rat spiral ganglion neurons in vivo," Otol Neurotol 26(5):1064-72, 2005.
Meltser et al., "Estrogen receptor beta protects against acoustic trauma in mice," J Clin Invest 118(4):1563-70, 2008.
Miceli et al., "Molecular pharmacology and therapeutic potential of neuronal Kv7-modulating drugs," Curr Opin Pharmacol 8(1):65-74, 2008.
Mitsukawa et al., "A selective metabotropic glutamate receptor 7 agonist: activation of receptor signaling via an allosteric site modulates stress parameters in vivo," Proc Natl Acad Sci U S A 102(51):18712-7, 2005.
Nakagawa and Ito, "Local drug delivery to inner ear for treatment of hearing loss," Curr Drug Ther 3:143-147, 2008.
Nance et al., "The Genetics of Deafness," Mental Retardation and Developmental Disabilities, 2003, Wiley-Liss, vol. 9, pp. 109-119.
Nishimaki et al., "Reduction of metabotropic glutamate receptor-mediated heterosynaptic inhibition of developing MNTB-LSO inhibitory synapses," Eur J Neurosci 26(2):323-30, 2007.
Nouvian et al., "Degeneration of sensory outer hair cells following pharmacological blockade of cochlear KCNQ channels in the adult guinea pig," Eur J Neurosci 17(12):2553-62, 2003.
Park et al., "Effect of inhibitor of tumor necrosis factor-alpha and oxatomide on immune mediated otitis media," Laryngoscope 116(9):1642-6, 2006.
Parnes et al., "Corticosteroid pharmacokinetics in the inner ear fluids: an animal study followed by clinical application," Laryngoscope 109(7 Pt 2 Supplement No. 91):1-17, 1999.
Paulson et al., "A novel controlled local drug delivery system for inner ear disease," Laryngoscope 118(4):706-11, 2008.
PCT/US2008/061330 International Search Report mailed Jul. 31, 2008.
PCT/US2009/048954 International Search Report mailed Mar. 12, 2010.
PCT/US2009/067552 international search report mailed Aug. 18, 2010.
Peng et al., "Clinical investigation of different routes of administration of dexamethasone on sudden deafness," Lin Chung Er Bi Yan Hou Tou Jing Wai Ke Za Zhi 22(10):442-5, 2008 (English translation).
Plontke et al., "Rapid clearance of methylprednisolone after intratympanic application in humans. Comment on: Bird PA, Begg EJ, Zhang M, et al. Intratympanic versus intravenous delivery of methylprednisolone to cochlear perilymph. Otol Neurotol 2007; 28:1124-30," Otol Neurotol 29(5):732-3, 2008.
Pondugula et al., "Glucocorticoid regulation of genes in the amiloride-sensitive sodium transport pathway by semicircular canal duct epithelium of neonatal rat," Physiol Genomics 24(2):114-23, 2006.
Pondugula et al., "Glucocorticoids stimulate cation absorption by semicircular canal duct epithelium via epithelial sodium channel," Am J Physiol Renal Physiol 286(6):F1127-35, 2004.

Psillas et al., "Potential efficacy of early treatment of acute acoustic trauma with steroids and piracetam after gunshot noise," Eur Arch Otorhinolaryngol 265(12):1465-9, 2008.
Puel, "Chemical synaptic transmission in the cochlea," Prog Neurobiol 47(6):449-76, 1995.
Sakata et al., International Tinnitus Journal, 2001, Tinnitus Center, vo. 7, issue 1, pp. 46-50.
Salt et al., "Local Inner Ear Drug Delivery and Pharmacokinetics," Drug Discovery Today 10(19):1299-1306 (2005).
Sanchez et al., Expert Opinion on Therapeutic Patents, 2000, Ashley Publications, vol. 10, issue 12, pp. 1911-1917.
Satoh et al., "Tumor necrosis factor-alpha, an initiator, and etanercept, an inhibitor of cochlear inflammation," Laryngoscope 112(9):1627-34, 2002.
Schoepp et al., "Pharmacological agents acting at subtypes of metabotropic glutamate receptors," Neuropharmacology 38(10):1431-76, 1999.
Seidman et al., "Anti-intercellular adhesion molecule-1 antibody's effect on noise damage," Laryngoscope 119(4):707-12, 2009.
She et al., "A short term study on the efficacies of intratympanic prednisolone and dexamethasone injection for subjective tinnitus," Lin Chung Er Bi Yan Hou Tou Jing Wai Ke Za Zhi 22(19):871-3, 2008 (English translation).
Shepherd et al., "Neurotrophins and electrical stimulation for protection and repair of spiral ganglion neurons following sensorineural hearing loss," Hear Res 242(1-2):100-9, 2008.
Shinohara et al., "Neurotrophic factor intervention restores auditory function in deafened animals," Proc Natl Acad Sci U S A 99(3):1657-60, 2002.
Sun et al., "In vitro permeability of round window membrane to transforming dexamethasone with delivery vehicles—a dosage estimation," Chin Med J (Engl) 120(24):2284-9, 2007.
Synphora AB, website printout for JB004/A, 2009.
Tabuchi et al., "Hearing impairment in TRPV4 knockout mice," Neurosci Lett 382(3):304-8, 2005.
Taguchi et al., "Expressions of aquaporin-2, vasopressin type 2 receptor, transient receptor potential channel vanilloid (TRPV)1, and TRPV4 in the human endolymphatic sac," Laryngoscope 117(4):695-8, 2007.
Tahera et al., "NF-kB mediated glucocorticoid response in the inner ear after acoustic trauma," J Neurosci Res 1;83(6):1066-76, 2006.
Takeda and Taguchi, "Aquaporins as potential drug targets for Meniere's disease and its related diseases," Handb Exp Pharmacol 190:171-84, 2009.
Takeda et al., "Decompression effects of erythritol on endolymphatic hydrops," Auris Nasus Larynx 36(2):146-51, 2009.
Takeda et al., "The effects of V2 antagonist (OPC-31260) on endolymphatic hydrops," Hear Res 182(1-2):9-18, 2003.
Takemura et al., "Direct inner ear infusion of dexamethasone attenuates noise-induced trauma in guinea pig," Hear Res 196(1-2):58-68, 2004.
Takumida and Anniko, "Nitric oxide in the inner ear,"Cur Opin Neurol 15(1):11-5, 2002.
Tang et al., "COUP-TFI controls Notch regulation of hair cell and support cell differentiation," Development 133(18):3683-93, 2006.
The Royal National Institute for Deaf People (RNID), advertisement in Nature 8(5):339-431, 2009.
Thorne et al., "Potential role of purinergic signalling in cochlear pathology," Audiol Neurootol 7(3):180-4, 2002.
Van Wijk et al., "Local perfusion of the tumor necrosis factor alpha blocker infliximab to the inner ear improves autoimmune neurosensory hearing loss," Audiol Neurootol 11(6):357-65, 2006.
Wang et al., "A novel dual inhibitor of calpains and lipid peroxidation (BN82270) rescues the cochlea from sound trauma," Neuropharmacology 52(6):1426-37, 2007.
Wang et al., "Over-expression of X-linked inhibitor of apoptosis protein slows presbycusis in C57BL/6J mice," Neurobiol Aging Aug 26, 2008 [Epub ahead of print].

(56) References Cited

OTHER PUBLICATIONS

Watanabe et al., "Inhibition of inducible nitric oxide synthase lowers the cochlear damage by lipopolysaccharide in guinea pigs," Free Radic Res 32(4):363-70, 2000.

Watanabe et al., "Nitric oxide synthase inhibitor reduces the apoptotic change in the cisplatin-treated cochlea of guinea pigs," Anticancer Drugs 11(9):731-5, 2000.

Watanabe et al., "Nitric oxide synthase inhibitor suppresses the ototoxic side effect of cisplatin in guinea pigs," Anticancer Drugs 11(5):401-6, 2000.

Yamamoto et al., "Inhibition of Notch/RBP-J signaling induces hair cell formation in neonate mouse cochleas," J Mol Med 84(1):37-45, 2006.

Yang et al., "Intratympanic immunosuppressives for prevention of immune-mediated sensorineural hearing loss," Am J Otol 21(4):499-504, 2000.

Yildirim et al., "Effect of intratympanic dexamethasone on noise-induced temporary threshold shift," Laryngoscope 115(7):1219-22, 2005.

Zheng et al., "Vanilloid receptors in hearing: altered cochlear sensitivity by vanilloids and expression of TRPV1 in the organ of corti," J Neurophysiol 90(1):444-55, 2003.

Zhou et al., "Intratympanic administration of methylprednisolone reduces impact of experimental intensive impulse noise trauma on hearing," Acta Oto-Laryngologica 129:602-607, 2009.

U.S. Appl. No. 12/466,310 Office Action mailed Jan. 12, 2011.
U.S. Appl. No. 12/504,553 Office Action dated Feb. 14, 2012.
U.S. Appl. No. 12/506,091 Office Action dated Feb. 22, 2012.

CONTROLLED-RELEASE CNS MODULATING COMPOSITIONS AND METHODS FOR THE TREATMENT OF OTIC DISORDERS

CROSS-REFERENCE

This application is a Continuation application of U.S. Ser. No. 12/494,156, filed 29 Jun. 2009, which claims the benefit of U.S. Provisional Application No. 61/076,567, filed 27 Jun. 2008; U.S. Provisional Application No. 61/082,450, filed 21 Jul. 2008; U.S. Provisional Application No. 61/094,384, filed 4 Sep. 2008; U.S. Provisional Application No. 61/101,112, filed 29 Sep. 2008; U.S. Provisional Application No. 61/140,033, filed 22 Dec. 2008; U.S. Provisional Application No. 61/164,812, filed 30 Mar. 2009; and UK Patent Application No. 0907070.7, filed Apr. 24, 2009; all of which are incorporated herein by reference in their entirety.

JOINT RESEARCH AGREEMENT

The claimed invention was made as a result of activities undertaken within the scope of a joint research agreement between Jay Benjamin Lichter, Benedikt K. Vollrath, Otonomy, Inc., and Avalon Ventures VIII GP, LLC that was in effect on or before the date the invention was made.

BACKGROUND OF THE INVENTION

Vertebrates have a pair of ears, placed symmetrically on opposite sides of the head. The ear serves as both the sense organ that detects sound and the organ that maintains balance and body position. The ear is generally divided into three portions: the outer ear, auris media (or middle ear) and the auris interna (or inner ear).

SUMMARY OF THE INVENTION

Described herein, in certain embodiments, are compositions, compositions, manufacturing methods, therapeutic methods, uses, kits, and delivery devices for the controlled-release of at least one CNS modulating agent to at least one structure or region of the ear. Disclosed herein, in certain embodiments, are controlled-release compositions for delivering a CNS modulating agent to the ear. In some embodiments, the target portion of the ear is the middle ear (or auris media). In some embodiments, the target portion of the ear is the inner ear (or auris interna). In other embodiments, the target portion of the ear is both the auris media and the auris interna. In some embodiments, the controlled-release compositions further comprise a rapid or immediate release component for delivering a CNS modulating agent to the targeted auris structure. All compositions comprise excipients that are auris-acceptable.

Also disclosed herein, in certain embodiments, are compositions and devices for the treatment of otic disorders, said compositions and devices comprising a CNS modulating agent. Further disclosed herein, in certain embodiments, are methods for the treatment of otic disorders by administration of a controlled-release composition comprising a CNS modulating agent to an individual in need thereof. In some embodiments, the otic disorder is endolymphatic hydrops, kinetosis, labyrinthitis, mal de debarquement, Meniere's disease, Meniere's syndrome, Ramsay Hunt's syndrome (Herpes zoster infection), recurrent vestibulopathy, tinnitus, vertigo, microvascular compression syndrome, utricular dysfunction, vestibular neuronitis, benign paroxysmal positional vertigo, or combinations thereof.

The auris compositions and therapeutic methods described herein have numerous advantages that overcome the previously-unrecognized limitations of compositions and therapeutic methods described in prior art.

Sterility

The environment of the inner ear is an isolated environment. The endolymph and the perilymph are static fluids and are not in contiguous contact with the circulatory system. The blood-labyrinth-barrier (BLB), which includes a blood-endolymph barrier and a blood-perilymph barrier, consists of tight junctions between specialized epithelial cells in the labyrinth spaces (i.e., the vestibular and cochlear spaces). The presence of the BLB limits delivery of active agents (e.g., CNS modulating agents, aural pressure modulators, antimicrobials) to the isolated microenvironment of the inner ear. Auris hair cells are bathed in endolymphatic or perilymphatic fluids and cochlear recycling of potassium ions is important for hair cell function. When the inner ear is infected, there is an influx of leukocytes and/or immunoglobulins (e.g. in response to a microbial infection) into the endolymph and/or the perilymph and the ionic composition of inner ear fluids is upset by the influx of leukocytes and/or immunoglobulins. In certain instances, a change in the ionic composition of inner ear fluids results in hearing loss, loss of balance and/or ossification of auditory structures. In certain instances, trace amounts of pyrogens and/or microbes trigger infections and related physiological changes in the isolated microenvironment of the inner ear.

Due to the susceptibility of the inner ear to infections, auris compositions require a level of sterility that has not been recognized hitherto in prior art. Provided herein are auris compositions that are sterilized with stringent sterility requirements and are suitable for administration to the middle and/or inner ear. In some embodiments, the auris compatible compositions described herein are substantially free of pyrogens and/or microbes.

Compatibility with Inner Ear Environment

Described herein are otic compositions with an ionic balance that is compatible with the perilymph and/or the endolymph and does not cause any change in cochlear potential. In specific embodiments, osmolarity/osmolality of the present compositions is adjusted, for example, by the use of appropriate salt concentrations (e.g., concentration of sodium salts) or the use of tonicity agents that render the compositions endolymph-compatible and/or perilymph-compatible (i.e. isotonic with the endolymph and/or perilymph). In some instances, the endolymph-compatible and/or perilymph-compatible compositions described herein cause minimal disturbance to the environment of the inner ear and cause minimum discomfort (e.g., vertigo) to a subject (e.g., a human) upon administration. Further, the compositions comprise polymers that are biodegradable and/or dispersible, and/or otherwise non-toxic to the inner ear environment. In some embodiments, the compositions described herein are free of preservatives and cause minimal disturbance (e.g., change in pH or osmolarity, irritation) in auditory structures. In some embodiments, the compositions described herein comprise antioxidants that are non-irritating and/or non-toxic to otic structures.

Dosing Frequency

The current standard of care for auris compositions requires multiple administrations of drops or injections (e.g. intratympanic injections) over several days (e.g., up to two weeks), including schedules of receiving multiple injections per day. In some embodiments, auris compositions described herein are controlled-release compositions and are administered at reduced dosing frequency compared to the current standard of care. In certain instances, when an auris composition is administered via intratympanic injection, a reduced frequency of administration alleviates discomfort caused by multiple intratympanic injections in individuals undergoing treatment for a middle and/or inner ear disease, disorder or condition. In certain instances, a reduced frequency of administration of intratympanic injections reduces the risk of permanent damage (e.g., perforation) to the tympanic membrane. The compositions described herein provide a constant, sustained, extended, delayed or pulsatile rate of release of an active agent into the inner ear environment and thus avoid any variability in drug exposure in treatment of otic disorders.

Therapeutic Index

Auris compositions described herein are administered into the ear canal, or in the vestibule of the ear. In some embodiments, access to the vestibular and cochlear apparatus occurs through the auris media (e.g., the round window membrane, the oval window/stapes footplate, the annular ligament and through the otic capsule/temporal bone). Otic administration of the compositions described herein avoids toxicity associated with systemic administration (e.g., hepatotoxicity, cardiotoxicity, gastrointestinal side effects, renal toxicity) of the active agents. In some instances, localized administration in the ear allows an active agent to reach a target (e.g., the inner ear) in the absence of systemic accumulation of the active agent. In some instances, local administration to the ear provides a higher therapeutic index for an active agent that would otherwise have dose-limiting systemic toxicity.

Prevention of Drainage into Eustachian Tube

In some instances, a disadvantage of liquid compositions is their propensity to drip into the eustachian tube and cause rapid clearance of the composition from the inner ear. Provided herein, in certain embodiments, are auris compositions comprising polymers that gel at body temperature and remain in contact with the target auditory surfaces (e.g., the round window) for extended periods of time. In some embodiments, the compositions further comprise a mucoadhesive that allows the compositions to adhere to otic mucosal surfaces. In some instances, the auris compositions described herein avoid attenuation of therapeutic benefit due to drainage or leakage of active agents via the eustachian tube.

DESCRIPTION OF CERTAIN EMBODIMENTS

Described herein, in certain embodiments, are controlled-release compositions and devices for treating otic disorders comprising a therapeutically-effective amount of a CNS modulating agent, a controlled-release auris-acceptable excipient and an auris-acceptable vehicle. In one aspect, the controlled-release auris-acceptable excipient is chosen from an auris-acceptable polymer, an auris-acceptable viscosity enhancing agent, an auris-acceptable gel, an auris-acceptable paint, an auris-acceptable foam, an auris-acceptable microsphere or microparticle, an auris-acceptable hydrogel, an auris-acceptable in situ forming spongy material, an auris-acceptable actinic radiation curable gel, an auris-acceptable liposome, an auris-acceptable nanocapsule or nanosphere, an auris-acceptable thermoreversible gel or combinations thereof. In further embodiments, the auris-acceptable viscosity enhancing agent is a cellulose, a cellulose ether, alginate, polyvinylpyrrolidone, a gum, a cellulosic polymer or combinations thereof. In yet another embodiment, the auris-acceptable viscosity enhancing agent is present in an amount sufficient to provide a viscosity of between about 1000 to about 1,000,000 centipoise. In still another aspect, the auris-acceptable viscosity enhancing agent is present in an amount sufficient to provide a viscosity of between about 50,000 to about 1,000,000 centipoise.

In some embodiments, the compositions disclosed herein are formulated for a pH that ensures that they are compatible with the targeted auris structure. In some embodiments, the compositions disclosed herein are formulated for a practical osmolality and/or osmolarity that ensures that homeostasis of the target auris structure is maintained. A perilymph-suitable osmolarity/osmolality is a practical osmolarity/osmolality that maintains the homeostasis of the target auris structure during administration of the pharmaceutical compositions described herein.

For example, the osmolarity of the perilymph is between about 270-300 mOsm/L and the compositions described herein are optionally formulated to provide a practical osmolarity of about 150 to about 1000 mOsm/L. In certain embodiments, the compositions described herein provide a practical osmolarity within about 150 to about 500 mOsm/L at the target site of action (e.g., the inner ear and/or the perilymph and/or the endolymph). In certain embodiments, the compositions described herein provide a practical osmolarity within about 200 to about 400 mOsm/L at the target site of action (e.g., the inner ear and/or the perilymph and/or the endolymph). In certain embodiments, the compositions described herein provide a practical osmolarity within about 250 to about 320 mOsm/L at the target site of action (e.g., the inner ear and/or the perilymph and/or the endolymph). In certain embodiments, the compositions described herein provide a perilymph-suitable osmolarity within about 150 to about 500 mOsm/L, about 200 to about 400 mOsm/L or about 250 to about 320 mOsm/L at the target site of action (e.g., the inner ear and/or the perilymph and/or the endolymph). In certain embodiments, the compositions described herein provide a perilymph-suitable osmolality within about 150 to about 500 mOsm/kg, about 200 to about 400 mOsm/kg or about 250 to about 320 mOsm/kg at the target site of action (e.g., the inner ear and/or the perilymph and/or the endolymph). Similarly, the pH of the perilymph is about 7.2-7.4, and the pH of the present compositions is formulated (e.g., with the use of buffers) to provide a perilymph-suitable pH of about 5.5 to about 9.0, about 6.0 to about 8.0 or about 7.0 to about 7.6. In certain embodiments, the pH of the compositions is within about 6.0 to about 7.6. In certain instances, the pH of the endolymph is about 7.2-7.9, and the pH of the present compositions is formulated (e.g., with the use of buffers) to be within about 5.5 to about 9.0, within about 6.5 to about 8.0 or within about 7.0 to about 7.6.

In some aspects, the controlled-release auris-acceptable excipient is biodegradable and/or bioeliminated (e.g., degraded and/or eliminated through urine, feces or other routes of elimination). In another aspect, the controlled-release composition further comprises an auris-acceptable mucoadhesive, an auris-acceptable penetration enhancer or an auris-acceptable bioadhesive.

In one aspect, the controlled-release composition is delivered using a drug delivery device, which is a needle and syringe, a pump, a microinjection device, and in situ forming spongy material or combinations thereof. In some embodiments, the CNS modulating agent of the controlled-release composition has limited or no systemic release, is toxic when administered systemically, has poor pK characteristics, or combinations thereof.

In some embodiments, the CNS modulating agent is a CNS inhibitory agent. In some embodiments, the CNS inhibitory agent inhibits the transmission of a nerve impulse. In some embodiments, the CNS inhibitory agent inhibits the release of a neurotransmitter. In some embodiments, the CNS inhibitory agent agonizes the activity of a GABA receptor. In some embodiments, the CNS inhibitory agent partially or fully inhibits the repolarization of a neuron. In some embodiments, the CNS inhibitory agent disrupts the conduction of an ion channel.

In some embodiments, the CNS modulating agent is an antihistamine, a GABA receptor modulator, a neurotransmitter reuptake inhibitor, a local anesthetic, an anticholinergic, a sodium channel blocker, a calcium channel blocker, a thyrotropin-releasing hormone, or combinations thereof. In another aspect, the CNS modulating agent is a salt or prodrug of the CNS modulating agent. In other aspects, the CNS modulating agent is meclizine, diphenhydramine, dimenhydrinate, loratadine, quetiapine, mepyramine, piperoxan, antazoline, carbinoxamine, doxylamine, clemastine, pheniramine, chlorphenamine, chlorpheniramine, dexchlorpheniramine, brompheniramine, triprolidine, cyclizine, chlorcyclizine, hydroxyzine, promethazine, alimemazine, trimeprazine, cyproheptadine, azatadine, ketotifen, oxatomide, meclizine hydrochloride, promethazine hydrochloride, cinnarizine, hydroxyzine pamoate, betahistine dihydrochloride, alprazolam, bromazepam, brotizolam, chlordiazepoxide, clonazepam, clorazepate, diazepam, estazolam, flunitrazepam, flurazepam, loprazolam, lorazepam, lormetazepam, idazolam, nimetazepam, nitrazepam, oxazepam, prazepam, temazepam, triazolam, clonazepam, diazepam, lorazepam, furosemide, bumetanide, ethacrynic acid, gabapentin, pregabalin, muscimol, baclofen, amitriptyline, nortriptyline, trimipramine, fluoxetine, paroxetine, sertraline, glycopyrrolate, homatropine, scopolamine, atropine, benzocaine, carticaine, cinchocaine, cyclomethycaine, lidocaine, prilocalne, propxycaine, proparacaine, tetracaine, tocamide, trimecaine, carbamazepine, oxcarbazepine, phenylein, valproic acid, sodium valproate, cinnarizine, flunarizine, nimodipine, thyrotropin-releasing hormone, or combinations thereof.

Also disclosed herein, in certain embodiments, is a method for treating an otic disorder comprising administering a composition disclosed herein at least once every 3, 4, 5, 6, 7, 8, 9, 10, 11, 12, 13, 14, or 15 days; at least once a week, once every two weeks, once every three weeks, once every four weeks, once every five weeks, or once every six weeks; or at least once a month, once every two months, once every three months, once every four months, once every five months, once every six months, once every seven months, once every eight months, once every nine months, once every ten months, once every eleven months, or once every twelve months. In particular embodiments, the controlled-release compositions described herein provide a sustained dose of a CNS modulating agent to the inner ear between subsequent doses of the controlled-release composition. That is, taking one example only, if new doses of the CNS modulating agent controlled-release composition are administered via intratympanic injection to the round window membrane every 10 days, then the controlled-release composition provides an effective dose of a CNS modulating agent to the inner ear (e.g., across the round window membrane) during that 10-day period.

In one aspect, the composition is administered so that the composition is in contact with the crista fenestrae cochleae, the round window membrane or the tympanic cavity. In one aspect the composition is administered by intratympanic injection.

Provided herein are pharmaceutical compositions or devices, comprising: a therapeutically effective amount of a CNS inhibitory agent having substantially low degradation products; and wherein the composition or device comprises two or more characteristics selected from:
(i) between about 0.1% to about 10% by weight of the CNS modulating agent, or pharmaceutically acceptable prodrug or salt thereof;
(ii) between about 14% to about 21% by weight of a polyoxyethylene-polyoxypropylene triblock copolymer of general formula E106 P70 E106;
(iii) sterile water, q.s., buffered to provide a pH between about 5.5 and about 8.0;
(iv) multiparticulate CNS modulating agent;
(v) a gelation temperature between about 19° C. to about 42° C.;
(vi) less than about 50 colony forming units (cfu) of microbiological agents per gram of composition, and
(vii) less than about 5 endotoxin units (EU) per kg of body weight of a subject.

In some embodiments, a pharmaceutical composition or device described herein comprises:
(i) between about 0.1% to about 10% by weight of the CNS modulating agent, or pharmaceutically acceptable prodrug or salt thereof;
(ii) between about 14% to about 21% by weight of a polyoxyethylene-polyoxypropylene triblock copolymer of general formula E106 P70 E106; and
(iii) multiparticulate CNS modulating agent.

In some embodiments, a pharmaceutical composition or device described herein comprises:
(i) between about 0.1% to about 10% by weight of the CNS modulating agent, or pharmaceutically acceptable prodrug or salt thereof;
(ii) between about 14% to about 21% by weight of a polyoxyethylene-polyoxypropylene triblock copolymer of general formula E106 P70 E106;
(iii) multiparticulate CNS modulating agent; and
(iv) a gelation temperature between about 19° C. to about 42° C.

In some embodiments, a pharmaceutical composition or device described above provides a practical osmolarity between about 150 and 500 mOsm/L. In some embodiments, a pharmaceutical composition or device described above provides a practical osmolarity between about 200 and 400 mOsm/L. In some embodiments, a pharmaceutical composition or device described above provides a practical osmolarity between about 250 and 320 mOsm/L.

In some embodiments, the CNS modulating agent is released from the pharmaceutical composition or device described above for a period of at least 3 days. In some embodiments, the CNS modulating agent is released from the pharmaceutical composition or device described above for a period of at least 5 days. In some embodiments, the CNS modulating agent is released from the pharmaceutical composition or device described above for a period of at least 10 days. In some embodiments, the CNS modulating agent is released from the pharmaceutical composition or device described above for a period of at least 14 days. In some embodiments, the CNS modulating agent is released from the pharmaceutical composition or device described above for a period of at least one month.

In some embodiments, a pharmaceutical composition or device described above comprises a CNS modulating agent as a neutral molecule, a free acid, a free base, a salt or a prodrug. In some embodiments, a pharmaceutical composition or device described above comprises a CNS modulating agent as a neutral molecule, a free acid, a free base, a salt or a prodrug, or a combination thereof.

In some embodiments, a pharmaceutical composition or device described above comprises a CNS modulating agent as multiparticulates. In some embodiments, a pharmaceutical composition or device described above comprises a CNS modulating agent in the form of micronized particles. In some embodiments, a pharmaceutical composition or device described above comprises a CNS modulating agent as micronized powders.

In some embodiments, a pharmaceutical composition or device described above comprises about 10% of a polyoxyethylene-polyoxypropylene triblock copolymer of general formula E106 P70 E106 by weight of the composition. In some embodiments, a pharmaceutical composition or device described above comprises about 15% of a polyoxyethylene-polyoxypropylene triblock copolymer of general formula E106 P70 E106 by weight of the composition. In some embodiments, a pharmaceutical composition or device described above comprises about 20% of a polyoxyethylene-polyoxypropylene triblock copolymer of general formula E106 P70 E106 by weight of the composition. In some embodiments, a pharmaceutical composition or device described above comprises about 25% of a polyoxyethylene-polyoxypropylene triblock copolymer of general formula E106 P70 E106 by weight of the composition.

In some embodiments, a pharmaceutical composition or device described herein comprises about 1% of a CNS modulating agent, or pharmaceutically acceptable prodrug or salt thereof, by weight of the composition. In some embodiments, a pharmaceutical composition or device described above comprises about 2% of a CNS modulating agent, or pharmaceutically acceptable prodrug or salt thereof, by weight of the composition. In some embodiments, a pharmaceutical composition or device described herein comprises about 3% of a CNS modulating agent, or pharmaceutically acceptable prodrug or salt thereof, by weight of the composition. In some embodiments, a pharmaceutical composition or device described herein comprises about 4% of a CNS modulating agent, or pharmaceutically acceptable prodrug or salt thereof, by weight of the composition. In some embodiments, a pharmaceutical composition or device described above comprises about 5% of a CNS modulating agent, or pharmaceutically acceptable prodrug or salt thereof, by weight of the composition. In some embodiments, a pharmaceutical composition or device described above comprises about 10% of a CNS modulating agent, or pharmaceutically acceptable prodrug or salt thereof, by weight of the composition. In some embodiments, a pharmaceutical composition or device described above comprises about 15% of a CNS modulating agent, or pharmaceutically acceptable prodrug or salt thereof, by weight of the composition. In some embodiments, a pharmaceutical composition or device described above comprises about 20% of a CNS modulating agent, or pharmaceutically acceptable prodrug or salt thereof, by weight of the composition. In some embodiments, a pharmaceutical composition or device described above comprises about 25% of a CNS modulating agent, or pharmaceutically acceptable prodrug or salt thereof, by weight of the composition. In some embodiments, a pharmaceutical composition or device described above comprises about 30% of a CNS modulating agent, or pharmaceutically acceptable prodrug or salt thereof, by weight of the composition. In some embodiments, a pharmaceutical composition or device described above comprises about 40% of a CNS modulating agent, or pharmaceutically acceptable prodrug or salt thereof, by weight of the composition. In some embodiments, a pharmaceutical composition or device described above comprises about 50% of a CNS modulating agent, or pharmaceutically acceptable prodrug or salt thereof, by weight of the composition. In some embodiments, a pharmaceutical composition or device described above comprises about 60% of a CNS modulating agent, or pharmaceutically acceptable prodrug or salt thereof, by weight of the composition. In some embodiments, a pharmaceutical composition or device described above comprises about 70% of a CNS modulating agent, or pharmaceutically acceptable prodrug or salt thereof, by weight of the composition. In some embodiments, a pharmaceutical composition or device described above comprises about 80% of a CNS modulating agent, or pharmaceutically acceptable prodrug or salt thereof, by weight of the composition. In some embodiments, a pharmaceutical composition or device described above comprises about 90% of a CNS modulating agent, or pharmaceutically acceptable prodrug or salt thereof, by weight of the composition.

In some embodiments, a pharmaceutical composition or device described above has a pH between about 5.5 and about 8.0. In some embodiments, a pharmaceutical composition or device described above has a pH between about 6.0 and about 8.0. In some embodiments, a pharmaceutical composition or device described above has a pH between about 6.0 and about 7.6.

In some embodiments, a pharmaceutical composition or device described above contains less than 100 colony forming units (cfu) of microbiological agents per gram of composition. In some embodiments, a pharmaceutical composition or device described above contains less than 50 colony forming units (cfu) of microbiological agents per gram of composition. In some embodiments, a pharmaceutical composition or device described above contains less than 10 colony forming units (cfu) of microbiological agents per gram of composition.

In some embodiments, a pharmaceutical composition or device described above contains less than 5 endotoxin units (EU) per kg of body weight of a subject. In some embodiments, a pharmaceutical composition or device described above contains less than 4 endotoxin units (EU) per kg of body weight of a subject.

In some embodiments, a pharmaceutical composition or device described above provides a gelation temperature between about between about 19° C. to about 42° C. In some embodiments, a pharmaceutical composition or device described above provides a gelation temperature between about between about 19° C. to about 37° C. In some embodiments, a pharmaceutical composition or device described above provides a gelation temperature between about between about 19° C. to about 30° C.

In some embodiments, the pharmaceutical composition or device is an auris-acceptable thermoreversible gel. In some embodiments, the polyoxyethylene-polyoxypropylene triblock copolymer is biodegradable and/or bioeliminated (e.g., the copolymer is eliminated from the body by a biodegradation process, e.g., elimination in the urine, the feces or the like). In some embodiments, a pharmaceutical composition or device described herein further comprises a mucoadhesive. In some embodiments, a pharmaceutical composition or device described herein further comprises a penetration enhancer. In some embodiments, a pharmaceutical composition or device described herein further comprises a thickening agent. In some embodiments, a pharmaceutical composition or device described herein further comprises a dye.

In some embodiments, a pharmaceutical composition or device described herein further comprises a drug delivery device selected from a needle and syringe, a pump, a microinjection device, a wick, an in situ forming spongy material or combinations thereof.

In some embodiments, a pharmaceutical composition or device described herein is a pharmaceutical composition or device wherein the CNS modulating agent, or pharmaceutically acceptable salt thereof, has limited or no systemic release, systemic toxicity, poor PK characteristics, or combinations thereof. In some embodiments, of the pharmaceutical compositions or devices described herein, the CNS modulating agent is in the form of a neutral molecule, a free base, a free acid, a salt, a prodrug, or a combination thereof. In some embodiments, of the pharmaceutical compositions or devices described herein, the CNS modulating agent is administered in the form of a phosphate or ester prodrug. In some embodiments, pharmaceutical compositions or devices described herein comprise one or more CNS modulating agent, or pharmaceutically acceptable salt thereof, prodrug or combination thereof as an immediate release agent.

In some embodiments, pharmaceutical compositions or devices described herein further comprise an additional therapeutic agent. In some embodiments, the additional therapeutic agent is a an acidifying agent, an anesthetic, an analgesic, an antibiotic, antiemetic, an antifungal, an antimicrobial agent, an antipsychotic (especially those in the phenothiazine class), an antiseptic, an antiviral, an astringent, a chemotherapeutic agent, a collagen, a corticosteroid, a diuretic, a keratolytic agent, a nitric oxide synthase inhibitor, combinations thereof.

In some embodiments, pharmaceutical compositions or devices described herein are pharmaceutical compositions or devices wherein the pH of the pharmaceutical composition or device is between about 6.0 to about 7.6.

In some embodiments, of the pharmaceutical compositions or devices described herein, the ratio of a polyoxyethylene-polyoxypropylene triblock copolymer of general formula E106 P70 E106 to a thickening agent is from about 40:1 to about 5:1. In some embodiments, the thickening agent is carboxymethyl cellulose, hydroxypropyl cellulose or hydroxypropyl methylcellulose.

In some embodiments, the otic disease or condition is endolymphatic hydrops, kinetosis, labyrinthitis, mal de debarquement, Meniere's disease, Meniere's syndrome, Ramsay Hunt's syndrome (Herpes zoster infection), recurrent vestibulopathy, tinnitus, vertigo, microvascular compression syndrome, utricular dysfunction, vestibular neuronitis, benign paroxysmal positional vertigo, or combinations thereof.

Also provided herein is a method of treating an otic disease or condition characterized by an excess of nerve impulses comprising administering to an individual in need thereof an intratympanic composition or device comprising a therapeutically effective amount of a CNS inhibitory agent, wherein the CNS inhibitory agent is in the form of a substantially low degradation product; and wherein the composition or device comprises two or more characteristics selected from:
  (i) between about 0.1% to about 10% by weight of the CNS modulating agent, or pharmaceutically acceptable prodrug or salt thereof;
  (ii) between about 14% to about 21% by weight of a polyoxyethylene-polyoxypropylene triblock copolymer of general formula E106 P70 E106;
  (iii) sterile water, q.s., buffered to provide a pH between about 5.5 and about 8.0;
  (iv) multiparticulate CNS modulating agent;
  (v) a gelation temperature between about 19° C. to about 42° C.;
  (vi) less than about 50 colony forming units (cfu) of microbiological agents per gram of composition, and
  (vii) less than about 5 endotoxin units (EU) per kg of body weight of a subject.

In some embodiments of the methods described herein, the CNS modulating agent is released from the composition or devices for a period of at least 3 days. In some embodiments of the methods described herein, the CNS modulating agent is released from the composition or device for a period of at least 4 days. In some embodiments of the methods described herein, the CNS modulating agent is released from the composition or device for a period of at least 5 days. In some embodiments of the methods described herein, the CNS modulating agent is released from the composition or device for a period of at least 6 days. In some embodiments of the methods described herein, the CNS modulating agent is released from the composition or device for a period of at least 7 days. In some embodiments of the methods described herein, the CNS modulating agent is released from the composition or device for a period of at least 8 days. In some embodiments of the methods described herein, the CNS modulating agent is released from the composition or device for a period of at least 9 days. In some embodiments of the methods described herein, the CNS modulating agent is released from the composition or device for a period of at least 10 days. In some embodiments of the method described above, the CNS modulating agent is essentially in the form of micronized particles.

In some embodiments of the methods described herein, the composition is administered across the round window. In some embodiments of the methods described herein, the otic disease or condition is endolymphatic hydrops, kinetosis, labyrinthitis, mal de debarquement, Meniere's disease, Meniere's syndrome, Ramsay Hunt's syndrome (Herpes zoster infection), recurrent vestibulopathy, tinnitus, vertigo, microvascular compression syndrome, utricular dysfunction, vestibular neuronitis, benign paroxysmal positional vertigo, or combinations thereof.

DETAILED DESCRIPTION OF THE INVENTION

Figure 1:
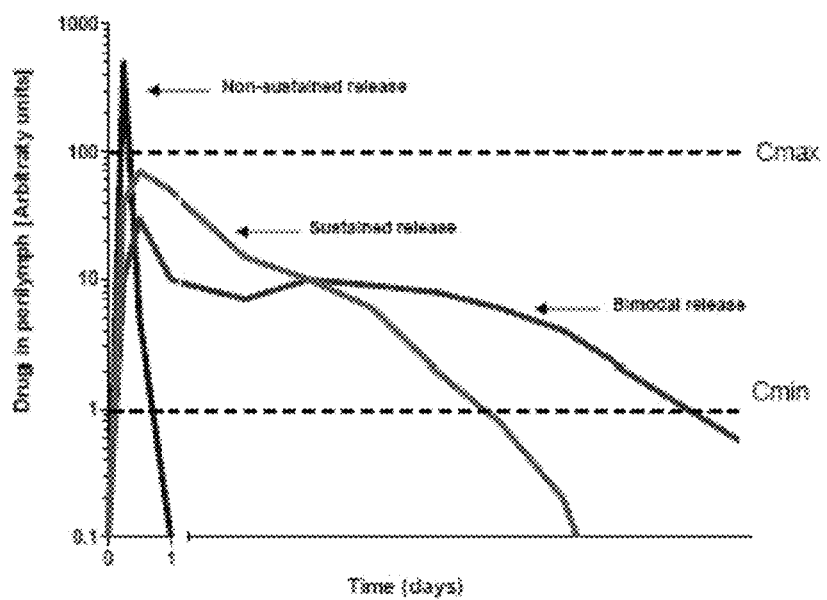
FIG. 1 illustrates a comparison of non-sustained release and sustained release compositions.
Figure 2:
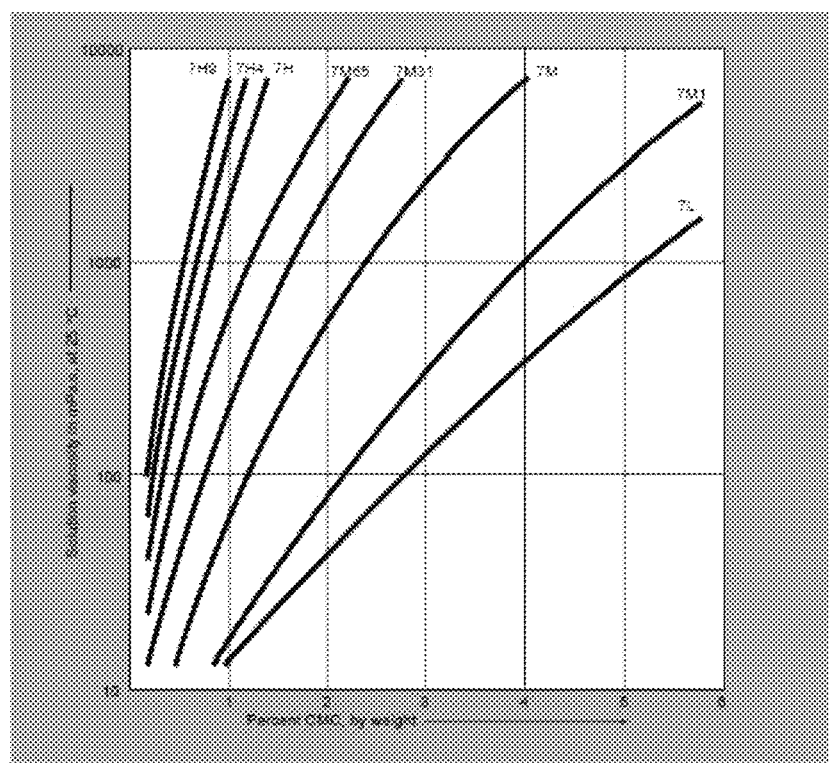
FIG. 2 illustrates the effect of concentration on the viscosity of aqueous solutions of Blanose refined CMC.
Figure 3:
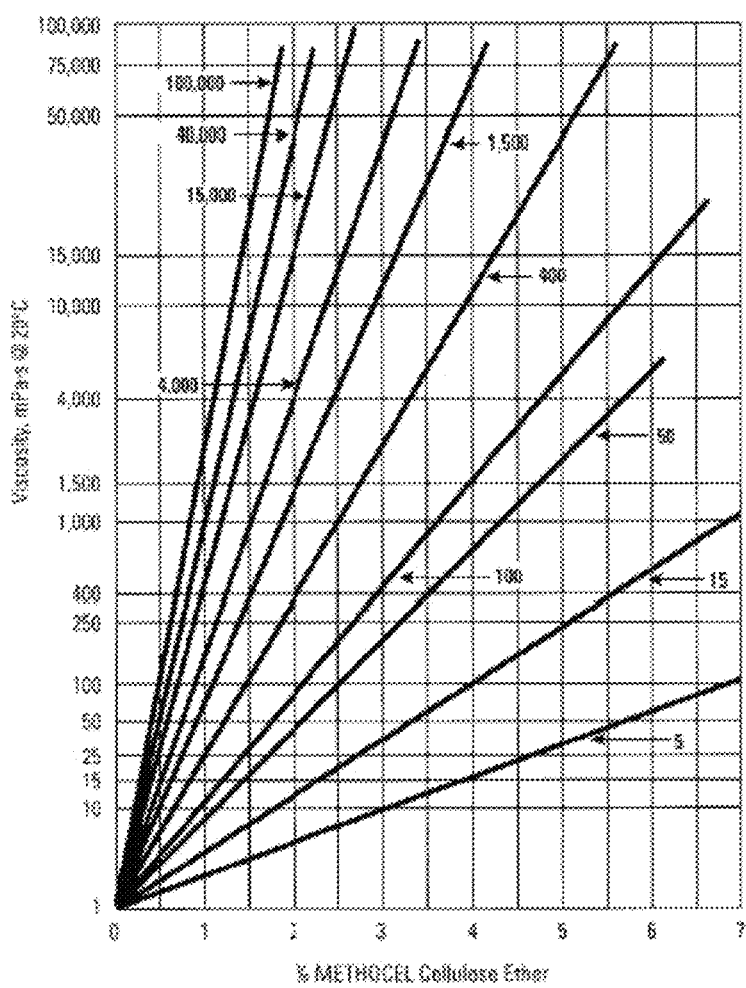
FIG. 3 illustrates the effect of concentration on the viscosity of aqueous solutions of Methocel.

Provided herein are controlled-release CNS modulating agent compositions and compositions to treat (e.g., ameliorate or reduce the effects of) an otic disease, disorder, or condition characterized by an excess of nerve impulses. In some embodiments, the CNS modulating agent is a CNS inhibitory agent. In some embodiments, the otic disease, disorder, or condition is endolymphatic hydrops, kinetosis, labyrinthitis, mal de debarquement, Meniere's disease, Meniere's syndrome, Ramsay Hunt's syndrome (Herpes zoster infection), recurrent vestibulopathy, tinnitus, vertigo, microvascular compression syndrome, utricular dysfunction, vestibular neuronitis, benign paroxysmal positional vertigo, or combinations thereof.

A few therapeutic products are available for the treatment of otic disorders; however, systemic routes via oral, intravenous or intramuscular routes are currently used to deliver these therapeutic agents. In some instances, systemic drug administration creates a potential inequality in drug concentration with higher circulating levels in the serum, and lower levels in the target auris media and auris interna organ structures. As a result, fairly large amounts of drug are required to overcome this inequality in order to deliver sufficient, therapeutically effective quantities to the inner ear. In addition, systemic drug administration may increase the likelihood of systemic toxicities and adverse side effects as a result of the high serum amounts required to effectuate sufficient local delivery to the target site. Systemic toxicities may also occur as a result of liver breakdown and processing of the therapeutic agents, forming toxic metabolites that effectively erase any benefit attained from the administered therapeutic.

To overcome the toxic and attendant side effects of systemic delivery, disclosed herein are methods and compositions and devices for local delivery of therapeutic agents to targeted auris structures. Access to, for example, the vestibular and cochlear apparatus will occur through the auris media including round window membrane, the oval window/stapes footplate, the annular ligament and through the otic capsule/temporal bone.

Intratympanic injection of therapeutic agents is the technique of injecting a therapeutic agent behind the tympanic membrane into the auris media and/or auris interna. This technique presents several challenges; for example, access to the round window membrane, the site of drug absorption into the auris interna, is challenging.

Further, intra-tympanic injections create several unrecognized problems not addressed by currently available treatment regimens, such as changing the osmolarity and pH of the perilymph and endolymph, and introducing pathogens and endotoxins that directly or indirectly damage inner ear structures. One of the reasons the art may not have recognized these problems is that there are no approved intra-tympanic compositions: the inner ear provides sui generis composition challenges. Thus, compositions developed for other parts of the body have little to no relevance for an intra-tympanic composition.

There is no guidance in the prior art regarding requirements (e.g., level of sterility, pH, osmolarity) for otic compositions that are suitable for administration to humans. There is wide anatomical disparity between the ears of animals across species. A consequence of the inter-species differences in auditory structures is that animal models of inner ear disease are often unreliable as a tool for testing therapeutics that are being developed for clinical approval.

Provided herein are otic compositions that meet stringent criteria for pH, osmolarity, ionic balance, sterility, endotoxin and/or pyrogen levels. The auris compositions described herein are compatible with the microenvironment of the inner ear (e.g., the perilymph) and are suitable for administration to humans. In some embodiments, the compositions described herein comprise dyes and aid visualization of the administered compositions obviating the need for invasive procedures (e.g., removal of perilymph) during preclinical and/or clinical development of intratympanic therapeutics.

Provided herein are controlled-release CNS modulating agent compositions and compositions to locally treat targeted auris structures, thereby avoiding side effects as a result of systemic administration of the CNS modulating agent compositions and compositions. The locally applied CNS modulating agent compositions and compositions and devices are compatible with the targeted auris structures, and administered either directly to the desired targeted auris structure (e.g., the cochlear region, the tympanic cavity or the external ear), or administered to a structure in direct communication with areas of the auris interna (e.g., the round window membrane, the crista fenestrae cochleae or the oval window membrane). By specifically targeting an auris structure, adverse side effects as a result of systemic treatment are avoided. Moreover, clinical studies have shown the benefit of having long term exposure of drug to the perilymph of the cochlea, for example with improved clinical efficacy of sudden hearing loss when the therapeutic agent is given on multiple occasions. Thus, by providing a controlled-release CNS modulating composition or composition to treat otic disorders, a constant, variable and/or extended source of a CNS modulating agent is provided to the subject suffering from an otic disorder, reducing or eliminating uncertainty in treatment. Accordingly, one embodiment disclosed herein is to provide a composition that enables at least one CNS modulating agent to be released in therapeutically effective doses either at variable or constant rates such as to ensure a continuous release of a CNS modulating agent. In some embodiments, a CNS modulating agent disclosed herein is administered as an immediate release composition or composition. In other embodiments, a CNS modulating agent is administered as a sustained release composition, released either continuously, variably or in a pulsatile manner, or variants thereof. In still other embodiments, a CNS modulating agent composition is administered as both an immediate release and sustained release composition, released either continuously, variably or in a pulsatile manner, or variants thereof. The release is optionally dependent on environmental or physiological conditions, for example, the external ionic environment (see, e.g. Oros® release system, Johnson & Johnson).

In addition, localized treatment of the targeted auris structure also affords the use of previously undesired therapeutic agents, including agents with poor pK profiles, poor uptake, low systemic release and/or toxicity issues. Because of the localized targeting of the CNS modulating agent compositions and compositions and devices, as well as the biological blood barrier present in the auris interna, the risk of adverse effects will be reduced as a result of treatment with previously characterized toxic or ineffective CNS modulating agents. Accordingly, also contemplated within the scope of the embodiments herein is the use of a CNS modulating agents in the treatment of disorders that have been previously rejected by practitioners because of adverse effects or ineffectiveness of the CNS modulating agent.

Also included within the embodiments disclosed herein is the use of additional auris-compatible agents in combination with the CNS modulating agent compositions and compositions and devices disclosed herein. When used, such agents assist in the treatment of hearing or equilibrium loss or dysfunction as a result of endolymphatic hydrops, kinetosis, labyrinthitis, mal de debarquement, Meniere's disease, Meniere's syndrome, Ramsay Hunt's syndrome (Herpes zoster infection), recurrent vestibulopathy, tinnitus, vertigo, microvascular compression syndrome, utricular dysfunction, vestibular neuronitis, benign paroxysmal positional vertigo, or combinations thereof. Accordingly, additional agents that ameliorate or reduce the effects of endolymphatic hydrops, kinetosis, labyrinthitis, mal de debarquement, Meniere's disease, Meniere's syndrome, Ramsay Hunt's syndrome (Herpes zoster infection), recurrent vestibulopathy, tinnitus, vertigo, microvascular compression syndrome, utricular dysfunction, vestibular neuronitis, benign paroxysmal positional vertigo, or combinations thereof are also contemplated to be used in combination with a CNS modulating agent. In some embodiments, the additional agent is an acidifying agent, an anesthetic, an analgesic, an antibiotic, antiemetic, an antifungal, an anti-microbial agent, an antipsychotic (especially those in the phenothiazine class), an antiseptic, an antiviral, an astringent, a chemotherapeutic agent, a collagen, a corticosteroid, a diuretic, a keratolytic agent, a nitric oxide synthase inhibitor, or combinations thereof.

In some embodiments, an auris-acceptable controlled-release CNS modulating composition described herein is administered to the target ear region and an oral dose of a CNS modulating agent is additionally administered. In some embodiments, an oral dose of a CNS modulating agent is administered before administration of the auris-acceptable controlled-release CNS modulating composition, and then the oral dose is tapered off over the period of time that the controlled-release CNS modulating composition is provided. Alternatively, an oral dose of a CNS modulating agent is administered during administration of the controlled-release CNS modulating composition, and then the oral dose is tapered off over the period of time that the controlled-release CNS modulating composition is provided. Alternatively, an oral dose of a CNS modulating agent is administered after administration of the controlled-release CNS modulating composition, and then the oral dose is tapered off over the period of time that the controlled-release CNS modulating composition is provided.

In addition, the CNS modulating agent pharmaceutical compositions or compositions or devices included herein also include carriers, adjuvants (e.g., preserving, stabilizing, wetting or emulsifying agents), solution promoters, salts for regulating the osmotic pressure, and/or buffers. Such carriers, adjuvants, and other excipients will be compatible with the environment in the targeted auris structure(s). Specifically contemplated are carriers, adjuvants and excipients that lack ototoxicity or are minimally ototoxic in order to allow effective treatment of the otic disorders contemplated herein with minimal side effects in the targeted regions or areas. To prevent ototoxicity, CNS modulating agent pharmaceutical compositions or compositions or devices disclosed herein are optionally targeted to distinct regions of the targeted auris structures, including but not limited to the tympanic cavity, vestibular bony and membranous labyrinths, cochlear bony and membranous labyrinths and other anatomical or physiological structures located within the auris interna.

CERTAIN DEFINITIONS

The term "auris-acceptable" with respect to a composition, composition or ingredient, as used herein, includes having no persistent detrimental effect on the auris media (or middle ear) and the auris interna (or inner ear) of the subject being treated. By "auris-pharmaceutically acceptable," as used herein, refers to a material, such as a carrier or diluent, which does not abrogate the biological activity or properties of the compound in reference to the auris media (or middle ear) and the auris interna (or inner ear), and is relatively or is reduced in toxicity to the auris media (or middle ear) and the auris interna (or inner ear), i.e., the material is administered to an individual without causing undesirable biological effects or interacting in a deleterious manner with any of the components of the composition in that it is contained.

As used herein, amelioration or lessening of the symptoms of a particular otic disease, disorder or condition by administration of a particular compound or pharmaceutical composition refers to any decrease of severity, delay in onset, slowing of progression, or shortening of duration, whether permanent or temporary, lasting or transient that is attributed to or associated with administration of the compound or composition.

"Antioxidants" are auris-pharmaceutically acceptable antioxidants, and include, for example, butylated hydroxy-toluene (BHT), sodium ascorbate, ascorbic acid, sodium metabisulfite and tocopherol. In certain embodiments, antioxidants enhance chemical stability where required. Antioxidants are also used to counteract the ototoxic effects of certain therapeutic agents, including agents that are used in combination with the CNS modulating agents disclosed herein.

"Auris interna" refers to the inner ear, including the cochlea and the vestibular labyrinth, and the round window that connects the cochlea with the middle ear.

"Auris-bioavailability" or "Auris-interna bioavailability" or "Auris-media bioavailability" or "Auris-externa bioavailability" refers to the percentage of the administered dose of compounds disclosed herein that becomes available in the targeted auris structure of the animal or human being studied.

"Auris media" refers to the middle ear, including the tympanic cavity, auditory ossicles and oval window, which connects the middle ear with the inner ear.

"Auris externa" refers to the outer ear, including the pinna, the auditory canal, and the tympanic membrane, which connects the outer ear with the middle ear.

"Balance disorder" refers to a disorder, illness, or condition that causes a subject to feel unsteady, or to have a sensation of movement. Included in this definition are dizziness, vertigo, disequilibrium, and pre-syncope. Diseases that are classified as balance disorders include, but are not limited to, Ramsay Hunt's Syndrome, Meniere's Disease, mal de debarquement, benign paroxysmal positional vertigo, and labyrinthitis.

"Blood plasma concentration" refers to the concentration of compounds provided herein in the plasma component of blood of a subject.

"Carrier materials" are excipients that are compatible with CNS modulating agent(s), the targeted auris structure(s) and the release profile properties of the auris-acceptable pharmaceutical compositions. Such carrier materials include, e.g., binders, suspending agents, disintegration agents, filling agents, surfactants, solubilizers, stabilizers, lubricants, wetting agents, diluents, and the like. "Auris-pharmaceutically compatible carrier materials" include, but are not limited to, acacia, gelatin, colloidal silicon dioxide, calcium glycerophosphate, calcium lactate, maltodextrin, glycerine, magnesium silicate, polyvinylpyrrolidone (PVP), cholesterol, cholesterol esters, sodium caseinate, soy lecithin, taurocholic acid, phosphatidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like.

"CNS modulator" and "CNS modulating agent" are synonyms. They refer to agents that decrease, diminish, partially suppress, fully suppress, ameliorate, antagonize, agonize, stimulate or increase the activity of the CNS. For example, they may increase the activity of GABA by, for example, increasing the sensitivity of the GABA receptors, or they may alter the depolarization in neurons.

The term "diluent" refers to chemical compounds that are used to dilute the CNS modulating agent prior to delivery and that are compatible with the targeted auris structure(s).

"Dispersing agents," and/or "viscosity modulating agents" are materials that control the diffusion and homogeneity of the CNS modulating agent through liquid media. Examples of diffusion facilitators/dispersing agents include but are not limited to hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronic F127, Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol has a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose are also be used as dispersing agents. Optional dispersing agents useful in liposomal dispersions and self-emulsifying dispersions of the CNS modulating agents disclosed herein are dimyristoyl phosphatidyl choline, phosphatidyl cholines (c8-c18), phosphatidylethanolamines (c8-c18), phosphatidyl glycerols (c8-c18), natural phosphatidyl choline from eggs or soy, natural phosphatidyl glycerol from eggs or soy, cholesterol and isopropyl myristate.

"Drug absorption" or "absorption" refers to the process of movement of the CNS modulating agent(s) from the localized site of administration, by way of example only, the round window membrane of the inner ear, and across a barrier (the round window membranes, as described below) into the auris interna or inner ear structures. The terms "co-administration" or the like, as used herein, are meant to encompass administration of the CNS modulating agents to a single patient, and are intended to include treatment regimens in that the CNS modulating agents are administered by the same or different route of administration or at the same or different time.

The terms "effective amount" or "therapeutically effective amount," as used herein, refer to a sufficient amount of the CNS modulating agents being administered that would be expected to relieve to some extent one or more of the symptoms of the disease or condition being treated. For example, the result of administration of the CNS modulating agents, disclosed herein is reduction and/or alleviation of the signs, symptoms, or causes of Meniere's disease. For example, an "effective amount" for therapeutic uses is the amount of the CNS modulating agent, including a composition as disclosed herein required to provide a decrease or amelioration in disease symptoms without undue adverse side effects. The term "therapeutically effective amount" includes, for example, a prophylactically effective amount. An "effective amount" of a CNS modulating agent composition disclosed herein is an amount effective to achieve a desired pharmacologic effect or therapeutic improvement without undue adverse side effects. It is understood that "an effective amount" or "a therapeutically effective amount" varies, in some embodiments, from subject to subject, due to variation in metabolism of the compound administered, age, weight, general condition of the subject, the condition being treated, the severity of the condition being treated, and the judgment of the prescribing physician. It is also understood that "an effective amount" in an extended-release dosing format may differ from "an effective amount" in an immediate-release dosing format based upon pharmacokinetic and pharmacodynamic considerations.

The terms "enhance" or "enhancing" refers to an increase or prolongation of either the potency or duration of a desired effect of the CNS modulating agent, or a diminution of any adverse symptoms such as localized pain that is consequent upon administration of the therapeutic agent. Thus, in regard to enhancing the effect of the CNS modulating agents disclosed herein, the term "enhancing" refers to the ability to increase or prolong, either in potency or duration, the effect of other therapeutic agents that are used in combination with the CNS modulating agents disclosed herein. An "enhancing-effective amount," as used herein, refers to an amount of a CNS modulating agents, or other therapeutic agent, which is adequate to enhance the effect of another therapeutic agent or CNS modulating agents in a desired system. When used in a patient, amounts effective for this use will depend on the severity and course of the disease, disorder or condition, previous therapy, the patient's health status and response to the drugs, and the judgment of the treating physician.

The term "inhibiting" includes preventing, slowing, or reversing the development of a condition, for example, Meniere's disease, or advancement of a condition in a patient necessitating treatment.

The terms "kit" and "article of manufacture" are used as synonyms.

"Modulator of the $GABA_A$ receptor," "modulator of the GABA receptor," "$GABA_A$ receptor modulator," and "GABA receptor modulator," are synonyms. They refer to substances that modulate the activity of the GABA neurotransmitter, by, for example, increasing the sensitivity of the GABA receptor to GABA. "Pharmacodynamics" refers to the factors that determine the biologic response observed relative to the concentration of drug at the desired site within the targeted auris structure.

"Pharmacokinetics" refers to the factors that determine the attainment and maintenance of the appropriate concentration of drug at the desired site within the targeted auris structure.

In prophylactic applications, compositions containing the CNS modulators described herein are administered to a patient susceptible to or otherwise at risk of a particular disease, disorder or condition, for example, tinnitus, or patients that are suffering from diseases associated with tinnitus, including by way of example only, benign paroxysmal positions vertigo, labyrinthitis, Meniere's Disease, and vestibular neuronitis. Such an amount is defined to be a "prophylactically effective amount or dose." In this use, the precise amounts also depend on the patient's state of health, weight, and the like. As used herein, a "pharmaceutical device" includes any composition described herein that, upon administration to an ear, provides a reservoir for extended release of an active agent described herein.

A "prodrug" refers to the CNS modulating agent that is converted into the parent drug in vivo. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. In one embodiment, the prodrug is designed to alter the metabolic stability or the transport characteristics of a drug, to mask side effects or toxicity, or to alter other characteristics or properties of a drug. Compounds provided herein, in some embodiments, are derivatized into suitable prodrugs.

"Round window membrane" is the membrane in humans that covers the fenestrae cochlea (also known as the circular window, fenestrae rotunda, or round window). In humans, the thickness of round window membrane is about 70 micron.

"Solubilizers" refers to auris-acceptable compounds such as triacetin, triethylcitrate, ethyl oleate, ethyl caprylate, sodium lauryl sulfate, sodium caprate, sucrose esters, alkylglucosides, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" refers to compounds such as any antioxidation agents, buffers, acids, preservatives and the like that are compatible with the environment of the targeted auris structure. Stabilizers include but are not limited to agents that will do any of (1) improve the compatibility of excipients with a container, or a delivery system, including a syringe or a glass bottle, (2) improve the stability of a component of the composition, or (3) improve composition stability.

As used herein, the term "substantially low degradation products" means less than 5% by weight of the active agent are degradation products of the active agent. In further embodiments, the term means less than 3% by weight of the active agent are degradation products of the active agent. In yet further embodiments, the term means less than 2% by weight of the active agent are degradation products of the active agent. In further embodiments, the term means less than 1% by weight of the active agent are degradation products of the active agent.

"Steady state," as used herein, is when the amount of drug administered to the targeted auris structure is equal to the amount of drug eliminated within one dosing interval resulting in a plateau or constant levels of drug exposure within the targeted structure.

As used herein, the term "subject" is used to mean any animal, preferably a mammal, including a human or non-human. The terms patient and subject may be used interchangeably. Neither term is to be interpreted as requiring the supervision of a medical professional (e.g., a doctor, nurse, physician's assistant, orderly, hospice worker).

"Surfactants" refers to compounds that are auris-acceptable, such as sodium lauryl sulfate, sodium docusate, Tween® 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants are included to enhance physical stability or for other purposes.

The terms "treat," "treating" or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Other objects, features, and advantages of the methods and compositions described herein will become apparent from the following detailed description. It should be understood, however, which the detailed description and the specific examples, while indicating specific embodiments, are given by way of illustration only.

Anatomy of the Ear

Figure 4:
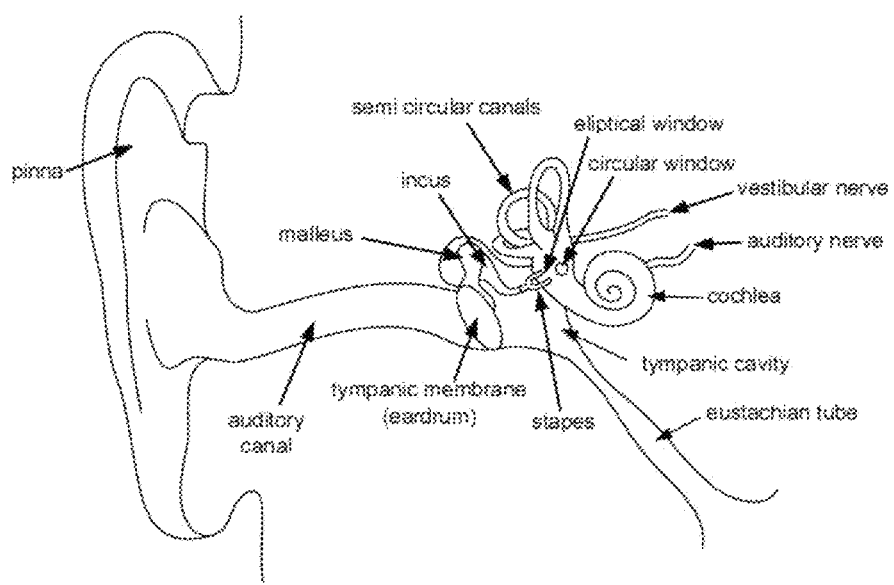
FIG. 4 provides an illustrative representation of the anatomy of the ear.

As shown in FIG. 4, the outer ear is the external portion of the organ and is composed of the pinna (auricle), the auditory canal (external auditory meatus) and the outward facing portion of the tympanic membrane, also known as the ear drum. The pinna, which is the fleshy part of the external ear that is visible on the side of the head, collects sound waves and directs them toward the auditory canal. Thus, the function of the outer ear, in part, is to collect and direct sound waves towards the tympanic membrane and the middle ear.

The middle ear is an air-filled cavity, called the tympanic cavity, behind the tympanic membrane. The tympanic membrane, also known as the ear drum, is a thin membrane that separates the external ear from the middle ear. The middle ear lies within the temporal bone, and includes within this space the three ear bones (auditory ossicles): the malleus, the incus and the stapes. The auditory ossicles are linked together via tiny ligaments, which form a bridge across the space of the tympanic cavity. The malleus, which is attached to the tympanic membrane at one end, is linked to the incus at its anterior end, which in turn is linked to the stapes. The stapes is attached to the oval window, one of two windows located within the tympanic cavity. A fibrous tissue layer, known as the annular ligament connects the stapes to the oval window. Sound waves from the outer ear first cause the tympanic membrane to vibrate. The vibration is transmitted across to the cochlea through the auditory ossicles and oval window, which transfers the motion to the fluids in the auris interna. Thus, the auditory ossicles are arranged to provide a mechanical linkage between the tympanic membrane and the oval window of the fluid-filled auris interna, where sound is transformed and transduced to the auris interna for further processing. Stiffness, rigidity or loss of movement of the auditory ossicles, tympanic membrane or oval window leads to hearing loss, e.g. otosclerosis, or rigidity of the stapes bone.

The tympanic cavity also connects to the throat via the eustachian tube. The eustachian tube provides the ability to equalize the pressure between the outside air and the middle ear cavity. The round window, a component of the auris interna but that is also accessible within the tympanic cavity, opens into the cochlea of the auris interna. The round window is covered by round window membrane, which consists of three layers: an external or mucous layer, an intermediate or fibrous layer, and an internal membrane, which communicates directly with the cochlear fluid. The round window, therefore, has direct communication with the auris interna via the internal membrane.

Movements in the oval and round window are interconnected, i.e. as the stapes bone transmits movement from the tympanic membrane to the oval window to move inward against the auris interna fluid, the round window (round window membrane) is correspondingly pushed out and away from the cochlear fluid. This movement of the round window allows movement of fluid within the cochlea, which leads in turn to movement of the cochlear inner hair cells, allowing hearing signals to be transduced. Stiffness and rigidity in round window membrane leads to hearing loss because of the lack of ability of movement in the cochlear fluid. Recent studies have focused on implanting mechanical transducers onto the round window, which bypasses the normal conductive pathway through the oval window and provides amplified input into the cochlear chamber.

Auditory signal transduction takes place in the auris interna. The fluid-filled auris interna, or inner ear, consists of two major components: the cochlear and the vestibular apparatus. The auris interna is located in part within the osseous or bony labyrinth, an intricate series of passages in the temporal bone of the skull. The vestibular apparatus is the organ of balance and consists of the three semi-circular canals and the vestibule. The three semi-circular canals are arranged relative to each other such that movement of the head along the three orthogonal planes in space can be detected by the movement of the fluid and subsequent signal processing by the sensory organs of the semi-circular canals, called the crista ampullaris. The crista ampullaris contains hair cells and supporting cells, and is covered by a dome-shaped gelatinous mass called the cupula. The hairs of the hair cells are embedded in the cupula. The semi-circular canals detect dynamic equilibrium, the equilibrium of rotational or angular movements.

When the head turns rapidly, the semicircular canals move with the head, but endolymph fluid located in the membranous semi-circular canals tends to remain stationary. The endolymph fluid pushes against the cupula, which tilts to one side. As the cupula tilts, it bends some of the hairs on the hair cells of the crista ampullaris, which triggers a sensory impulse. Because each semicircular canal is located in a different plane, the corresponding crista ampullaris of each semi-circular canal responds differently to the same movement of the head. This creates a mosaic of impulses that are transmitted to the central nervous system on the vestibular branch of the vestibulocochlear nerve. The central nervous system interprets this information and initiates the appropriate responses to maintain balance. Of importance in the central nervous system is the cerebellum, which mediates the sense of balance and equilibrium.

The vestibule is the central portion of the auris interna and contains mechanoreceptors bearing hair cells that ascertain static equilibrium, or the position of the head relative to gravity. Static equilibrium plays a role when the head is motionless or moving in a straight line. The membranous labyrinth in the vestibule is divided into two sac-like structures, the utricle and the saccule. Each structure in turn contains a small structure called a macula, which is responsible for maintenance of static equilibrium. The macula consists of sensory hair cells, which are embedded in a gelatinous mass (similar to the cupula) that covers the macula. Grains of calcium carbonate, called otoliths, are embedded on the surface of the gelatinous layer.

When the head is in an upright position, the hairs are straight along the macula. When the head tilts, the gelatinous mass and otoliths tilts correspondingly, bending some of the hairs on the hair cells of the macula. This bending action initiates a signal impulse to the central nervous system, which travels via the vestibular branch of the vestibulocochlear nerve, which in turn relays motor impulses to the appropriate muscles to maintain balance.

The cochlea is the portion of the auris interna related to hearing. The cochlea is a tapered tube-like structure that is coiled into a shape resembling a snail. The inside of the cochlea is divided into three regions, which is further defined by the position of the vestibular membrane and the basilar membrane. The portion above the vestibular membrane is the scala vestibuli, which extends from the oval window to the apex of the cochlea and contains perilymph fluid, an aqueous liquid low in potassium and high in sodium content. The basilar membrane defines the scala tympani region, which extends from the apex of the cochlea to the round window and also contains perilymph. The basilar membrane contains thousands of stiff fibers, which gradually increase in length from the round window to the apex of the cochlea. The fibers of the basement membrane vibrate when activated by sound. In between the scala vestibuli and the scala tympani is the cochlear duct, which ends as a closed sac at the apex of the cochlea. The cochlear duct contains endolymph fluid, which is similar to cerebrospinal fluid and is high in potassium.

The organ of Corti, the sensory organ for hearing, is located on the basilar membrane and extends upward into the cochlear duct. The organ of Corti contains hair cells, which have hairlike projections that extend from their free surface, and contacts a gelatinous surface called the tectorial membrane. Although hair cells have no axons, they are surrounded by sensory nerve fibers that form the cochlear branch of the vestibulocochlear nerve (cranial nerve VIII).

As discussed, the oval window, also known as the elliptical window communicates with the stapes to relay sound waves that vibrate from the tympanic membrane. Vibrations transferred to the oval window increases pressure inside the fluid-filled cochlea via the perilymph and scala vestibuli/scala tympani, which in turn causes the round window membrane to expand in response. The concerted inward pressing of the oval window/outward expansion of the round window allows for the movement of fluid within the cochlea without a change of intra-cochlear pressure. However, as vibrations travel through the perilymph in the scala vestibuli, they create corresponding oscillations in the vestibular membrane. These corresponding oscillations travel through the endolymph of the cochlear duct, and transfer to the basilar membrane. When the basilar membrane oscillates, or moves up and down, the organ of Corti moves along with it. The hair cell receptors in the Organ of Corti then move against the tectorial membrane, causing a mechanical deformation in the tectorial membrane. This mechanical deformation initiates the nerve impulse that travels via the vestibulocochlear nerve to the central nervous system, mechanically transmitting the sound wave received into signals that are subsequently processed by the central nervous system.

Diseases

Otic disorders, including auris interim and auris media disorders, produce symptoms that include but are not limited to hearing loss, nystagmus, vertigo, tinnitus, inflammation, swelling, infection and congestion. These disorders may have many causes, such as infection, injury, inflammation, tumors and adverse response to drugs or other chemical agents.

Endolymphatic Hydrops

Endolymphatic hydrops refers to an increase in the hydraulic pressure within the endolymphatic system of the inner ear. The endolymph and perilymph are separated by thin membranes that contain multiple nerves. Fluctuation in the pressure stresses the membranes and the nerves they house. If the pressure is great enough, disruptions may form in the membranes. This results in a mixing of the fluids that can lead to a depolarization blockade and transient loss of function. Changes in the rate of vestibular nerve firing often lead to vertigo. Further, the organ of Corti may also be affected. Distortions of the basilar membrane and the inner and outer hair cells can lead to hearing loss and/or tinnitus.

Causes include metabolic disturbances, hormonal imbalances, autoimmune disease, and viral, bacterial, or fungal infections. Symptoms include hearing loss, vertigo, tinnitus, and aural fullness. Nystagmus may also be present.

Kinetosis

Kinetosis, also known as motion sickness, is a condition in that there is a disconnection between visually perceived movement and the vestibular system's sense of movement. Dizziness, fatigue, and nausea are the most common symptoms of kinetosis.

Labyrinthitis

Labyrinthitis is an inflammation of the labyrinths of the ear that contain the vestibular system of the inner ear. Causes include bacterial, viral, and fungal infections. It may also be caused by a head injury or allergies. Symptoms of labyrinthitis include difficulty maintaining balance, dizziness, vertigo, tinnitus, and hearing loss. Recovery may take one to six weeks; however, chronic symptoms may be present for years.

Mal de Debarquement

Mal de debarquement is a condition that usually occurs subsequent to a sustained motion event, for example, a cruise, car trip, or airplane ride. It is characterized by a persistent sense of motion, difficulty maintaining balance, fatigue, and cognitive impairment. Symptoms may also include dizziness, headaches, hyperacusis, and/or tinnitus. Symptoms often last in excess of a month.

Meniere's Disease

Meniere's Disease is an idiopathic condition characterized by sudden attacks of vertigo, nausea and vomiting that may last for 3 to 24 hours, and may subside gradually. Progressive hearing loss, tinnitus and a sensation of pressure in the ears accompanies the disease through time. The cause of Meniere's disease is likely related to an imbalance of inner ear fluid homeostasis, including an increase in production or a decrease in reabsorption of inner ear fluid.

Studies of the vasopressin (VP)-mediated aquaporin 2 (AQP2) system in the inner ear suggest a role for VP in inducing endolymph production, thereby increasing pressure in the vestibular and cochlear structures. VP levels were found to be upregulated in endolymphatic hydrops (Meniere's Disease) cases, and chronic administration of VP in guinea pigs was found to induce endolymphatic hydrops. Treatment with VP antagonists, including infusion of OPC-31260 (a competitive antagonist of $V_2$—R) into the scala tympani resulted in a marked reduction of Meniere's disease symptoms. Other VP antagonists include WAY-140288, CL-385004, tolvaptan, conivaptan, SR 121463A and VPA 985. (Sanghi et al. *Eur. Heart* 1 (2005) 26:538-543; Palm et al. *Nephrol. Dial Transplant* (1999) 14:2559-2562).

Other studies suggest a role for estrogen-related receptor β/NR3B2 (ERR/Nr3b2) in regulating endolymph production, and therefore pressure in the vestibular/cochlear apparatus. Knock-out studies in mice demonstrate the role of the protein product of the Nr3b2 gene in regulating endolymph fluid production. Nr3b2 expression has been localized in the endolymph-secreting strial marginal cells and vestibular dark cells of the cochlea and vestibular apparatus, respectively. Moreover, conditional knockout of the Nr3b2 gene results in deafness and diminished endolymphatic fluid volume.

Meniere's Syndrome

Meniere's Syndrome, which displays similar symptoms as Meniere's disease, is attributed as a secondary affliction to another disease process, e.g. thyroid disease or inner ear inflammation due to syphilis infection. Meniere's syndrome, thus, are secondary effects to various process that interfere with normal production or reabsorption of endolymph, including endocrine abnormalities, electrolyte imbalance, autoimmune dysfunction, medications, infections (e.g. parasitic infections) or hyperlipidemia.

Ramsay Hunt's Syndrome (Herpes Zoster Infection)

Ramsay Hunt's Syndrome is caused by a herpes zoster infection of the auditory nerve. The infection may cause severe ear pain, hearing loss, vertigo, as well as blisters on the outer ear, in the ear canal, as well as on the skin of the face or neck supplied by the nerves. Facial muscles may also become paralyzed if the facial nerves are compressed by the swelling. Hearing loss may be temporary or permanent, with vertigo symptoms usually lasting from several days to weeks.

Recurrent Vestibulopathy

Recurrent vestibulopathy is a condition wherein the subject experiences multiple episodes of severe vertigo. The episodes of vertigo may last for minutes or hours. Unlike Meniere's Disease, it is not accompanied by hearing loss. In some cases it may develop into Meniere's Disease or Benign Paroxysmal Positional Vertigo.

Tinnitus

Tinnitus is defined as the perception of sound in the absence of any external stimuli. It may occur in one or both ears, continuously or sporadically, and is most often described as a ringing sound. It is most often used as a diagnostic symptom for other diseases. There are two types of tinnitus: objective and subjective. The former is a sound created in the body that is audible to anyone. The latter is audible only to the affected individual. Studies estimate that over 50 million Americans experience some form of tinnitus. Of those 50 million, about 12 million experience severe tinnitus.

Vertigo

Vertigo is described as a feeling of spinning or swaying while the body is stationary. There are two types of vertigo. Subjective vertigo is the false sensation of movement of the body. Objective vertigo is the perception that one's surrounding are in motion. It is often accompanied by nausea, vomiting, and difficulty maintaining balance.

While not wishing to be bound by any one theory, it is hypothesized that vertigo is caused by an over-accumulation of endolymph. This fluid imbalance results in increased pressure on the cells of the inner ear that leads to the sensation of movement. The most common cause of vertigo is benign paroxysmal positional vertigo, or BPPV. It can also be brought on by a head injury, or a sudden change of blood pressure. It is a diagnostic symptom of several diseases including superior canal dehiscence syndrome and Meniere's disease.

Microvascular Compression Syndrome

Microvascular compression syndrome (MCS), also called also called "vascular compression" and "neurovascular compression, is a disorder characterized by vertigo and tinnitus. It is caused by the irritation of the VII Cranial Nerve (also know as the vestibulocochlear nerve) by a blood vessel. Other symptoms found in subjects with MCS include, but are not limited to, severe motion intolerance, and neuralgic like "quick spins".

Utricular Dysfunction

The utricle is one of the two otoliths found in the vestibular labyrinth. It is responsive to both gravity and linear acceleration along the horizontal plane. Utricular dysfunction is a disorder caused by damage to the utricle. It is often characterized by a subject's perception of tilting or imbalance.

Vestibular Neuronitis

Vestibular neuronitis, or vestibular neuropathy, is an acute, sustained dysfunction of the peripheral vestibular system. It is theorized that vestibular neuronitis is caused by a disruption of afferent neuronal input from one or both of the vestibular apparatuses. Sources of this disruption include viral infection, and acute localized ischemia of the vestibular nerve and/or labyrinth.

The most significant finding when diagnosing vestibular neuronitis is spontaneous, unidirectional, horizontal nystagmus. It is often accompanied by nausea, vomiting, and vertigo. It is, generally, not accompanied by hearing loss or other auditory symptoms.

Benign Paroxysmal Positional Vertigo

Benign paroxysmal positional vertigo is caused by the movement of free floating calcium carbonate crystals (otoliths) from the utricle to one of the semicircular canals, most often the posterior semicircular canal. Movement of the head results in the movement of the otoliths causing abnormal endolymph displacement and a resultant sensation of vertigo. The episodes of vertigo usually last for about a minute and are rarely accompanied by other auditory symptoms.

Pharmaceutical Agents

Provided herein are CNS modulating compositions or compositions that ameliorate or lessen balance disorders and/or tinnitus. Otic disorders have causes and symptoms that are responsive to the pharmaceutical agents disclosed herein, or other pharmaceutical agents. CNS modulating agents that are not disclosed herein but that are useful for the amelioration or eradication of otic disorders are expressly included and intended within the scope of the embodiments presented.

In some embodiments, the CNS modulating agent is a CNS inhibitory agent. In some embodiments, the CNS inhibitory agent inhibits the transmission of a nerve impulse. In some embodiments, the CNS inhibitory agent inhibits the release of a neurotransmitter. In some embodiments, the CNS inhibitory agent agonizes the activity of a GABA receptor. In some embodiments, the CNS inhibitory agent partially or fully inhibits the repolarization of a neuron. In some embodiments, the CNS inhibitory agent disrupts the conduction of an ion channel.

Moreover, pharmaceutical agents that have been previously shown to be toxic, harmful or non-effective during systemic or localized application in other organ systems (e.g., through toxic metabolites formed after hepatic processing, toxicity of the drug in particular organs, tissues or systems, through high levels needed to achieve efficacy, through the inability to be released through systemic pathways or through poor pK characteristics) are contemplated for use with any of the compositions disclosed herein. Accordingly, pharmaceutical agents that have limited or no systemic release, systemic toxicity, poor pK characteristics or combinations thereof are contemplated within the scope of the embodiments disclosed herein.

The CNS modulating compositions disclosed herein are optionally targeted directly to otic structures where treatment is needed; for example, one embodiment contemplated is the direct application of the CNS modulating compositions disclosed herein onto the round window membrane or the crista fenestrae cochlea of the auris interna, allowing direct access and treatment of the auris interna, or inner ear components. In other embodiments, the CNS modulating composition disclosed herein is applied directly to the oval window. In yet other embodiments, direct access is obtained through microinjection directly into the auris interna, for example, through cochlear microperfusion. Such embodiments also optionally comprise a drug delivery device, wherein the drug delivery device delivers the CNS modulating compositions through use of a needle and syringe, a pump, a microinjection device or any combination thereof. In still other embodiments, application of the CNS modulating composition is targeted to the auris media through piercing of the intratympanic membrane and applying the CNS modulating composition directly to the auris media structures affected, including the walls of the tympanic cavity or auditory ossicles. By doing so, the CNS modulating compositions disclosed herein are confined to the targeted auris media structure, and will not be lost, for example, through diffusion or leakage through the eustachian tube or pierced tympanic membrane.

Some pharmaceutical agents, either alone or in combination, are ototoxic. The localized application of the potentially ototoxic drug lessens the toxic effects that occur through systemic application (e.g., through the use of lower amounts with maintained efficacy or the use of targeted amounts for a shorter period of time).

Antihistamines

Contemplated for use with the compositions disclosed herein are agents that ameliorate otic disorders, including vestibular disorders and/or tinnitus, through local modulation of central nervous system (CNS) activity. Accordingly, some embodiments incorporate the use of agents that block the action of neurotransmitters in the CNS. Histamine is a neurotransmitter in the CNS. Accordingly, some embodiments incorporate the use of agents that modulate histamine receptors (e.g. the $H_1$ receptor, $H_2$ receptor, and/or the $H_3$ receptor).

Antihistamines that target the $H_1$ receptor include, but are not limited to, meclizine, diphenhydramine, dimenhydrinate, loratadine and quetiapine. Other antihistamines include mepyramine, piperoxan, antazoline, carbinoxamine, doxylamine, clemastine, pheniramine, chlorphenamine, chlorpheniramine, dexchlorpheniramine, brompheniramine, triprolidine, cyclizine, chlorcyclizine, hydroxyzine, promethazine, alimemazine, trimeprazine, cyproheptadine, azatadine, ketotifen, oxatomide and combinations thereof. In some embodiments, the $H_1$ receptor antagonist is meclizine hydrochloride. In some embodiments, the $H_1$ receptor antagonist is promethazine hydrochloride. In some embodiments, the $H_1$ receptor antagonist is dimenhydrinate. In some embodiments, the $H_1$ receptor antagonist is diphenhydramine. In some embodiments, the $H_1$ receptor antagonist is cinnarizine. In some embodiments, the $H_1$ receptor antagonist is hydroxyzine pamoate.

Antihistamines that target the $H_3$ receptor include, but are not limited to, betahistine dihydrochloride.

GABA Receptor Modulators

Contemplated for use with the compositions disclosed herein are agents that ameliorate otic disorders, including vestibular disorders and/or tinnitus, through local modulation of central nervous system (CNS) activity. Accordingly, some embodiments incorporate the use of agents that modulate the action of GABA receptors in the CNS. GABA, or γ-aminobutyric acid, is an inhibitory neurotransmitter in the CNS. It acts at inhibitory synapses of both pre- and postsynaptic neuronal processes. The binding of GABA to its receptors (the $GABA_A$ receptor, the $GABA_B$ receptor, and the $GABA_C$ receptor) results in the opening of ion channels, and the flow of $Cl^-$ into the cell and/or $K^+$ out of the neuron. The result is hyperpolarization of the neuron. Accordingly, some embodiments incorporate the use of agents that increase or decrease the sensitivity of the GABA receptors, or activate the GABA receptors by mimicking GABA.

The benzodiazepines are agonists of the $GABA_A$ receptor. When a benzodiazepine binds to the $GABA_A$ receptor it induces a conformational change that increases the affinity of GABA for its receptor. The result of the increase in the binding of GABA is an increase in the frequency with that the CF channels in the neurons open. This causes hyperpolarization of the neural membrane. In some embodiments, the benzodiazepine is selected from the group consisting of: alprazolam, bromazepam, brotizolam, chlordiazepoxide, clonazepam, clorazepate, diazepam, estazolam, flunitrazepam, flurazepam, loprazolam, lorazepam, lormetazepam, idazolam, nimetazepam, nitrazepam, oxazepam, prazepam, temazepam, triazolam or combinations thereof. In some embodiments, the benzodiazepine is clonazepam, diazepam, lorazepam, or combinations thereof. In some embodiments, the benzodiazepine is diazepam.

In some embodiments, the GABA receptor modulator is a loop diuretic. In some embodiments, the loop diuretic is furosemide, bumetanide, or ethacrynic acid. In some embodiments, the loop diuretic is furosemide. In some embodiments, the loop diuretic is bumetanide. In some embodiments, the loop diuretic is ethacrynic acid. Furosemide, for example, binds to the $GABA_A$ receptor and reversibly antagonizes GABA-evoked currents of the α6, β2, and γ2 receptors. By way of example only, useful loop diuretics include, but are not limited to, furosemide, bumetanide, and ethacrynic acid.

In some embodiments, the modulator of a GABA receptor is a GABA analogue. GABA analogues mimic GABA. Thus, when they bind to a GABA receptor, the receptor acts as though GABA is binding to it and the receptor is activated. In some embodiments, the GABA analog is gabapentin, pregabalin, muscimol, or baclofen. In some embodiments, the GABA analog is gabapentin. In some embodiments, the GABA analog is pregabalin. In some embodiments, the GABA analog is muscimol. In some embodiments, the GABA analogue is baclofen. Baclofen is an analogue of GABA that binds to and activates the $GABA_B$ receptor. Muscimol is also an analogue of GABA. In some embodiments, muscimol agonizes the $GABA_A$ receptor.

Neurotransmitter Reuptake Inhibitors

Contemplated for use with the compositions disclosed herein are agents that ameliorate otic disorders, including vestibular disorders and/or tinnitus, through local modulation of central nervous system (CNS) activity. Accordingly, some embodiments incorporate the use of agents that inhibit the reuptake of neurotransmitters in the CNS. Neurotransmitter reuptake inhibitors inhibit the reuptake of neurotransmitters into presynaptic cells of the CNS. This increases the concentration of neurotransmitter available to stimulate post-synaptic cells of the CNS.

In some embodiments, the neurotransmitter reuptake inhibitors are tricyclic antidepressants. Tricyclic antidepressants work by inhibiting the re-uptake of the neurotransmitters norepinephrine and serotonin by pre-synaptic cells. This increases the level of serotonin and/or norepinephrine available to bind to the postsynaptic receptor. In some embodiments, the tricyclic antidepressant is amitriptyline, nortriptyline, or trimipramine. In some embodiments, the tricyclic antidepressant is amitriptyline. In some embodiments, the tricyclic antidepressant is nortriptyline. In some embodiments, the tricyclic antidepressant is trimipramine.

In some embodiments, the neurotransmitter reuptake inhibitor is a selective serotonin reuptake inhibitor. By inhibiting the reuptake of serotonin into the presynaptic cells, SSRIs increase the extracellular level of serotonin. This increases the level of serotonin available to bind to the postsynaptic receptor. SSRIs are hypothesized to stimulate new neural growth within the inner ear. In some embodiments, the selective serotonin reuptake inhibitor is fluoxetine, paroxetine, or sertraline. In some embodiments, the selective serotonin reuptake inhibitor is fluoxetine. In some embodiments, the selective serotonin reuptake inhibitor is paroxetine. In some embodiments, the selective serotonin reuptake inhibitor is sertraline.

Anticholinergics

Contemplated for use with the compositions disclosed herein are agents that ameliorate otic disorders, including vestibular disorders and/or tinnitus, through local modulation of central nervous system (CNS) activity. Accordingly, some embodiments incorporate the use of agents that inhibit the release of the neurotransmitter acetylcholine in the CNS. Anticholinergic agents are substances that block acetylcholine in the central and the peripheral nervous system. They treat balance disorders by suppressing conduction in vestibular cerebellar pathways, thus increasing motion tolerance.

In some embodiments, the anticholinergic is glycopyrrolate, homatropine, scopolamine or atropine. In some embodiments, the anticholinergic is glycopyrrolate. In some embodiments, the anticholinergic is homatropine. In some embodiments, the anticholinergic is scopolamine. In some embodiments, the anticholinergic is atropine.

Local Anesthetics

Contemplated for use with the compositions disclosed herein are agents that ameliorate otic disorders, including vestibular disorders and/or tinnitus, through local modulation of central nervous system (CNS) activity. Accordingly, some embodiments incorporate the use of agents that decrease the rate of the depolarization and repolarization of neurons by, for example, blocking the $Na^+$ channels in cell membranes.

In some embodiments, the CNS modulator is a local anesthetic. In some embodiments, the local anesthetic is selected from the group consisting of: benzocaine, carticaine, cinchocaine, cyclomethycaine, lidocaine, prilocalne, propxycaine, proparacaine, tetracaine, tocamide, and trimecaine. In some embodiments, the local anesthetic is lidocaine. In some embodiments, the local anesthetic is tocamide.

Sodium Channel Blockers

Contemplated for use with the compositions disclosed herein are agents that ameliorate otic disorders, including vestibular disorders and/or tinnitus, through local modulation of central nervous system (CNS) activity. Accordingly, some embodiments incorporate the use of agents that block or antagonize Na+ channels. Sodium channels are channels formed in the plasma membrane of neurons (amongst other cells) by integral membrane proteins. These channels conduct $Na^+$ through a cell's plasma membrane. In neurons, the flow of $Na^+$ is partly responsible for creating and propagating action potentials in the neurons.

In some embodiments, the sodium channel blocker is carbamazepine, oxcarbazepine, phenylein, valproic acid, or sodium valproate. In some embodiments, the sodium channel blocker is carbamazepine. In some embodiments, the sodium channel blocker is oxcarbazepine. In some embodiments, the sodium channel blocker is phenylein. In some embodiments, the sodium channel blocker is valproic acid. In some embodiments, the sodium channel blocker is sodium valproate.

Calcium Channel Blockers

Contemplated for use with the compositions disclosed herein are agents that ameliorate otic disorders, including vestibular disorders and/or tinnitus, through local modulation of central nervous system (CNS) activity. Accordingly, some embodiments incorporate the use of agents that block or antagonize Ca+ channels. Calcium channels are channels formed in the plasma membrane of neurons (amongst other cells) by integral membrane proteins. These channels conduct $Ca^+$ through a cell's plasma membrane. In neurons, the flow of $Ca^{2+}$ is partly responsible for creating and propagating action potentials in neurons. It can also be responsible for the release of certain neurotransmitters.

In some embodiments, the calcium channel antagonist is cinnarizine, flunarizine, or nimodipine. In some embodiments, the calcium channel antagonist is cinnarizine. In some embodiments, the calcium channel antagonist is flunarizine. In some embodiments, the calcium channel antagonist is nimodipine.

Thyrotropin-Releasing Hormone

Contemplated for use with the compositions disclosed herein are agents that ameliorate otic disorders, including vestibular disorders and/or tinnitus, through local modulation of central nervous system (CNS) activity. Accordingly, some embodiments incorporate the use of agents that modulate neurotransmitters. Thyrotropin-releasing hormone is a neurotransmitter that inhibits glutamate-induced excitation of neurons. In some embodiments, the CNS modulator is thyrotropin-releasing hormone.

In some embodiments, the compositions further comprise a CNS modulator as an immediate release agent (i.e. an immediate release CNS agent). In some embodiments, the immediate release CNS modulator is the same agent as the controlled-release agent, a different CNS modulator, an additional therapeutic agent, or a combination thereof.

Concentration of Active Agent

In some embodiments, the concentration of a CNS modulating agent in a pharmaceutical composition or device described herein is about 1% by weight of the composition. In some embodiments, the concentration of a CNS modulating agent in a pharmaceutical composition or device described herein is about 2% by weight of the composition. In some embodiments, the concentration of a CNS modulating agent in a pharmaceutical composition or device described herein is about 3% by weight of the composition. In some embodiments, the concentration of a CNS modulating agent in a pharmaceutical composition or device described herein is about 4% by weight of the composition. In some embodiments, the concentration of a CNS modulating agent in a pharmaceutical composition or device described herein is about 5% by weight of the composition. In some embodiments, the concentration of a CNS modulating agent in a pharmaceutical composition or device described herein is about 10% by weight of the composition. In some embodiments, the concentration of a CNS modulating agent in a pharmaceutical composition or device described herein is about 15% by weight of the composition. In some embodiments, the concentration of a CNS modulating agent in a pharmaceutical composition or device described herein is about 20% by weight of the composition. In some embodiments, the concentration of a CNS modulating agent in a pharmaceutical composition or device described herein is about 25% by weight of the composition. In some embodiments, the concentration of a CNS modulating agent in a pharmaceutical composition or device described herein is about 30% by weight of the composition. In some embodiments, the concentration of a CNS modulating agent in a pharmaceutical composition or device described herein is about 40% by weight of the composition. In some embodiments, the concentration of a CNS modulating agent in a pharmaceutical composition or device described herein is about 50% by weight of the composition. In some embodiments, the concentration of a CNS modulating agent in a pharmaceutical composition or device described herein is about 60% by weight of the composition. In some embodiments, the concentration of a CNS modulating agent in a pharmaceutical composition or device described herein is about 70% by weight of the composition. In some embodiments, the concentration of a CNS modulating agent in a pharmaceutical composition or device described herein is about 80% by weight of the composition. In some embodiments, the concentration of a CNS modulating agent in a pharmaceutical composition or device described herein is about 90% by weight of the composition.

In some embodiments, the compositions described herein have a concentration of active pharmaceutical ingredient, or pharmaceutically acceptable prodrug or salt thereof, between about 0.1 to about 70 mg/mL, between about 0.5 mg/mL to about 70 mg/mL, between about 0.5 mg/mL to about 50 mg/mL, between about 0.5 mg/mL to about 20 mg/mL, between about 1 mg to about 70 mg/mL, between about 1 mg to about 50 mg/mL, between about 1 mg/mL and about 20 mg/mL, between about 1 mg/mL to about 10 mg/mL, or between about 1 mg/mL to about 5 mg/mL, of the active agent, or pharmaceutically acceptable prodrug or salt thereof, by volume of the composition.

Combination Therapy

In some embodiments, the compositions disclosed herein further comprise an additional therapeutic agent. In some embodiments, the additional therapeutic agent is an acidifying agent, an anesthetic, an analgesic, an antibiotic, antiemetic, an antifungal, an anti-microbial agent, an antipsychotic (especially those in the phenothiazine class), an antiseptic, an antiviral, an astringent, a chemotherapeutic agent, a collagen, a corticosteroid, a diuretic, a keratolytic agent, a nitric oxide synthase inhibitor, or combinations thereof.

Acidifying Agents

Acidifying agents are optionally used in combination with the compositions disclosed herein. Acidifying agents lower the pH level of the vestibular environment making it unfavorable to most microbial growth. Acidifying agents include, but are not limited to, acetic acid.

Anti-Emetic Agents

Anti-Emetic agents are optionally used in combination with the compositions disclosed herein. Anti-emetic agents include promethazine, prochlorperazine, trimethobenzamide, and triethylperazine. Other anti-emetic agents include 5HT3 antagonists such as dolasetron, granisetron, ondansetron, tropisetron, and palonosetron; and neuroleptics such as droperidol. Further anti-emetic agents include antihistamines, such as meclizine; phenothiazines such as perphenazine, and thiethyl perazine; dopamine antagonists, including domperidone, properidol, haloperidol, chlorpromazine, promethazine, prochlorperazine, metoclopramide and combinations thereof; cannabinoids, including dronabinol, nabilone, sativex, and combinations thereof; anticholinergics, including scopolamine; and steroids, including dexamethasone; trimethobenzamine, emetrol, propofol, muscimol, and combinations thereof.

Antimicrobial Agents

Antimicrobial agents are also contemplated as useful with the compositions disclosed herein. Antimicrobial agents include agents that act to inhibit or eradicate microbes, including bacteria, fungi or parasites. Specific antimicrobial agents may be used to combat specific microbes. Accordingly, a skilled practitioner would know that antimicrobial agent would be relevant or useful depending on the microbe identified, or the symptoms displayed. Antimicrobial agents include antibiotics, antiviral agents, antifungal agents, and antiparasitic agents.

Antibiotics include, but are not limited to, amikacin, gentamicin, kanamycin, neomycin, netilmicin, streptomycin, tobramycin, paromomycin, geldanmycin, herbimycin, loracarbef, ertapenem, doripenem, imipenem, cilastatin, meropenem, cefadroxil, cefazolin, cefalotin, cefalexin, cefaclor, cefamandole, cefoxitin, defprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, teicoplanin, vancomycin, azithromycin, clarithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, meticillin, nafcillin, oxacillin, penicillin, piperacillin, ticarcillan, bacitracin, colistin, polymyxin B, ciprofloxacin, enoxacin, gatifloxacin, levofloxacin, lomefloxacin, moxifloxacin, norfloxacin, ofloxacin, trovfloxacin, mafenide, prontosil, sulfacetamide, sulfamethizole, sulfanimilmde, sulfsalazine, sulfsioxazole, trimethoprim, demeclocycline, doxycycline, minocycline, oxetracycline, tetracycline, arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinuspristin/dalfopristin, rifampin, tinidazole, and combinations thereof.

Antiviral agents include, but are not limited to, acyclovir, famciclovir and valacyclovir. Other antiviral agents include abacavir, aciclovir, adfovir, amantadine, amprenavir, arbidol, atazanavir, artipla, brivudine, cidofovir, combivir, edoxudine, efavirenz, emtricitabine, enfuvirtide, entecavir, fomvirsen, fosamprenavir, foscarnet, fosfonet, ganciclovir, gardasil, ibacitabine, immunovir, idoxuridine, imiquimod, indinavir, inosine, integrase inhibitors, interferons, including interferon type III, interferon type II, interferon type I, lamivudine, lopinavir, loviride, MK-0518, maraviroc, moroxydine, nelfinavir, nevirapine, nexavir, nucleoside analogues, oseltamivir, penciclovir, peramivir, pleconaril, podophyllotoxin, protease inhibitors, reverse transcriptase inhibitors, ribavirin, rimantadine, ritonavir, saquinavir, stavudine, tenofovir, tenofovir disoproxil, tipranavir, trifluridine, trizivir, tromantadine, truvada, valganciclovir, vicriviroc, vidarabine, viramidine, zalcitabine, zanamivir, zidovudine, and combinations thereof.

Antifungal agents include, but are not limited to, ammolfine, utenafine, naftifine, terbinafine, flucytosine, fluconazole, itraconazole, ketoconazole, posaconazole, ravuconazole, voriconazole, clotrimazole, econazole, miconazole, oxiconazole, sulconazole, terconazole, tioconazole, nikkomycin Z, caspofungin, micafungin, anidulafungin, amphotericin B, liposomal nystastin, pimaricin, griseofulvin, ciclopirox olamine, haloprogin, tolnaftate, undecylenate, and combinations thereof. Antiparasitic agents may include amitraz, amoscanate, avermectin, carbadox, diethylcarbamizine, dimetridazole, diminazene, ivermectin, macrofilaricide, malathion, mitaban, oxamiquine, permethrin, praziquantel, prantel pamoate, selamectin, sodium stibogluconate, thiabendazole, and combinations thereof.

Anti-Septic Agents

Anti-septic agents are also contemplated as useful with the compositions disclosed herein. Anti-septic agents include, but are not limited to, acetic acid, boric acid, gentian violet, hydrogen peroxide, carbamide peroxide, chlorhexidine, saline, mercurochrome, povidone iodine, polyhyroxine iodine, cresylate and aluminum acetate, and mixtures thereof.

Astringents

Astringents are also contemplated as useful with the compositions disclosed herein. Astringents include, but are not limited to, isopropyl alcohol, ethanol and propylene glycol.

Corticosteroids

Corticosteroids are also contemplated as useful with the compositions disclosed herein. Corticosteroids include, but are not limited to, hydrocortisone, prednisone, fluprednisolone, dexamethasone, betamethasone, betamethasone valerate, methylprednisolone, fluocinolone acetonide, flurandrenolone acetonide, fluorometholone, cortisone, prednisolone, alclometasone, amcinonide, betamethasone, clobetasol, clocortolone, desonide, desoximetasone, diflorasone, fluocinonide, flurandrenolide, fluticasone, halcinonide, halobetasol, mometasone, flumethasone, prednicarbate and triamcinolone, and mixtures thereof.

Platelet Activating Factor Antagonists

Platelet activating factor antagonists are also contemplated for use in combination with the CNS modulating compositions disclosed herein. Platelet activating factor antagonists include, by way of example only, kadsurenone, phomactin G, ginsenosides, apafant (4-(2-chlorophenyl)-9-methyl-2[3(4-morpholinyl)-3-propanol-1-yl[6H-thieno[3.2-f[[1.2.4]triazolo]4,3-1]]1.4]diazepine), A-85783, BN-52063, BN-52021, BN-50730 (tetrahedra-4,7,8,10 methyl-1 (chloro-1 phenyl)-6 (methoxy-4 phenyl-carbamoyl)-9 pyrido[4',3'-4,5]thieno[3, 2-f]triazolo-1,2,4[4,3-a]diazepine-1,4), BN 50739, SM-12502, RP-55778, Ro 24-4736, SR27417A, CV-6209, WEB 2086, WEB 2170, 14-deoxyandrographolide, CL 184005, CV-3988, TCV-309, PMS-601, TCV-309 and combinations thereof.

Presented below (Table 1) are examples of active agents contemplated for use with the compositions and devices disclosed herein. In sone embodiments, one or more active agents disclosed in Table 1 are used in a composition or device described herein.

TABLE 1

| Auris Condition | Therapeutic Agent |
| --- | --- |
| Benign Paroxysmal Positional Vertigo | Diphenhydramine |
| Benign Paroxysmal Positional Vertigo | Lorazepam |
| Benign Paroxysmal Positional Vertigo | Meclizine |
| Benign Paroxysmal Positional Vertigo | Oldansetron |
| Hearing Loss | Estrogen |
| AIED | Etanercept (Enbrel) |
| AIED | GW3333 |
| AIED | Copaxone |
| Hearing Loss | Estrogen and progesterone (E + P) |
| Hearing Loss | Folic acid |
| Hearing Loss | Lactated Ringer's with 0.03% Ofloxacin |
| Hearing Loss | Methotrexate |
| Hearing Loss | N-acetyl cysteine |
| Meniere's Disease | Betahistine |
| Meniere's Disease | Sildenafil |
| Meniere's Disease | Tacrolimus |
| Middle Ear Effusion | Pneumonococcal vaccine |
| Otitis Externa | Diclofenac sodium; dexotc |
| Otitis Externa, Acute | AL-15469A/AL-38905 |
| Otitis Media | Amoxicillin/clavulanate |
| Otitis Media | Dornase alfa |
| Otitis Media | *Echinacea purpurea* |
| Otitis Media | Faropenem medoxomil |
| Otitis Media | Levofloxacin |
| Otitis Media | PNCRM9 |
| Otitis Media | Pneumococcal vaccine |
| Otitis Media | Telithromycin |
| Otitis Media | Zmax |
| Otitis Media with Effusion | Lansoprazole |
| Otitis Media, Acute | AL-15469A; AL-38905 |
| Otitis Media, Acute | Amoxicillin |
| Otitis Media, Acute | Amoxicillin-clavulanate |
| Otitis Media, Acute | Azithromycin |
| Otitis Media, Acute | Azithromycin SR |
| Otitis Media, Acute | Cefdinir |
| Otitis Media, Acute | Hyland's earache drops |
| Otitis Media, Acute | Montelukast |
| Otitis Media, Acute | Pneumonococcal vaccine |
| Otitis Media, Acute with Typanostomy Tubes | AL-15469A/AL38905 |
| Otitis Media, Chronic | Sulfamethoxazole-trimethoprim |
| Otitis Media, Suppurative | Azithromycin |

TABLE 1-continued

| Auris Condition | Therapeutic Agent |
|---|---|
| Otitis Media, Suppurative | Telithromycin |
| Otosclerosis | Acetylcysteine |
| Ototoxicity | Aspirin |
| Tinnitus | Acamprosate |
| Tinnitus | Gabapentin |
| Tinnitus | Modafinil |
| Tinnitus | Neramexane |
| Tinnitus | Neramexane mesylate |
| Tinnitus | Piribedil |
| Tinnitus | Vardenafil |
| Tinnitus | Vestipitant + Paroxetine |
| Tinnitus | Vestiplitant |
| Tinnitus | Zinc sulfate |

In some embodiments, the additional therapeutic agent is an immediate release agent. In some embodiments, the additional therapeutic agent is a controlled-release agent.

General Methods of Sterilization

Provided herein are otic compositions that ameliorate or lessen otic disorders described herein. Further provided herein, in some embodiments, are methods comprising the administration of said otic compositions. In some embodiments, the compositions or devices are sterilized. Included within the embodiments disclosed herein are means and processes for sterilization of a pharmaceutical composition or device disclosed herein for use in humans. The goal is to provide a safe pharmaceutical product, relatively free of infection causing micro-organisms. The U.S. Food and Drug Administration has provided regulatory guidance in the publication "Guidance for Industry: Sterile Drug Products Produced by Aseptic Processing" available at: http://www.fda.gov/cder/guidance/5882fnl.htm, which is incorporated herein by reference in its entirety.

As used herein, "sterilization" means a process used to destroy or remove microorganisms that are present in a product or packaging. Any suitable method available for sterilization of objects and compositions is contemplated for use with the compositions and devices disclosed herein. Available methods for the inactivation of microorganisms include, but are not limited to, the application of extreme heat, lethal chemicals, or gamma radiation. Disclosed herein, in some embodiments, are processes for the preparation of an otic therapeutic composition comprising subjecting the composition to a sterilization method selected from heat sterilization, chemical sterilization, radiation sterilization or filtration sterilization. The method used depends largely upon the nature of the device or composition to be sterilized. Detailed descriptions of many methods of sterilization are given in Chapter 40 of Remington: The Science and Practice of Pharmacy published by Lippincott, Williams & Wilkins, and is incorporated by reference with respect to this subject matter.

Sterilization by Heat

Many methods are available for sterilization by the application of extreme heat. One method is through the use of a saturated steam autoclave. In this method, saturated steam at a temperature of at least 121° C. is allowed to contact the object to be sterilized. The transfer of heat is either directly to the microorganism, in the case of an object to be sterilized, or indirectly to the microorganism by heating the bulk of an aqueous solution to be sterilized. This method is widely practiced as it allows flexibility, safety and economy in the sterilization process.

Dry heat sterilization is a method that is used to kill microorganisms and perform depyrogenation at elevated temperatures. This process takes place in an apparatus suitable for heating HEPA-filtered microorganism-free air to temperatures of at least 130-180° C. for the sterilization process and to temperatures of at least 230-250° C. for the depyrogenation process. Water to reconstitute concentrated or powdered compositions is also sterilized by autoclave. In some embodiments, the compositions described herein comprise micronized pharmaceutical that are sterilized by dry heating, e.g., heating for about 7-11 hours at internal powder temperatures of 130-140° C., or for 1-2 hours at internal temperatures of 150-180° C.

Chemical Sterilization

Chemical sterilization methods are an alternative for products that do not withstand the extremes of heat sterilization. In this method, a variety of gases and vapors with germicidal properties, such as ethylene oxide, chlorine dioxide, formaldehyde or ozone are used as the anti-apoptotic agents. The germicidal activity of ethylene oxide, for example, arises from its ability to serve as a reactive alkylating agent. Thus, the sterilization process requires the ethylene oxide vapors to make direct contact with the product to be sterilized.

Radiation Sterilization

One advantage of radiation sterilization is the ability to sterilize many types of products without heat degradation or other damage. The radiation commonly employed is beta radiation or alternatively, gamma radiation from a $^{60}$Co source. The penetrating ability of gamma radiation allows its use in the sterilization of many product types, including solutions, compositions and heterogeneous mixtures. The germicidal effects of irradiation arise from the interaction of gamma radiation with biological macromolecules. This interaction generates charged species and free radicals. Subsequent chemical reactions, such as rearrangements and cross-linking processes, result in the loss of normal function for these biological macromolecules. The compositions described herein are also optionally sterilized using beta irradiation.

Filtration

Filtration sterilization is a method used to remove but not destroy microorganisms from solutions. Membrane filters are used to filter heat-sensitive solutions. Such filters are thin, strong, homogenous polymers of mixed cellulosic esters (MCE), polyvinylidene fluoride (PVF; also known as PVDF), or polytetrafluoroethylene (PTFE) and have pore sizes ranging from 0.1 to 0.22 µm. Solution's of various characteristics are optionally filtered using different filter membranes. For example, PVF and PTFE membranes are well suited to filtering organic solvents while aqueous solutions are filtered through PVF or MCE membranes. Filter apparatus are available for use on many scales ranging from the single point-of-use disposable filter attached to a syringe up to commercial scale filters for use in manufacturing plants. The membrane filters are sterilized by autoclave or chemical sterilization. Validation of membrane filtration systems is performed following standardized protocols (Microbiological Evaluation of Filters for Sterilizing Liquids, Vol 4, No. 3. Washington, D.C: Health Industry Manufacturers Association, 1981) and involve challenging the membrane filter with a known quantity (ca. $10^7/cm^2$) of unusually small microorganisms, such as *Brevundimonas diminuta* (ATCC 19146).

Pharmaceutical compositions are optionally sterilized by passing through membrane filters. Compositions comprising nanoparticles (U.S. Pat. No. 6,139,870) or multilamellar vesicles (Richard et al., International Journal of Pharmaceutics (2006), 312(1-2):144-50) are amenable to sterilization by filtration through 0.22 µm filters without destroying their organized structure.

In some embodiments, the methods disclosed herein comprise sterilizing the composition (or components thereof) by means of filtration sterilization. In another embodiment the auris-acceptable otic therapeutic agent composition comprises a particle wherein the particle composition is suitable for filtration sterilization. In a further embodiment said particle composition comprises particles of less than 300 nm in size, of less than 200 nm in size, of less than 100 nm in size. In another embodiment the auris-acceptable composition comprises a particle composition wherein the sterility of the particle is ensured by sterile filtration of the precursor component solutions. In another embodiment the auris-acceptable composition comprises a particle composition wherein the sterility of the particle composition is ensured by low temperature sterile filtration. In a further embodiment, low temperature sterile filtration is carried out at a temperature between 0 and 30° C., between 0 and 20° C., between 0 and 10° C., between 10 and 20° C., or between 20 and 30° C.

In another embodiment is a process for the preparation of an auris-acceptable particle composition comprising: filtering the aqueous solution containing the particle composition at low temperature through a sterilization filter; lyophilizing the sterile solution; and reconstituting the particle composition with sterile water prior to administration. In some embodiments, a composition described herein is manufactured as a suspension in a single vial composition containing the micronized active pharmaceutical ingredient. A single vial composition is prepared by aseptically mixing a sterile poloxamer solution with sterile micronized active ingredient (e.g., PD98059) and transferring the composition to sterile pharmaceutical containers. In some embodiments, a single vial containing a composition described herein as a suspension is resuspended before dispensing and/or administration.

In specific embodiments, filtration and/or filling procedures are carried out at about 5° C. below the gel temperature ($T_{gel}$) of a composition described herein and with viscosity below a theoretical value of 100 cP to allow for filtration in a reasonable time using a peristaltic pump.

In another embodiment the auris-acceptable otic therapeutic agent composition comprises a nanoparticle composition wherein the nanoparticle composition is suitable for filtration sterilization. In a further embodiment the nanoparticle composition comprises nanoparticles of less than 300 nm in size, of less than 200 nm in size, or of less than 100 nm in size. In another embodiment the auris-acceptable composition comprises a microsphere composition wherein the sterility of the microsphere is ensured by sterile filtration of the precursor organic solution and aqueous solutions. In another embodiment the auris-acceptable composition comprises a thermoreversible gel composition wherein the sterility of the gel composition is ensured by low temperature sterile filtration. In a further embodiment, the low temperature sterile filtration occurs at a temperature between 0 and 30° C., or between 0 and 20° C., or between 0 and 10° C., or between 10 and 20° C., or between 20 and 30° C. In another embodiment is a process for the preparation of an auris-acceptable thermoreversible gel composition comprising: filtering the aqueous solution containing the thermoreversible gel components at low temperature through a sterilization filter; lyophilizing the sterile solution; and reconstituting the thermoreversible gel composition with sterile water prior to administration.

In certain embodiments, the active ingredients are dissolved in a suitable vehicle (e.g. a buffer) and sterilized separately (e.g. by heat treatment, filtration, gamma radiation). In some instances, the active ingredients are sterilized separately in a dry state. In some instances, the active ingredients are sterilized as a suspension or as a colloidal suspension. The remaining excipients (e.g., fluid gel components present in auris compositions) are sterilized in a separate step by a suitable method (e.g. filtration and/or irradiation of a cooled mixture of excipients); the two solutions that are separately sterilized are then mixed aseptically to provide a final auris composition. In some instances, the final aseptic mixing is performed just prior to administration of a composition described herein.

In some instances, conventionally used methods of sterilization (e.g., heat treatment (e.g., in an autoclave), gamma irradiation, filtration) lead to irreversible degradation of polymeric components (e.g., thermosetting, gelling or mucoadhesive polymer components) and/or the active agent in the composition. In some instances, sterilization of an auris composition by filtration through membranes (e.g., 0.2 μM membranes) is not possible if the composition comprises thixotropic polymers that gel during the process of filtration.

Accordingly, provided herein are methods for sterilization of auris compositions that prevent degradation of polymeric components (e.g., thermosetting and/or gelling and/or mucoadhesive polymer components) and/or the active agent during the process of sterilization. In some embodiments, degradation of the active agent (e.g., any therapeutic otic agent described herein) is reduced or eliminated through the use of specific pH ranges for buffer components and specific proportions of gelling agents in the compositions. In some embodiments, the choice of an appropriate gelling agent and/or thermosetting polymer allows for sterilization of compositions described herein by filtration. In some embodiments, the use of an appropriate thermosetting polymer and an appropriate copolymer (e.g., a gelling agent) in combination with a specific pH range for the composition allows for high temperature sterilization of compositions described with substantially no degradation of the therapeutic agent or the polymeric excipients. An advantage of the methods of sterilization provided herein is that, in certain instances, the compositions are subjected to terminal sterilization via autoclaving without any loss of the active agent and/or excipients and/or polymeric components during the sterilization step and are rendered substantially free of microbes and/or pyrogens.

Microorganisms

Provided herein are auris-acceptable compositions or devices that ameliorate or lessen otic disorders described herein. Further provided herein are methods comprising the administration of said otic compositions. In some embodiments, the compositions or devices are substantially free of microorganisms. Acceptable sterility levels are based on applicable standards that define therapeutically acceptable otic compositions, including but not limited to United States Pharmacopeia Chapters <1111> et seq. For example, acceptable sterility levels include about 10 colony forming units (cfu) per gram of composition, about 50 cfu per gram of composition, about 100 cfu per gram of composition, about 500 cfu per gram of composition or about 1000 cfu per gram of composition. In some embodiments, acceptable sterility levels for compositions include less than 10 cfu/mL, less that 50 cfu/mL, less than 500 cfu/mL or less than 1000 cfu/mL microbial agents. In addition, acceptable sterility levels include the exclusion of specified objectionable microbiological agents. By way of example, specified objectionable microbiological agents include but are not limited to *Escherichia coli* (*E. coli*), *Salmonella* sp., *Pseudomonas aeruginosa* (*P. aeruginosa*) and/or other specific microbial agents.

Sterility of the auris-acceptable otic therapeutic agent composition is confirmed through a sterility assurance program in accordance with United States Pharmacopeia Chapters <61>, <62> and <71>. A key component of the sterility assurance quality control, quality assurance and validation process is the method of sterility testing. Sterility testing, by way of example only, is performed by two methods. The first is direct inoculation wherein a sample of the composition to be tested is added to growth medium and incubated for a period of time up to 21 days. Turbidity of the growth medium indicates contamination. Drawbacks to this method include the small sampling size of bulk materials that reduces sensitivity, and detection of microorganism growth based on a visual observation. An alternative method is membrane filtration sterility testing. In this method, a volume of product is passed through a small membrane filter paper. The filter paper is then placed into media to promote the growth of microorganisms. This method has the advantage of greater sensitivity as the entire bulk product is sampled. The commercially available Millipore Steritest sterility testing system is optionally used for determinations by membrane filtration sterility testing. For the filtration testing of creams or ointments Steritest filter system No. TLHVSL210 are used. For the filtration testing of emulsions or viscous products Steritest filter system No. TLAREM210 or TDAREM210 are used. For the filtration testing of pre-filled syringes Steritest filter system No. TTHASY210 are used. For the filtration testing of material dispensed as an aerosol or foam Steritest filter system No. TTHVA210 are used. For the filtration testing of soluble powders in ampoules or vials Steritest filter system No. TTHADA210 or TTHADV210 are used.

Testing for *E. coli* and *Salmonella* includes the use of lactose broths incubated at 30-35° C. for 24-72 hours, incubation in MacConkey and/or EMB agars for 18-24 hours, and/or the use of Rappaport medium. Testing for the detection of *P. aeruginosa* includes the use of NAC agar. United States Pharmacopeia Chapter <62> further enumerates testing procedures for specified objectionable microorganisms.

In certain embodiments, any controlled-release composition described herein has less than about 60 colony forming units (CFU), less than about 50 colony forming units, less than about 40 colony forming units, or less than about 30 colony forming units of microbial agents per gram of composition. In certain embodiments, the otic compositions described herein are formulated to be isotonic with the endolymph and/or the perilymph.

Endotoxins

Provided herein are otic compositions that ameliorate or lessen otic disorders described herein. Further provided herein are methods comprising the administration of said otic compositions. In some embodiments, the compositions or devices are substantially free of endotoxins. An additional aspect of the sterilization process is the removal of by-products from the killing of microorganisms (hereinafter, "Product"). The process of depyrogenation removes pyrogens from the sample. Pyrogens are endotoxins or exotoxins that induce an immune response. An example of an endotoxin is the lipopolysaccharide (LPS) molecule found in the cell wall of gram-negative bacteria. While sterilization procedures such as autoclaving or treatment with ethylene oxide kill the bacteria, the LPS residue induces a proinflammatory immune response, such as septic shock. Because the molecular size of endotoxins can vary widely, the presence of endotoxins is expressed in "endotoxin units" (EU). One EU is equivalent to 100 picograms of *E. coli* LPS. Humans can develop a response to as little as 5 EU/kg of body weight. The sterility is expressed in any units as recognized in the art. In certain embodiments, otic compositions described herein contain lower endotoxin levels (e.g. <4 EU/kg of body weight of a subject) when compared to conventionally acceptable endotoxin levels (e.g., 5 EU/kg of body weight of a subject). In some embodiments, the auris-acceptable otic therapeutic agent composition has less than about 5 EU/kg of body weight of a subject. In other embodiments, the auris-acceptable otic therapeutic agent composition has less than about 4 EU/kg of body weight of a subject. In additional embodiments, the auris-acceptable otic therapeutic agent composition has less than about 3 EU/kg of body weight of a subject. In additional embodiments, the auris-acceptable otic therapeutic agent composition has less than about 2 EU/kg of body weight of a subject.

In some embodiments, the auris-acceptable otic therapeutic agent composition or device has less than about 5 EU/kg of composition. In other embodiments, the auris-acceptable otic therapeutic agent composition has less than about 4 EU/kg of composition. In additional embodiments, the auris-acceptable otic therapeutic agent composition has less than about 3 EU/kg of composition. In some embodiments, the auris-acceptable otic therapeutic agent composition has less than about 5 EU/kg Product. In other embodiments, the auris-acceptable otic therapeutic agent composition has less than about 1 EU/kg Product. In additional embodiments, the auris-acceptable otic therapeutic agent composition has less than about 0.2 EU/kg Product. In some embodiments, the auris-acceptable otic therapeutic agent composition has less than about 5 EU/g of unit or Product. In other embodiments, the auris-acceptable otic therapeutic agent composition has less than about 4 EU/g of unit or Product. In additional embodiments, the auris-acceptable otic therapeutic agent composition has less than about 3 EU/g of unit or Product. In some embodiments, the auris-acceptable otic therapeutic agent composition has less than about 5 EU/mg of unit or Product. In other embodiments, the auris-acceptable otic therapeutic agent composition has less than about 4 EU/mg of unit or Product. In additional embodiments, the auris-acceptable otic therapeutic agent composition has less than about 3 EU/mg of unit or Product. In certain embodiments, otic compositions described herein contain from about 1 to about 5 EU/mL of composition. In certain embodiments, otic compositions described herein contain from about 2 to about 5 EU/mL of composition, from about 3 to about 5 EU/mL of composition, or from about 4 to about 5 EU/mL of composition.

In certain embodiments, otic compositions or devices described herein contain lower endotoxin levels (e.g. <0.5 EU/mL of composition) when compared to conventionally acceptable endotoxin levels (e.g., 0.5 EU/mL of composition). In some embodiments, the auris-acceptable otic therapeutic agent composition or device has less than about 0.5 EU/mL of composition. In other embodiments, the auris-acceptable otic therapeutic agent composition has less than about 0.4 EU/mL of composition. In additional embodiments, the auris-acceptable otic therapeutic agent composition has less than about 0.2 EU/mL of composition.

Pyrogen detection, by way of example only, is performed by several methods. Suitable tests for sterility include tests described in United States Pharmacopoeia (USP)<71> Sterility Tests (23rd edition, 1995). The rabbit pyrogen test and the *Limulus amebocyte* lysate test are both specified in the United States Pharmacopeia Chapters <85> and <151> (USP23/NF 18, Biological Tests, The United States Pharmacopeial Convention, Rockville, Md., 1995). Alternative pyrogen assays have been developed based upon the monocyte activation-cytokine assay. Uniform cell lines suitable for quality control applications have been developed and have demonstrated the ability to detect pyrogenicity in samples that have passed the rabbit pyrogen test and the *Limulus amebocyte* lysate test (Taktak et al, J. Pharm. Pharmacol. (1990), 43:578-82). In an additional embodiment, the auris-acceptable otic therapeutic agent composition is subject to depyrogenation. In a further embodiment, the process for the manufacture of the auris-acceptable otic therapeutic agent composition comprises testing the composition for pyrogenicity. In certain embodiments, the compositions described herein are substantially free of pyrogens.

pH and Practical Osmolarity

As used herein, "practical osmolarity/osmolality" or "deliverable osmolarity/osmolality" means the osmolarity/osmolality of a composition as determined by measuring the osmolarity/osmolality of the active agent and all excipients except the gelling and/or the thickening agent (e.g., polyoxyethylene-polyooxypropylene copolymers, carboxymethylcellulose or the like). The practical osmolarity of a composition described herein is measured by any suitable method, e.g., a freezing point depression method as described in Viegas et. al., *Int. J. Pharm.*, 1998, 160, 157-162. In some instances, the practical osmolarity of a composition described herein is measured by vapor pressure osmometry (e.g., vapor pressure depression method) that allows for determination of the osmolarity of a composition at higher temperatures. In some instances, vapor pressure depression method allows for determination of the osmolarity of a composition comprising a gelling agent (e.g., a thermoreversible polymer) at a higher temperature wherein the gelling agent is in the form of a gel. The practical osmolality of an otic composition described herein is from about 100 mOsm/kg to about 1000 mOsm/kg, from about 200 mOsm/kg to about 800 mOsm/kg, from about 250 mOsm/kg to about 500 mOsm/kg, or from about 250 mOsm/kg to about 320 mOsm/kg, or from about 250 mOsm/kg to about 350 mOsm/kg or from about 280 mOsm/kg to about 320 mOsm/kg. In some embodiments, the compositions described herein have a practical osmolarity of about 100 mOsm/L to about 1000 mOsm/L, about 200 mOsm/L to about 800 mOsm/L, about 250 mOsm/L to about 500 mOsm/L, about 250 mOsm/L to about 350 mOsm/L, about 250 mOsm/L to about 320 mOsm/L, or about 280 mOsm/L to about 320 mOsm/L.

In some embodiments, the osmolarity at a target site of action (e.g., the perilymph) is about the same as the delivered osmolarity (i.e., osmolarity of materials that cross or penetrate the round window membrane) of any composition described herein. In some embodiments, the compositions described herein have a deliverable osmolarity of about 150 mOsm/L to about 500 mOsm/L, about 250 mOsm/L to about 500 mOsm/L, about 250 mOsm/L to about 350 mOsm/L, about 280 mOsm/L to about 370 mOsm/L or about 250 mOsm/L to about 320 mOsm/L.

The main cation present in the endolymph is potassium. In addition the endolymph has a high concentration of positively charged amino acids. The main cation present in the perilymph is sodium. In certain instances, the ionic composition of the endolymph and perilymph regulate the electrochemical impulses of hair cells. In certain instances, any change in the ionic balance of the endolymph or perilymph results in a loss of hearing due to changes in the conduction of electrochemical impulses along otic hair cells. In some embodiments, a composition disclosed herein does not disrupt the ionic balance of the perilymph. In some embodiments, a composition disclosed herein has an ionic balance that is the same as or substantially the same as the perilymph. In some embodiments, a composition disclosed herein does not disrupt the ionic balance of the endolymph. In some embodiments, a composition disclosed herein has an ionic balance that is the same as or substantially the same as the endolymph. In some embodiments, an otic composition described herein is formulated to provide an ionic balance that is compatible with inner ear fluids (e.g., endolymph and/or perilymph).

The endolymph and the perilymph have a pH that is close to the physiological pH of blood. The endolymph has a pH range of about 7.2-7.9; the perilymph has a pH range of about 7.2-7.4. The in situ pH of the proximal endolymph is about 7.4 while the pH of distal endolymph is about 7.9.

In some embodiments, the pH of a composition described herein is adjusted (e.g., by use of a buffer) to an endolymph-compatible pH range of about 5.5 to 9.0. In specific embodiments, the pH of a composition described herein is adjusted to a perilymph-suitable pH range of about 5.5 to about 9.0. In some embodiments, the pH of a composition described herein is adjusted to a perilymph-suitable range of about 5.5 to about 8.0, about 6 to about 8.0 or about 6.6 to about 8.0. In some embodiments, the pH of a composition described herein is adjusted to a perilymph-suitable pH range of about 7.0-7.6.

In some embodiments, useful compositions also include one or more pH adjusting agents or buffering agents. Suitable pH adjusting agents or buffers include, but are not limited to acetate, bicarbonate, ammonium chloride, citrate, phosphate, pharmaceutically acceptable salts thereof and combinations or mixtures thereof.

In one embodiment, when one or more buffers are utilized in the compositions of the present disclosure, they are combined (e.g., with a pharmaceutically acceptable vehicle) and are present in the final composition (e.g., in an amount ranging from about 0.1% to about 20%, from about 0.5% to about 10%). In certain embodiments of the present disclosure, the amount of buffer included in the gel compositions are an amount such that the pH of the gel composition does not interfere with the body's natural buffering system.

In one embodiment, diluents are also used to stabilize compounds because they can provide a more stable environment. Salts dissolved in buffered solutions (that also can provide pH control or maintenance) are utilized as diluents in the art, including, but not limited to a phosphate buffered saline solution.

In some embodiments, any gel composition described herein has a pH that allows for sterilization (e.g., by filtration or aseptic mixing or heat treatment and/or autoclaving (e.g., terminal sterilization)) of a gel composition without degradation of the pharmaceutical agent or the polymers comprising the gel. In order to reduce hydrolysis and/or degradation of the otic agent and/or the gel polymer during sterilization, the buffer pH is designed to maintain pH of the composition in the 7-8 range during the process of sterilization (e.g., high temperature autoclaving).

In specific embodiments, any gel composition described herein has a pH that allows for terminal sterilization (e.g., by heat treatment and/or autoclaving) of a gel composition without degradation of the pharmaceutical agent or the polymers comprising the gel. For example, in order to reduce hydrolysis and/or degradation of the otic agent and/or the gel polymer during autoclaving, the buffer pH is designed to maintain pH of the composition in the 7-8 range at elevated temperatures. Any appropriate buffer is used depending on the otic agent used in the composition. In some instances, since $pK_a$ of TRIS decreases as temperature increases at approximately $-0.03/°$ C. and $pK_a$ of PBS increases as temperature increases at approximately $0.003/°$ C., autoclaving at 250° F. (121° C.) results in a significant downward pH shift (i.e. more acidic) in the TRIS buffer whereas a relatively much less upward pH shift in the PBS buffer and therefore much increased hydrolysis and/or degradation of an otic agent in TRIS than in PBS. Degradation of an otic agent is reduced by the use of an appropriate combination of a buffer and polymeric additives (e.g. P407, CMC) as described herein.

In some embodiments, a composition pH of between about 5.0 and about 9.0, between about 5.5 and about 8.5, between about 6.0 and about 7.6, between about 7 and about 7.8, between about 7.0 and about 7.6, between about 7.2 and 7.6, or between about 7.2 and about 7.4 is suitable for sterilization (e.g., by filtration or aseptic mixing or heat treatment and/or autoclaving (e.g., terminal sterilization)) of auris compositions described herein. In specific embodiments a composition pH of about 6.0, about 6.5, about 7.0, about 7.1, about 7.2, about 7.3, about 7.4, about 7.5, or about 7.6 is suitable for sterilization (e.g., by filtration or aseptic mixing or heat treatment and/or autoclaving (e.g., terminal sterilization)) of any composition described herein.

In some embodiments, the compositions have a pH as described herein, and include a thickening agent (e.g., a viscosity enhancing agent) such as, by way of non-limiting example, a cellulose based thickening agent described herein. In some instances, the addition of a secondary polymer (e.g., a thickening agent) and a pH of composition as described herein, allows for sterilization of a composition described herein without any substantial degradation of the otic agent and/or the polymer components in the otic composition. In some embodiments, the ratio of a thermoreversible poloxamer to a thickening agent in a composition that has a pH as described herein, is about 40:1, about 35:1, about 30:1, about 25:1, about 20:1, about 15:1 about 10:1, or about 5:1. For example, in certain embodiments, a sustained and/or extended release composition described herein comprises a combination of poloxamer 407 (pluronic F127) and carboxymethylcellulose (CMC) in a ratio of about 40:1, about 35:1, about 30:1, about 25:1, about 20:1, about 15:1, about 10:1 or about 5:1.

In some embodiments, the amount of thermoreversible polymer in any composition described herein is about 10%, about 15%, about 20%, about 25%, about 30%, about 35% or about 40% of the total weight of the composition. In some embodiments, the amount of thermoreversible polymer in any composition described herein is about 10%, about 11%, about 12%, about 13%, about 14%, about 15%, about 16%, about 17%, about 18%, about 19%, about 20%, about 21%, about 22%, about 23%, about 24% or about 25% of the total weight of the composition. In some embodiments, the amount of thermoreversible polymer (e.g., pluronic F127) in any composition described herein is about 7.5% of the total weight of the composition. In some embodiments, the amount of thermoreversible polymer (e.g., pluronic F127) in any composition described herein is about 10% of the total weight of the composition. In some embodiments, the amount of thermoreversible polymer (e.g., pluronic F127) in any composition described herein is about 11% of the total weight of the composition. In some embodiments, the amount of thermoreversible polymer (e.g., pluronic F127) in any composition described herein is about 12% of the total weight of the composition. In some embodiments, the amount of thermoreversible polymer (e.g., pluronic F127) in any composition described herein is about 13% of the total weight of the composition. In some embodiments, the amount of thermoreversible polymer (e.g., pluronic F127) in any composition described herein is about 14% of the total weight of the composition. In some embodiments, the amount of thermoreversible polymer (e.g., pluronic F127) in any composition described herein is about 15% of the total weight of the composition. In some embodiments, the amount of thermoreversible polymer (e.g., pluronic F127) in any composition described herein is about 16% of the total weight of the composition. In some embodiments, the amount of thermoreversible polymer (e.g., pluronic F127) in any composition described herein is about 17% of the total weight of the composition. In some embodiments, the amount of thermoreversible polymer (e.g., pluronic F127) in any composition described herein is about 18% of the total weight of the composition. In some embodiments, the amount of thermoreversible polymer (e.g., pluronic F127) in any composition described herein is about 19% of the total weight of the composition. In some embodiments, the amount of thermoreversible polymer (e.g., pluronic F127) in any composition described herein is about 20% of the total weight of the composition. In some embodiments, the amount of thermoreversible polymer (e.g., pluronic F127) in any composition described herein is about 21% of the total weight of the composition. In some embodiments, the amount of thermoreversible polymer (e.g., pluronic F127) in any composition described herein is about 23% of the total weight of the composition. In some embodiments, the amount of thermoreversible polymer (e.g., pluronic F127) in any composition described herein is about 25% of the total weight of the composition.

In some embodiments, the amount of thickening agent (e.g., a gelling agent) in any composition described herein is about 1%, about 5%, about 10%, or about 15% of the total weight of the composition. In some embodiments, the amount of thickening agent (e.g., a gelling agent) in any composition described herein is about 0.5%, about 1%, about 1.5%, about 2%, about 2.5%, about 3%, about 3.5%, about 4%, about 4.5%, or about 5% of the total weight of the composition.

In some embodiments, the pharmaceutical compositions described herein are stable with respect to pH over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 1 month, at least about 2 months, at least about 3 months, at least about 4 months, at least about 5 months, or at least about 6 months. In other embodiments, the compositions described herein are stable with respect to pH over a period of at least about 1 week. Also described herein are compositions that are stable with respect to pH over a period of at least about 1 month.

Tonicity Agents

In general, the endolymph has a higher osmolality than the perilymph. For example, the endolymph has an osmolality of about 304 mOsm/kg $H_2O$ while the perilymph has an osmolality of about 294 mOsm/kg $H_2O$. In certain embodiments, tonicity agents are added to the compositions described herein in an amount as to provide a practical osmolality of an otic composition of about 100 mOsm/kg to about 1000 mOsm/kg, from about 200 mOsm/kg to about 800 mOsm/kg, from about 250 mOsm/kg to about 500 mOsm/kg, or from about 250 mOsm/kg to about 350 mOsm/kg or from about 280 mOsm/kg to about 320 mOsm/kg. In some embodiments, the compositions described herein have a practical osmolarity of about 100 mOsm/L to about 1000 mOsm/L, about 200 mOsm/L to about 800 mOsm/L, about 250 mOsm/L to about 500 mOsm/L, about 250 mOsm/L to about 350 mOsm/L, about 280 mOsm/L to about 320 mOsm/L or about 250 mOsm/L to about 320 mOsm/L.

In some embodiments, the deliverable osmolarity of any composition described herein is designed to be isotonic with the targeted otic structure (e.g., endolymph, perilymph or the like). In specific embodiments, auris compositions described herein are formulated to provide a delivered perilymph-suitable osmolarity at the target site of action of about 250 to about 320 mOsm/L (osmolality of about 250 to about 320 mOsm/kg H₂O); and preferably about 270 to about 320 mOsm/L (osmolality of about 270 to about 320 mOsm/kg H₂O). In specific embodiments, the deliverable osmolarity/ osmolality of the compositions (i.e., the osmolarity/osmolality of the composition in the absence of gelling or thickening agents (e.g., thermoreversible gel polymers)) is adjusted, for example, by the use of appropriate salt concentrations (e.g., concentration of potassium or sodium salts) or the use of tonicity agents that renders the compositions endolymph-compatible and/or perilymph-compatible (i.e. isotonic with the endolymph and/or perilymph) upon delivery at the target site. The osmolarity of a composition comprising a thermoreversible gel polymer is an unreliable measure due to the association of varying amounts of water with the monomeric units of the polymer. The practical osmolarity of a composition is a reliable measure and is measured by any suitable method (e.g., freezing point depression method, vapor depression method). In some instances, the compositions described herein provide a deliverable osmolarity (e.g., at a target site (e.g., perilymph)) that causes minimal disturbance to the environment of the inner ear and causes minimum discomfort (e.g., vertigo and/or nausea) to a mammal upon administration.

In some embodiments, any composition described herein is isotonic with the perilymph and/or endolymph. Isotonic compositions are provided by the addition of a tonicity agent. Suitable tonicity agents include, but are not limited to any pharmaceutically acceptable sugar, salt or any combinations or mixtures thereof, such as, but not limited to dextrose, glycerin, mannitol, sorbitol, sodium chloride, and other electrolytes.

Useful auris compositions include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some embodiments, the compositions described herein have a pH and/or practical osmolarity as described herein, and have a concentration of active pharmaceutical ingredient between about 1 µM and about 10 µM, between about 1 mM and about 100 mM, between about 0.1 mM and about 100 mM, between about 0.1 mM and about 100 nM. In some embodiments, the compositions described herein have a pH and/or practical osmolarity as described herein, and have a concentration of active pharmaceutical ingredient between about 0.01%-about 20%, between about 0.01%-about 10%, between about 0.01%-about 7.5%, between about 0.01%-6%, between about 0.01-5%, between about 0.1-about 10%, or between about 0.1-about 6% of the active ingredient by weight of the composition. In some embodiments, the compositions described herein have a pH and/or practical osmolarity as described herein, and have a concentration of active pharmaceutical ingredient between about 0.1 and about 70 mg, between about 1 mg and about 70 mg/mL, between about 1 mg and about 50 mg/mL, between about 1 mg/mL and about 20 mg/mL, between about 1 mg/mL to about 10 mg/mL, between about 1 mg/mL to about 5 mg/mL, or between about 0.5 mg/mL to about 5 mg/mL of the active agent by volume of the composition. In some embodiments, the compositions described herein have a pH and/or practical osmolarity as described herein, and have a concentration of active pharmaceutical ingredient between about 1 µg/mL and about 500 µg/mL, between about 1 µg/mL and about 250 µg/mL, between about 1 µg and about 100 µg/mL, between about 1 µg/mL and about 50 µg/mL, or between about 1 µg/mL and about 20 µg/mL of the active agent by volume of the composition.

Particle Size

Size reduction is used to increase surface area and/or modulate composition dissolution properties. It is also used to maintain a consistent average particle size distribution (PSD) (e.g., micrometer-sized particles, nanometer-sized particles or the like) for any composition described herein. In some embodiments, any composition described herein is multiparticulate (i.e., comprises a plurality of particle sizes (e.g., micronized particles, nano-sized particles, non-sized particles, colloidal particles)). In some embodiments, any composition described herein comprises one or more multiparticulate (e.g., micronized) therapeutic agents. Micronization is a process of reducing the average diameter of particles of a solid material. Micronized particles are from about micrometer-sized in diameter to about nanometer-sized in diameter. In some embodiments, the average diameter of particles in a micronized solid is from about 0.5 µm to about 500 µm. In some embodiments, the average diameter of particles in a micronized solid is from about 1 µm to about 200 µm. In some embodiments, the average diameter of particles in a micronized solid is from about 2 µm to about 100 µm. In some embodiments, the average diameter of particles in a micronized solid is from about 3 µm to about 50 µm. In some embodiments, a particulate micronized solid comprises'particle sizes of less than about 5 microns, less than about 20 micron's and/or less than about 100 microns. In some embodiments, the use of particulates (e.g., micronized particles) of a CNS modulating agent allows for extended and/or sustained release of the CNS modulating agent from any composition described herein compared to a composition comprising non-multiparticulate (e.g., non-micronized) CNS modulating agent. In some instances, compositions containing multiparticulate (e.g. micronized) CNS modulating agent are ejected from a 1 mL syringe adapted with a 27 G needle without any plugging or clogging.

In some instances, any particle in any composition described herein is a coated particle (e.g., a coated micronized particle, nano-particle) and/or a microsphere and/or a liposomal particle. Particle size reduction techniques include, by way of example, grinding, milling (e.g., air-attrition milling (jet milling), ball milling), coacervation, complex coacervation, high pressure homogenization, spray drying and/or supercritical fluid crystallization. In some instances, particles are sized by mechanical impact (e.g., by hammer mills, ball mill and/or pin mills). In some instances, particles are sized via fluid energy (e.g., by spiral jet mills, loop jet mills, and/or fluidized bed jet mills). In some embodiments, compositions described herein comprise crystalline particles and/or isotropic particles. In some embodiments, compositions described herein comprise amorphous particles and/or anisotropic particles. In some embodiments, compositions described herein comprise therapeutic agent particles wherein the therapeutic agent is a neutral molecule, a free acid, a free base, or a salt, or a prodrug of a therapeutic agent, or any combination thereof.

In some embodiments, a composition described herein comprises one or more CNS modulating agents wherein the CNS modulating agent comprises nanoparticulates. In some embodiments, a composition described herein comprises CNS modulating agent beads (e.g., tacrolimus beads) that are optionally coated with controlled-release excipients. In some embodiments, a composition described herein comprises a CNS modulating agent that is granulated and/or reduced in size and coated with controlled-release excipients; the granulated coated CNS modulating agent particulates are then optionally micronized and/or formulated in any of the compositions described herein.

In some instances, a combination of a CNS modulating agent as a neutral molecule, a free acid, a free base and a salt of the CNS modulating agent is used to prepare pulsed release otic agent compositions using the procedures described herein. In some compositions, a combination of a micronized CNS modulating agent (and/or salt or prodrug thereof) and coated particles (e.g., nanoparticles, liposomes, microspheres) is used to prepare pulsed release otic agent compositions using any procedure described herein. Alternatively, a pulsed release profile is achieved by solubilizing up to 20% of the delivered dose of the CNS modulating agent (e.g., micronized CNS modulating agent, a neutral molecule, free base, free acid or salt or prodrug thereof; multiparticulate CNS modulating agent, a neutral molecule, a free base, free acid or salt or prodrug thereof) with the aid of cyclodextrins, surfactants (e.g., poloxamers (407, 338, 188), tween (80, 60, 20, 81), PEG-hydrogenated castor oil, cosolvents like N-methyl-2-Pyrrolidone or the like and preparing pulsed release compositions using any procedure described herein.

In specific embodiments, any auris-compatible composition described herein comprises one or more micronized pharmaceutical agents (e.g., CNS modulating agents). In some of such embodiments, a micronized pharmaceutical agent comprises micronized particles, coated (e.g., with an extended release coat) micronized particles, or a combination thereof. In some of such embodiments, a micronized pharmaceutical agent comprising micronized particles, coated micronized particles, or a combination thereof, comprises a CNS modulating agent as a neutral molecule, a free acid, a free base, a salt, a prodrug or any combination thereof. In certain embodiments, a pharmaceutical composition described herein comprises a CNS modulating agent as a micronized powder.

The multiparticulates and/or micronized CNS modulating agents described herein are delivered to an auris structure (e.g., inner ear) by means of any type of matrix including solid, liquid or gel matrices. In some embodiments, the multiparticulates and/or micronized CNS modulating agents described herein are delivered to an auris structure (e.g., inner ear) by means of any type of matrix including solid, liquid or gel matrices via intratympanic injection.

Pharmaceutical Compositions

Provided herein are pharmaceutical compositions or devices that include at least one CNS modulating agent and a pharmaceutically acceptable diluent(s), excipient(s), or carrier(s). In some embodiments, the pharmaceutical compositions include other medicinal or pharmaceutical agents, carriers, adjuvants, such as preserving, stabilizing, wetting or emulsifying agents, solution promoters, salts for regulating the osmotic pressure, and/or buffers. In other embodiments, the pharmaceutical compositions also contain other therapeutic substances.

Some pharmaceutical excipients, diluents or carriers are potentially ototoxic. For example, benzalkonium chloride, a common preservative, is ototoxic and therefore potentially harmful if introduced into the vestibular or cochlear structures. In formulating a controlled-release CNS modulating composition, it is advised to avoid or combine the appropriate excipients, diluents or carriers to lessen or eliminate potential ototoxic components from the composition, or to decrease the amount of such excipients, diluents or carriers. Optionally, a controlled-release CNS modulating composition includes otoprotective agents, such as antioxidants, alpha lipoic acid, calcium, fosfomycin or iron chelators, to counteract potential ototoxic effects that may arise from the use of specific therapeutic agents or excipients, diluents or carriers.

In some embodiments, the compositions or devices described herein include a dye to help enhance the visualization of the gel when applied. In some embodiments, dyes that are compatible with the auris-acceptable compositions or devices described herein include Evans blue (e.g., 0.5% of the total weight of an otic composition), Methylene blue (e.g., 1% of the total weight of an otic composition), Isosulfan blue (e.g., 1% of the total weight of an otic composition), Trypan blue (e.g., 0.15% of the total weight of an otic composition), and/or indocyanine green (e.g., 25 mg/vial). Other common dyes, e.g., FD&C red 40, FD&C red 3, FD&C yellow 5, FD&C yellow 6, FD&C blue 1, FD&C blue 2, FD&C green 3, fluorescence dyes (e.g., Fluorescein isothiocyanate, rhodamine, Alexa Fluors, DyLight Fluors) and/or dyes that are visualizable in conjunction with non-invasive imaging techniques such as MRI, CAT scans, PET scans or the like. Gadolinium-based MRI dyes, iodine-base dyes, barium-based dyes or the like are also contemplated for use with any otic composition described herein. Other dyes that are compatible with any composition or composition described herein are listed in the Sigma-Aldrich catalog under dyes (that is included herein by reference for such disclosure).

Any pharmaceutical composition or device described herein is administered by locating the composition or device in contact with the crista fenestrae cochlea, the round window, the tympanic cavity, the tympanic membrane, the auris media or the auris externa.

In one specific embodiment of the auris-acceptable controlled-release CNS modulating agent pharmaceutical compositions described herein, the CNS modulating agent is provided in a gel matrix, also referred to herein as "auris acceptable gel compositions," "auris interna-acceptable gel compositions," "auris media-acceptable gel compositions," "auris externa-acceptable gel compositions", "auris gel compositions" or variations thereof. All of the components of the gel composition must be compatible with the targeted auris structure. Further, the gel compositions provide controlled-release of the CNS modulating agent to the desired site within the targeted auris structure; in some embodiments, the gel composition also has an immediate or rapid release component for delivery of the CNS modulating agent to the desired target site. In other embodiments, the gel composition has a sustained release component for delivery of the CNS modulating agent. In some embodiments, the gel composition comprises a multiparticulate (e.g., micronized) CNS modulating agent. In some embodiments, the auris gel compositions are biodegradable. In other embodiments, the auris gel compositions include a mucoadhesive excipient to allow adhesion to the external mucous layer of the round window membrane. In yet other embodiments, the auris gel compositions include a penetration enhancer excipient; in further embodiments, the auris gel composition contains a viscosity enhancing agent sufficient to provide a viscosity of between about 500 and 1,000,000 centipoise, between about 750 and 1,000,000 centipoise; between about 1000 and 1,000,000 centipoise; between about 1000 and 400,000 centipoise; between about 2000 and 100,000 centipoise; between about 3000 and 50,000 centipoise; between about 4000 and 25,000 centipoise; between about 5000 and 20,000 centipoise; or between about 6000 and 15,000 centipoise. In some embodiments, the auris gel composition contains a viscosity enhancing agent sufficient to provide a viscosity of between about 50,0000 and 1,000,000 centipoise.

In other embodiments, the auris interna pharmaceutical compositions described herein further provide an auris-acceptable hydrogel; in yet other embodiments, the auris pharmaceutical compositions provide an auris-acceptable microsphere or microparticle; in still other embodiments, the auris pharmaceutical compositions provide an auris-acceptable liposome. In some embodiments, the auris pharmaceutical compositions provide an auris-acceptable foam; in yet other embodiments, the auris pharmaceutical compositions provide an auris-acceptable paint; in still further embodiments, the auris pharmaceutical compositions provide an auris-acceptable in situ forming spongy material. In some embodiments, the auris pharmaceutical compositions provide an auris-acceptable solvent release gel. In some embodiments, the auris pharmaceutical compositions provide an actinic radiation curable gel. Further embodiments include a thermoreversible gel in the auris pharmaceutical composition, such that upon preparation of the gel at room temperature or below, the composition is a fluid, but upon application of the gel into or near the auris interna and/or auris media target site, including the tympanic cavity, round window membrane or the crista fenestrae cochleae, the auris-pharmaceutical composition stiffens or hardens into a gel-like substance.

In further or alternative embodiments, the auris gel compositions are capable of being administered on or near the round window membrane via intratympanic injection. In other embodiments, the auris gel compositions are administered on or near the round window or the crista fenestrae cochleae through entry via a post-auricular incision and surgical manipulation into or near the round window or the crista fenestrae cochleae area. Alternatively, the auris gel composition is applied via syringe and needle, wherein the needle is inserted through the tympanic membrane and guided to the area of the round window or crista fenestrae cochleae. The auris gel compositions are then deposited on or near the round window or crista fenestrae cochleae for localized treatment. In other embodiments, the auris gel compositions are applied via microcatheters implanted into the patient, and in yet further embodiments the compositions are administered via a pump device onto or near the round window membrane. In still further embodiments, the auris gel compositions are applied at or near the round window membrane via a microinjection device. In yet other embodiments, the auris gel compositions are applied in the tympanic cavity. In some embodiments, the auris gel compositions are applied on the tympanic membrane. In still other embodiments, the auris gel compositions are applied onto or in the auditory canal.

In further specific embodiments, any pharmaceutical composition or device described herein comprises a multiparticulate CNS modulating agent in a liquid matrix (e.g., a liquid composition for intratympanic injection, or otic drops). In certain embodiments, any pharmaceutical composition described herein comprises a multiparticulate CNS modulating agent in a solid matrix.

Controlled-Release Compositions

In general, controlled-release drug compositions impart control over the release of drug with respect to site of release and time of release within the body. As discussed herein, controlled-release refers to immediate release, delayed release, sustained release, extended release, variable release, pulsatile release and bi-modal release. Many advantages are offered by controlled-release. First, controlled-release of a pharmaceutical agent allows less frequent dosing and thus minimizes repeated treatment. Second, controlled-release treatment results in more efficient drug utilization and less of the compound remains as a residue. Third, controlled-release offers the possibility of localized drug delivery by placement of a delivery device or composition at the site of disease. Still further, controlled-release offers the opportunity to administer and release two or more different drugs, each having a unique release profile, or to release the same drug at different rates or for different durations, by means of a single dosage unit.

Accordingly, one aspect of the embodiments disclosed herein is to provide a controlled-release CNS modulating auris-acceptable composition or. The controlled-release aspect of the compositions and/or compositions and/or devices disclosed herein is imparted through a variety of agents, including but not limited to excipients, agents or materials that are acceptable for use in the auris interna or other otic structure. By way of example only, such excipients, agents or materials include an auris-acceptable polymer, an auris-acceptable viscosity enhancing agent, an auris-acceptable gel, an auris-acceptable paint, an auris-acceptable foam, an auris-acceptable xerogel, an auris-acceptable microsphere or microparticle, an auris-acceptable hydrogel, an auris-acceptable in situ forming spongy material, an auris-acceptable actinic radiation curable gel, an auris-acceptable solvent release gel, an auris-acceptable liposome, an auris-acceptable nanocapsule or nanosphere, an auris-acceptable thermoreversible gel, or combinations thereof.

Auris-Acceptable Gels

Gels, sometimes referred to as jellies, have been defined in various ways. For example, the United States Pharmacopoeia defines gels as semisolid systems consisting of either suspensions made up of small inorganic particles or large organic molecules interpenetrated by a liquid. Gels include a single-phase or a two-phase system. A single-phase gel consists of organic macromolecules distributed uniformly throughout a liquid in such a manner that no apparent boundaries exist between the dispersed macromolecules and the liquid. Some single-phase gels are prepared from synthetic macromolecules (e.g., carbomer) or from natural gums, (e.g., tragacanth). In some embodiments, single-phase gels are generally aqueous, but will also be made using alcohols and oils. Two-phase gels consist of a network of small discrete particles.

Gels can also be classified as being hydrophobic or hydrophilic. In certain embodiments, the base of a hydrophobic gel consists of a liquid paraffin with polyethylene or fatty oils gelled with colloidal silica, or aluminum or zinc soaps. In contrast, the base of hydrophobic gels usually consists of water, glycerol, or propylene glycol gelled with a suitable gelling agent (e.g., tragacanth, starch, cellulose derivatives, carboxyvinylpolymers, and magnesium-aluminum silicates). In certain embodiments, the rheology of the compositions or devices disclosed herein is pseudo plastic, plastic, thixotropic, or dilatant.

In one embodiment the enhanced viscosity auris-acceptable composition described herein is not a liquid at room temperature. In certain embodiments, the enhanced viscosity composition is characterized by a phase transition between room temperature and body temperature (including an individual with a serious fever, e.g., up to about 42° C.). In some embodiments, the phase transition occurs at 1° C. below body temperature, at 2° C. below body temperature, at 3° C. below body temperature, at 4° C. below body temperature, at 6° C. below body temperature, at 8° C. below body temperature, or at 10° C. below body temperature. In some embodiments, the phase transition occurs at about 15° C. below body temperature, at about 20° C. below body temperature or at about 25° C. below body temperature. In specific embodiments, the gelation temperature (Tgel) of a composition described herein is about 20° C., about 25° C., or about 30° C. In certain embodiments, the gelation temperature (Tgel) of a composition described herein is about 35° C., or about 40° C. In one embodiment, administration of any composition described herein at about body temperature reduces or inhibits vertigo associated with intratympanic administration of otic compositions. Included within the definition of body temperature is the body temperature of a healthy individual, or an unhealthy individual, including an individual with a fever (up to ~42° C.)). In some embodiments, the pharmaceutical compositions or devices described herein are liquids at about room temperature and are administered at or about room temperature, reducing or ameliorating side effects such as, for example, vertigo.

Polymers composed of polyoxypropylene and polyoxyethylene form thermoreversible gels when incorporated into aqueous solutions. These polymers have the ability to change from the liquid state to the gel state at temperatures close to body temperature, therefore allowing useful compositions that are applied to the targeted auris structure(s). The liquid state-to-gel state phase transition is dependent on the polymer concentration and the ingredients in the solution.

Poloxamer 407 (PF-127) is a nonionic surfactant composed of polyoxyethylene-polyoxypropylene copolymers. Other poloxamers include 188 (F-68 grade), 237 (F-87 grade), 338 (F-108 grade). Aqueous solutions of poloxamers are stable in the presence of acids, alkalis, and metal ions. PF-127 is a commercially available polyoxyethylene-polyoxypropylene triblock copolymer of general formula E106 P70 E106, with an average molar mass of 13,000. The polymer can be further purified by suitable methods that will enhance gelation properties of the polymer. It contains approximately 70% ethylene oxide, which accounts for its hydrophilicity. It is one of the series of poloxamer ABA block copolymers, whose members share the chemical formula shown below.

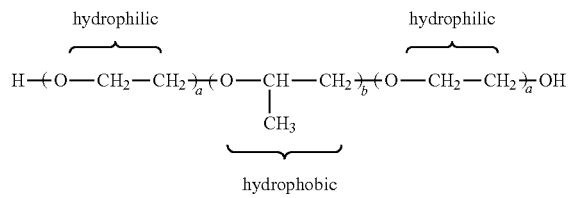

PF-127 is of particular interest since concentrated solutions (>20% w/w) of the copolymer are transformed from low viscosity transparent solutions to solid gels on heating to body temperature. This phenomenon, therefore, suggests that when placed in contact with the body, the gel preparation will form a semi-solid structure and a sustained release depot. Furthermore, PF-127 has good solubilizing capacity, low toxicity and is, therefore, considered a good medium for drug delivery systems.

In an alternative embodiment, the thermogel is a PEG-PLGA-PEG triblock copolymer (Jeong et al, Nature (1997), 388:860-2; Jeong et al, J. Control. Release (2000), 63:155-63; Jeong et al, Adv. Drug Delivery Rev. (2002), 54:37-51). The polymer exhibits sol-gel behavior over a concentration of about 5% w/w to about 40% w/w. Depending on the properties desired, the lactide/glycolide molar ratio in the PLGA copolymer ranges from about 1:1 to about 20:1. The resulting copolymers are soluble in water and form a free-flowing liquid at room temperature, but form a hydrogel at body temperature. A commercially available PEG-PLGA-PEG triblock copolymer is RESOMER RGP t50106 manufactured by Boehringer Ingelheim. This material is composed of a PGLA copolymer of 50:50 poly(DL-lactide-co-glycolide) and is 10% w/w of PEG and has a molecular weight of about 6000.

ReGel® is a tradename of MacroMed Incorporated for a class of low molecular weight, biodegradable block copolymers having reverse thermal gelation properties as described in U.S. Pat. Nos. 6,004,573, 6,117,949, 6,201,072, and 6,287,588. It also includes biodegradable polymeric drug carriers disclosed in pending U.S. patent application Ser. Nos. 09/906,041, 09/559,799 and 10/919,603. The biodegradable drug carrier comprises ABA-type or BAB-type triblock copolymers or mixtures thereof, wherein the A-blocks are relatively hydrophobic and comprise biodegradable polyesters or poly (orthoester)s, and the B-blocks are relatively hydrophilic and comprise polyethylene glycol (PEG), said copolymers having a hydrophobic content of between 50.1 to 83% by weight and a hydrophilic content of between 17 to 49.9% by weight, and an overall block copolymer molecular weight of between 2000 and 8000 Daltons. The drug carriers exhibit water solubility at temperatures below normal mammalian body temperatures and undergo reversible thermal gelation to then exist as a gel at temperatures equal to physiological mammalian body temperatures. The biodegradable, hydrophobic A polymer block comprises a polyester or poly(ortho ester), in that the polyester is synthesized from monomers selected from the group consisting of D,L-lactide, D-lactide, L-lactide, D,L-lactic acid, D-lactic acid, L-lactic acid, glycolide, glycolic acid, ε-caprolactone, ε-hydroxyhexanoic acid, γ-butyrolactone, γ-hydroxybutyric acid, δ-valerolactone, δ-hydroxyvaleric acid, hydroxybutyric acids, malic acid, and copolymers thereof and having an average molecular weight of between about 600 and 3000 Daltons. The hydrophilic B-block segment is preferably polyethylene glycol (PEG) having an average molecular weight of between about 500 and 2200 Daltons.

Additional biodegradable thermoplastic polyesters include AtriGel® (provided by Atrix Laboratories, Inc.) and/or those disclosed, e.g., in U.S. Pat. Nos. 5,324,519; 4,938,763; 5,702,716; 5,744,153; and 5,990,194; wherein the suitable biodegradable thermoplastic polyester is disclosed as a thermoplastic polymer. Examples of suitable biodegradable thermoplastic polyesters include polylactides, polyglycolides, polycaprolactones, copolymers thereof, terpolymers thereof, and any combinations thereof. In some such embodiments, the suitable biodegradable thermoplastic polyester is a polylactide, a polyglycolide, a copolymer thereof, a terpolymer thereof, or a combination thereof. In one embodiment, the biodegradable thermoplastic polyester is 50/50 poly(DL-lactide-co-glycolide) having a carboxy terminal group; is present in about 30 wt. % to about 40 wt. % of the composition; and has an average molecular weight of about 23,000 to about 45,000. Alternatively, in another embodiment, the biodegradable thermoplastic polyester is 75/25 poly (DL-lactide-co-glycolide) without a carboxy terminal group; is present in about 40 wt. % to about 50 wt. % of the composition; and has an average molecular weight of about 15,000 to about 24,000. In further or alternative embodiments, the terminal groups of the poly(DL-lactide-co-glycolide) are either hydroxyl, carboxyl, or ester depending upon the method of polymerization. Polycondensation of lactic or glycolic acid provides a polymer with terminal hydroxyl and carboxyl groups. Ring-opening polymerization of the cyclic lactide or glycolide monomers with water, lactic acid, or glycolic acid provides polymers with the same terminal groups. However, ring-opening of the cyclic monomers with a monofunctional alcohol such as methanol, ethanol, or 1-dodecanol provides a polymer with one hydroxyl group and one ester terminal groups. Ring-opening polymerization of the cyclic monomers with a diol such as 1,6-hexanediol or polyethylene glycol provides a polymer with only hydroxyl terminal groups.

Since the polymer systems of thermoreversible gels dissolve more completely at reduced temperatures, methods of solubilization include adding the required amount of polymer to the amount of water to be used at reduced temperatures. Generally after wetting the polymer by shaking, the mixture is capped and placed in a cold chamber or in a thermostatic container at about 0-10° C. in order to dissolve the polymer. The mixture is stirred or shaken to bring about a more rapid dissolution of the thermoreversible gel polymer. The CNS modulating agent and various additives such as buffers, salts, and preservatives are subsequently added and dissolved. In some instances the CNS modulating agent and/or other pharmaceutically active agent is suspended if it is insoluble in water. The pH is modulated by the addition of appropriate buffering agents, round window membrane mucoadhesive characteristics are optionally imparted to a thermoreversible gel by incorporation of round window membrane mucoadhesive carbomers, such as Carbopol® 934P, to the composition (Majithiya et al, AAPS PharmSciTech (2006), 7(3), p. E1; EP0551626, both of that is incorporated herein by reference for such disclosure).

In one embodiment are auris-acceptable pharmaceutical gel compositions that do not require the use of an added viscosity enhancing agent. Such gel compositions incorporate at least one pharmaceutically acceptable buffer. In one aspect is a gel composition comprising a CNS modulating agent and a pharmaceutically acceptable buffer. In another embodiment, the pharmaceutically acceptable excipient or carrier is a gelling agent.

In other embodiments, useful CNS modulating agent auris-acceptable pharmaceutical compositions also include one or more pH adjusting agents or buffering agents to provide an endolymph or perilymph suitable pH. Suitable pH adjusting agents or buffers include, but are not limited to acetate, bicarbonate, ammonium chloride, citrate, phosphate, pharmaceutically acceptable salts thereof and combinations or mixtures thereof. Such pH adjusting agents and buffers are included in an amount required to maintain pH of the composition between a pH of about 5 and about 9, in one embodiment a pH between about 6.5 to about 7.5, and in yet another embodiment at a pH of about 6.5, 6.6, 6.7, 6.8, 6.9, 7.0, 7.1, 7.2, 7.3, 7.4, 7.5. In one embodiment, when one or more buffers are utilized in the compositions of the present disclosure, they are combined, e.g., with a pharmaceutically acceptable vehicle and are present in the final composition, e.g., in an amount ranging from about 0.1% to about 20%, from about 0.5% to about 10%. In certain embodiments of the present disclosure, the amount of buffer included in the gel compositions is an amount such that the pH of the gel composition does not interfere with the natural buffering system of the auris media or auris interna, or does not interfere with the natural pH of the endolymph or perilymph: depending on where in the cochlea the CNS modulating agent composition is targeted. In some embodiments, from about 10 µM to about 200 mM concentration of a buffer is present in the gel composition. In certain embodiments, from about a 5 mM to about a 200 mM concentration of a buffer is present. In certain embodiments, from about a 20 mM to about a 100 mM concentration of a buffer is present. In one embodiment is a buffer such as acetate or citrate at slightly acidic pH. In one embodiment the buffer is a sodium acetate buffer having a pH of about 4.5 to about 6.5. In one embodiment the buffer is a sodium citrate buffer having a pH of about 5.0 to about 8.0, or about 5.5 to about 7.0.

In an alternative embodiment, the buffer used is tris(hydroxymethyl)aminomethane, bicarbonate, carbonate or phosphate at slightly basic pH. In one embodiment, the buffer is a sodium bicarbonate buffer having a pH of about 6.5 to about 8.5, or about 7.0 to about 8.0. In another embodiment the buffer is a sodium phosphate dibasic buffer having a pH of about 6.0 to about 9.0.

Also described herein are controlled-release compositions or devices comprising a CNS modulating agent and a viscosity enhancing agent. Suitable viscosity-enhancing agents include by way of example only, gelling agents and suspending agents. In one embodiment, the enhanced viscosity composition does not include a buffer. In other embodiments, the enhanced viscosity composition includes a pharmaceutically acceptable buffer. Sodium chloride or other tonicity agents are optionally used to adjust tonicity, if necessary.

By way of example only, the auris-acceptable viscosity agent include hydroxypropyl methylcellulose, hydroxyethyl cellulose, polyvinylpyrrolidone, carboxymethyl cellulose, polyvinyl alcohol, sodium chondroitin sulfate, sodium hyaluronate. Other viscosity enhancing agents compatible with the targeted auris structure include, but are not limited to, acacia (gum arabic), agar, aluminum magnesium silicate, sodium alginate, sodium stearate, bladderwrack, bentonite, carbomer, carrageenan, Carbopol, xanthan, cellulose, microcrystalline cellulose (MCC), ceratonia, chitin, carboxymethylated chitosan, chondrus, dextrose, furcellaran, gelatin, Ghatti gum, guar gum, hectorite, lactose, sucrose, maltodextrin, mannitol, sorbitol, honey, maize starch, wheat starch, rice starch, potatb starch, gelatin, sterculia gum, xanthum gum, gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly (methoxyethyl methacrylate), poly(methoxyethoxyethyl methacrylate), hydroxypropyl cellulose, hydroxypropylmethyl-cellulose (HPMC), sodium carboxymethyl-cellulose (CMC), silicon dioxide, polyvinylpyrrolidone (PVP: povidone), Splenda® (dextrose, maltodextrin and sucralose) or combinations thereof. In specific embodiments, the viscosity-enhancing excipient is a combination of MCC and CMC. In another embodiment, the viscosity-enhancing agent is a combination of carboxymethylated chitosan, or chitin, and alginate. The combination of chitin and alginate with the CNS modulating agents disclosed herein acts as a controlled-release composition, restricting the diffusion of the CNS modulating agents from the composition. Moreover, the combination of carboxymethylated chitosan and alginate is optionally used to assist in increasing the permeability of the CNS modulating agents through the round window membrane.

In some embodiments, is an enhanced viscosity composition, comprising from about 0.1 mM and about 100 mM of a CNS modulating agent, a pharmaceutically acceptable viscosity agent, and water for injection, the concentration of the viscosity agent in the water being sufficient to provide a enhanced viscosity composition with a final viscosity from about 100 to about 100,000 cP. In certain embodiments, the viscosity of the gel is in the range from about 100 to about 50,000 cP, about 100 cP to about 1,000 cP, about 500 cP to about 1500 cP, about 1000 cP to about 3000 cP, about 2000 cP to about 8,000 cP, about 4,000 cP to about 50,000 cP, about 10,000 cP to about 500,000 cP, about 15,000 cP to about 1,000,000 cP. In other embodiments, when an even more viscous medium is desired, the biocompatible gel comprises at least about 35%, at least about 45%, at least about 55%, at least about 65%, at least about 70%, at least about 75%, or even at least about 80% or so by weight of the CNS modulating agent. In highly concentrated samples, the biocompatible enhanced viscosity composition comprises at least about 25%, at least about 35%, at least about 45%, at least about 55%, at least about 65%, at least about 75%, at least about 85%, at least about 90% or at least about 95% or more by weight of the CNS modulating agent.

In some embodiments, the viscosity of the gel compositions presented herein are measured by any means described. For example, in some embodiments, an LVDV-II+CP Cone Plate Viscometer and a Cone Spindle CPE-40 is used to calculate the viscosity of the gel composition described herein. In other embodiments, a Brookfield (spindle and cup) viscometer is used to calculate the viscosity of the gel composition described herein. In some embodiments, the viscosity ranges referred to herein are measured at room temperature. In other embodiments, the viscosity ranges referred to herein are measured at body temperature (e.g., at the average body temperature of a healthy human).

In one embodiment, the pharmaceutically acceptable enhanced viscosity auris-acceptable composition comprises at least one CNS modulating agent and at least one gelling agent. Suitable gelling agents for use in preparation of the gel composition include, but are not limited to, celluloses, cellulose derivatives, cellulose ethers (e.g., carboxymethylcellulose, ethylcellulose, hydroxyethylcellulose, hydroxymethylcellulose, hydroxypropylmethylcellulose, hydroxypropylcellulose, methylcellulose), guar gum, xanthan gum, locust bean gum, alginates (e.g., alginic acid), silicates, starch, tragacanth, carboxyvinyl polymers, carrageenan, paraffin, petrolatum and any combinations or mixtures thereof. In some other embodiments, hydroxypropylmethylcellulose (Methocel®) is utilized as the gelling agent. In certain embodiments, the viscosity enhancing agents described herein are also utilized as the gelling agent for the gel compositions presented herein:

In some embodiments, the otic therapeutic agents disclosed herein are dispensed as an auris-acceptable paint. As used herein, paints (also known as film formers) are solutions comprised of a solvent, a monomer or polymer, an active agent, and optionally one or more pharmaceutically-acceptable excipients. After application to a tissue, the solvent evaporates leaving behind a thin coating comprised of the monomers or polymers, and the active agent. The coating protects active agents and maintains them in an immobilized state at the site of application. This decreases the amount of active agent that may be lost and correspondingly increases the amount delivered to the subject. By way of non-limiting example, paints include collodions (e.g. Flexible Collodion, USP), and solutions comprising saccharide siloxane copolymers and a cross-linking agent. Collodions are ethyl ether/ethanol solutions containing pyroxylin (a nitrocellulose). After application, the ethyl ether/ethanol solution evaporates leaving behind a thin film of pyroxylin. In solutions comprising saccharide siloxane copolymers, the saccharide siloxane copolymers form the coating after evaporation of the solvent initiates the cross-linking of the saccharide siloxane copolymers. For additional disclosures regarding paints, see *Remington: The Science and Practice of Pharmacy* that is hereby incorporated with respect to this subject matter. The paints contemplated for use herein, are flexible such that they do not interfere with the propagation of pressure waves through the ear. Further, the paints may be applied as a liquid (i.e. solution, suspension, or emulsion), a semisolid (i.e. a gel, foam, paste, or jelly) or an aerosol.

In some embodiments, the otic therapeutic agents disclosed herein are dispensed as a controlled-release foam. Examples of suitable foamable carriers for use in the compositions disclosed herein include, but are not limited to, alginate and derivatives thereof, carboxymethylcellulose and derivatives thereof, collagen, polysaccharides, including, for example, dextran, dextran derivatives, pectin, starch, modified starches such as starches having additional carboxyl and/or carboxamide groups and/or having hydrophilic sidechains, cellulose and derivatives thereof, agar and derivatives thereof, such as agar stabilized with polyacrylamide, polyethylene oxides, glycol methacrylates, gelatin, gums such as xanthum, guar, karaya, gellan, arabic, tragacanth and locust bean gum, or combinations thereof. Also suitable are the salts of the aforementioned carriers, for example, sodium alginate. The composition optionally further comprises a foaming agent, which promotes the formation of the foam, including a surfactant or external propellant. Examples of suitable foaming agents include cetrimide, lecithin, soaps, silicones and the like. Commercially available surfactants such as Tween® are also suitable.

In some embodiments, other gel compositions are useful depending upon the particular CNS modulating agent, other pharmaceutical agent or excipients/additives used, and as such are considered to fall within the scope of the present disclosure. For example, other commercially-available glycerin-based gels, glycerin-derived compounds, conjugated, or crosslinked gels, matrices, hydrogels, and polymers, as well as gelatins and their derivatives, alginates, and alginate-based gels, and even various native and synthetic hydrogel and hydrogel-derived compounds are all expected to be useful in the CNS modulating agent compositions described herein. In some embodiments, auris-acceptable gels include, but are not limited to, alginate hydrogels SAF®-Gel (ConvaTec, Princeton, N.J.), Duoderm® Hydroactive Gel (ConvaTec), Nu-Gel® (Johnson & Johnson Medical, Arlington, Tex.); Carrasyn® (V) Acemannan Hydrogel (Carrington Laboratories, Inc., Irving, Tex.); glycerin gels Elta® Hydrogel (Swiss-American Products, Inc., Dallas, Tex.) and K-Y® Sterile (Johnson & Johnson). In further embodiments, biodegradable biocompatible gels also represent compounds present in auris-acceptable compositions disclosed and described herein.

In some compositions developed for administration to a mammal, and for compositions formulated for human administration, the auris-acceptable gel comprises substantially all of the weight of the composition. In other embodiments, the auris-acceptable gel comprises as much as about 98% or about 99% of the composition by weight. This is desirous when a substantially non-fluid, or substantially viscous composition is needed. In a further embodiment, when slightly less viscous, or slightly more fluid auris-acceptable pharmaceutical gel compositions are desired, the biocompatible gel portion of the composition comprises at least about 50% by weight, at least about 60% by weight, at least about 70% by weight, or even at least about 80% or 90% by weight of the compound. All intermediate integers within these ranges are contemplated to fall within the scope of this disclosure, and in some alternative embodiments, even more fluid (and consequently less viscous) auris-acceptable gel compositions are formulated, such as for example, those in that the gel or matrix component of the mixture comprises not more than about 50% by weight, not more than about 40% by weight, not more than about 30% by weight, or even those than comprise not more than about 15% or about 20% by weight of the composition.

Auris-Acceptable Suspending Agents

In one embodiment, at least one CNS modulating agent is included in a pharmaceutically acceptable enhanced viscosity composition wherein the composition further comprises at least one suspending agent, wherein the suspending agent assists in imparting controlled-release characteristics to the composition. In some embodiments, suspending agents also serve to increase the viscosity of the auris-acceptable CNS modulating compositions and compositions.

Suspending agents include, by way of example only, compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), sodium carboxymethylcellulose, methylcellulose, hydroxypropylmethylcellulose (hypromellose), hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like. In some embodiments, useful aqueous suspensions also contain one or more polymers as suspending agents. Useful polymers include water-soluble polymers such as cellulosic polymers, e.g., hydroxypropyl methylcellulose, and water-insoluble polymers such as cross-linked carboxyl-containing polymers.

In one embodiment, the present disclosure provides auris-acceptable gel compositions comprising a therapeutically effective amount of a CNS modulating agent in a hydroxyethyl cellulose gel. Hydroxyethyl cellulose (HEC) is obtained as a dry powder that is reconstituted in water or an aqueous buffer solution to give the desired viscosity (generally about 200 cps to about 30,000 cps, corresponding to about 0.2 to about 10% HEC). In one embodiment the concentration of HEC is between about 1% and about 15%, about 1% and about 2%, or about 1.5% to about 2%.

In other embodiments, the auris-acceptable compositions, including gel compositions and viscosity-enhanced compositions, further include excipients, other medicinal or pharmaceutical agents, carriers, adjuvants, such as preserving, stabilizing, wetting or emulsifying agents, solution promoters, salts, solubilizers, an antifoaming agent, an antioxidant, a dispersing agent, a wetting agent, a surfactant, and combinations thereof.

Auris-Acceptable Actinic Radiation Curable Gel

In other embodiments, the gel is an actinic radiation curable gel, such that following administration to or near the targeted auris structure, use of actinic radiation (or light, including UV light, visible light, or infrared light) the desired gel properties are formed. By way of example only, fiber optics are used to provide the actinic radiation so as to form the desired gel properties. In some embodiments, the fiber optics and the gel administration device form a single unit. In other embodiments, the fiber optics and the gel administration device are provided separately.

Auris-Acceptable Solvent Release Gel

In some embodiments, the gel is a solvent release gel such that the desired gel properties are formed after administration to or near the targeted auris structure, which is, as the solvent in the injected gel composition diffuses out the gel, a gel having the desired gel properties is formed. For example, a composition that comprises sucrose acetate isobutyrate, a pharmaceutically acceptable solvent, one or more additives, and the CNS modulating agent is administered at or near the round window membrane: diffusion of the solvent out of the injected composition provides a depot having the desired gel properties. For example, use of a water soluble solvent provides a high viscosity depot when the solvent diffuses rapidly out of the injected composition. On the other hand, use of a hydrophobic solvent (e.g., benzyl benzoate) provides a less viscous depot. One example of an auris-acceptable solvent release gel composition is the SABER™ Delivery System marketed by DURECT Corporation.

Auris-Acceptable In Situ Forming Spongy Material

Also contemplated within the scope of the embodiments is the use of a spongy material, formed in situ in the auris interna or auris media. In some embodiments, the spongy material is formed from hyaluronic acid or its derivatives. The spongy material is impregnated with a desired CNS modulating agent and placed within the auris media so as to provide controlled-release of the CNS modulating agent within the auris media, or in contact with the round window membrane so as to provide controlled-release of the CNS modulating agent into the auris interna. In some embodiments, the spongy material is biodegradable.

Round Window Membrane Mucoadhesives

Also contemplated within the scope of the embodiments is the addition of a round window membrane mucoadhesive with the CNS modulating agent compositions and compositions and devices disclosed herein. The term 'mucoadhesion' is used for materials that bind to the mucin layer of a biological membrane, such as the external membrane of the 3-layered round window membrane. To serve as round window membrane mucoadhesive polymers, the polymers possess some general physiochemical features such as predominantly anionic hydrophilicity with numerous hydrogen bond forming groups, suitable surface property for wetting mucus/mucosal tissue surfaces or sufficient flexibility to penetrate the mucus network.

Round window membrane mucoadhesive agents that are used with the auris-acceptable compositions include, but are not limited to, at least one soluble polyvinylpyrrolidone polymer (PVP); a water-swellable, but water-insoluble, fibrous, cross-linked carboxy-functional polymer; a crosslinked poly (acrylic acid) (e.g. Carbopol® 947P); a carbomer homopolymer; a carbomer copolymer; a hydrophilic polysaccharide gum, maltodextrin, a cross-linked alignate gum gel, a water-dispersible polycarboxylated vinyl polymer, at least two particulate components selected from the group consisting of titanium dioxide, silicon dioxide, and clay, or a mixture thereof. The round window membrane mucoadhesive agent is optionally used in combination with an auris-acceptable viscosity increasing excipient, or used alone to increase the interaction of the composition with the mucosal layer target otic component. In one non-limiting example, the mucoadhesive agent is maltodextrin and/or an alginate gum. When used, the round window membrane mucoadhesive character imparted to the composition is at a level that is sufficient to deliver an effective amount of the CNS modulating agent composition to, for example, the mucosal layer of round window membrane or the crista fenestrae cochleae in an amount that coats the mucosal membrane, and thereafter deliver the composition to the affected areas, including by way of example only, the vestibular and/or cochlear structures of the auris interna. When used, the mucoadhesive characteristics of the compositions provided herein are determined, and using this information (along with the other teachings provided herein), the appropriate amounts are determined. One method for determining sufficient mucoadhesiveness includes monitoring changes in the interaction of the composition with a mucosal layer, including but not limited to measuring changes in residence or retention time of the composition in the absence and presence of the mucoadhesive excipient.

Mucoadhesive agents have been described, for example, in U.S. Pat. Nos. 6,638,521, 6,562,363, 6,509,028, 6,348,502, 6,319,513, 6,306,789, 5,814,330, and 4,900,552, each of that is hereby incorporated by reference for such disclosure.

In another non-limiting example, a mucoadhesive agent is, for example, at least two particulate components selected from titanium dioxide, silicon dioxide, and clay, wherein the composition is not further diluted with any liquid prior to administration and the level of silicon dioxide, if present, is from about 3% to about 15%, by weight of the composition. Silicon dioxide, if present, includes fumed silicon dioxide, precipitated silicon dioxide, coacervated silicon dioxide, gel silicon dioxide, and mixtures thereof. Clay, if present, includes kaolin minerals, serpentine minerals, smectites, illite or a mixture thereof. For example, clay includes laponite, bentonite, hectorite, saponite, montmorillonites or a mixture thereof.

In one non-limiting example, the round window membrane mucoadhesive agent is maltodextrin. Maltodextrin is a carbohydrate produced by the hydrolysis of starch that is optionally derived from corn, potato, wheat or other plant products. Maltodextrin is optionally used either alone or in combination with other round window membrane mucoadhesive agents to impart mucoadhesive characteristics on the compositions disclosed herein. In one embodiment, a combination of maltodextrin and a carbopol polymer are used to increase the round window membrane mucoadhesive characteristics of the compositions or devices disclosed herein.

In another embodiment, the round window membrane mucoadhesive agent is an alkyl-glycoside and/or a saccharide alkyl ester. As used herein, an "alkyl-glycoside" means a compound comprising any hydrophilic saccharide (e.g. sucrose, maltose, or glucose) linked to a hydrophobic alkyl. In some embodiments, the round window membrane mucoadhesive agent is an alkyl-glycoside wherein the alkyl-glycoside comprises a sugar linked to a hydrophobic alkyl (e.g., an alkyl comprising about 6 to about 25 carbon atoms) by an amide linkage, an amine linkage, a carbamate linkage, an ether linkage, a thioether linkage, an ester linkage, a thioester linkage, a glycosidic linkage, a thioglycosidic linkage, and/or a ureide linkage. In some embodiments, the round window membrane mucoadhesive agent is a hexyl-, heptyl-, octyl-, nonyl-, decyl-, undecyl-, dodecyl-, tridecyl-, tetradecyl, pentadecyl-, hexadecyl-, heptadecyl-, and octadecyl α- or β-D-maltoside; hexyl-, heptyl-, octyl-, nonyl-, decyl-, undecyl-, dodecyl-, tridecyl-, tetradecyl, pentadecyl-, hexadecyl-, heptadecyl-, and octadecyl α- or β-D-glucoside; hexyl-, heptyl-, octyl-, nonyl-, decyl-, undecyl-, dodecyl-, tridecyl-, tetradecyl, pentadecyl-, hexadecyl-, heptadecyl-, and octadecyl α- or β-D-sucroside; hexyl-, heptyl-, octyl-, dodecyl-, tridecyl-, and tetradecyl-β-D-thiomaltoside; heptyl- or octyl-1-thio-α- or β-D-glucopyranoside; alkyl thiosucroses; alkyl maltotriosides; long chain aliphatic carbonic acid amides of sucrose β-amino-alkyl ethers; derivatives of palatinose or isomaltamine linked by an amide linkage to an alkyl chain and derivatives of isomaltamine linked by urea to an alkyl chain; long chain aliphatic carbonic acid ureides of sucrose β-amino-alkyl ethers and long chain aliphatic carbonic acid amides of sucrose β-amino-alkyl ethers. In some embodiments, the round window membrane mucoadhesive agent is an alkyl-glycoside wherein the alkyl glycoside is maltose, sucrose, glucose, or a combination thereof linked by a glycosidic linkage to an alkyl chain of 9-16 carbon atoms (e.g., nonyl-, decyl-, dodecyl- and tetradecyl sucroside; nonyl-, decyl-, dodecyl- and tetradecyl glucoside; and nonyl-, decyl-, dodecyl- and tetradecyl maltoside). In some embodiments, the round window membrane mucoadhesive agent is an alkyl-glycoside wherein the alkyl glycoside is dodecylmaltoside, tridecylmaltoside, and tetradecylmaltoside.

In some embodiments, the round window membrane mucoadhesive agent is an alkyl-glycoside wherein the alkyl-glycoside is a disaccharide with at least one glucose. In some embodiments, the auris acceptable penetration enhancer is a surfactant comprising α-D-glucopyranosyl-β-glycopyranoside, n-Dodecyl-4-O-α-D-glucopyranosyl-β-glycopyranoside, and/or n-tetradecyl-4-O-α-D-glucopyranosyl-β-glycopyranoside. In some embodiments, the round window membrane mucoadhesive agent is an alkyl-glycoside wherein the alkyl-glycoside has a critical miscelle concentration (CMC) of less than about 1 mM in pure water or in aqueous solutions. In some embodiments, the round window membrane mucoadhesive agent is an alkyl-glycoside wherein an oxygen atom within the alkyl-glycoside is substituted with a sulfur atom. In some embodiments, the round window membrane mucoadhesive agent is an alkyl-glycoside wherein the alkylglycoside is the 0 anomer. In some embodiments, the round window membrane mucoadhesive agent is an alkyl-glycoside wherein the alkylglycoside comprises 90%, 91%, 92%, 93%, 94%, 95%, 96%, 97%, 98%, 99%, 99.1%, 99.5%, or 99.9% of the β anomer.

Auris-Acceptable Controlled-Release Particles

CNS modulating agents and/or other pharmaceutical agents disclosed herein are optionally incorporated within controlled-release particles, lipid complexes, liposomes, nanoparticles, microparticles, microspheres, coacervates, nanocapsules or other agents that enhance or facilitate the localized delivery of the CNS modulating agent. In some embodiments, a single enhanced viscosity composition is used, in that at least one CNS modulating agent is present, while in other embodiments, a pharmaceutical composition that comprises a mixture of two or more distinct enhanced viscosity compositions is used, in that at least one CNS modulating agent is present. In some embodiments, combinations of sols, gels and/or biocompatible matrices is also employed to provide desirable characteristics of the controlled-release CNS modulating compositions or compositions. In certain embodiments, the controlled-release CNS modulating compositions or compositions are cross-linked by one or more agents to alter or improve the properties of the composition.

Examples of microspheres relevant to the pharmaceutical compositions disclosed herein include: Luzzi, L. A., J. Pharm. Psy. 59:1367 (1970); U.S. Pat. No. 4,530,840; Lewis, D. H., "Controlled-release of Bioactive Agents from Lactides/Glycolide Polymers" in Biodegradable Polymers as Drug Delivery Systems, Chasin, M. and Langer, R., eds., Marcel Decker (1990); U.S. Pat. No. 4,675,189; Beck et al., "Poly(lactic acid) and Poly(lactic acid-co-glycolic acid) Contraceptive Delivery Systems," in Long Acting Steroid Contraception, Mishell, ed., Raven Press (1983); U.S. Pat. No. 4,758,435; U.S. Pat. No. 3,773,919; U.S. Pat. No. 4,474,572. Examples of protein therapeutics formulated as microspheres include: U.S. Pat. No. 6,458,387; U.S. Pat. No. 6,268,053; U.S. Pat. No. 6,090,925; U.S. Pat. No. 5,981,719; and U.S. Pat. No. 5,578,709, and are herein incorporated by reference for such disclosure.

Microspheres usually have a spherical shape, although irregularly-shaped microparticles are possible. Microspheres may vary in size, ranging from submicron to 1000 micron diameters. Microspheres suitable for use with the auris-acceptable compositions disclosed herein are submicron to 250 micron diameter microspheres, allowing administration by injection with a standard gauge needle. The auris-acceptable microspheres are prepared by any method that produces microspheres in a size range acceptable for use in an injectable composition. Injection is optionally accomplished with standard gauge needles used for administering liquid compositions.

Suitable examples of polymeric matrix materials for use in the auris-acceptable controlled-release particles herein include poly(glycolic acid), poly-d,l-lactic acid, poly-l-lactic acid, copolymers of the foregoing, poly(aliphatic carboxylic acids), copolyoxalates, polycaprolactone, polydioxonene, poly(orthocarbonates), poly(acetals), poly(lactic acid-caprolactone), polyorthoesters, poly(glycolic acid-caprolactone), polydioxonene, polyanhydrides, polyphosphazines, and natural polymers including albumin, casein, and some waxes, such as, glycerol mono- and distearate, and the like. Various commercially available poly(lactide-co-glycolide) materials (PLGA) are optionally used in the method disclosed herein. For example, poly(d,l-lactic-co-glycolic acid) is commercially available from Boehringer-Ingelheim as RESOMER RG 503 H. This product has a mole percent composition of 50% lactide and 50% glycolide. These copolymers are available in a wide range of molecular weights and ratios of lactic acid to glycolic acid. One embodiment includes the use of the polymer poly(d,l-lactide-co-glycolide). The molar ratio of lactide to glycolide in such a copolymer includes the range of from about 95:5 to about 50:50.

The molecular weight of the polymeric matrix material is of some importance. The molecular weight should be high enough so that it forms satisfactory polymer coatings, i.e., the polymer should be a good film former. Usually, a satisfactory molecular weight is in the range of 5,000 to 500,000 Daltons. The molecular weight of a polymer is also important from the point of view that molecular weight influences the biodegradation rate of the polymer. For a diffusional mechanism of drug release, the polymer should remain intact until all of the drug is released from the microparticles and then degrade. The drug is also released from the microparticles as the polymeric excipient bioerodes. By an appropriate selection of polymeric materials a microsphere composition is made such that the resulting microspheres exhibit both diffusional release and biodegradation release properties. This is useful in affording multiphasic release patterns.

A variety of methods are known by that compounds are encapsulated in microspheres. In these methods, the CNS modulating agent is generally dispersed or emulsified, using stirrers, agitators, or other dynamic mixing techniques, in a solvent containing a wall-forming material. Solvent is then removed from the microspheres, and thereafter the microsphere product is obtained.

In one embodiment, controlled-release CNS modulating compositions are made through the incorporation of the CNS modulating agents and/or other pharmaceutical agents into ethylene-vinyl acetate copolymer matrices. (See U.S. Pat. No. 6,083,534, incorporated herein for such disclosure). In another embodiment, CNS modulating agents are incorporated into poly(lactic-glycolic acid) or poly-L-lactic acid microspheres. Id. In yet another embodiment, the CNS modulating agents are encapsulated into alginate microspheres. (See U.S. Pat. No. 6,036,978, incorporated herein for such disclosure). Biocompatible methacrylate-based polymers to encapsulate the CNS modulating compounds or compositions are optionally used in the compositions and methods disclosed herein. A wide range of methacrylate-based polymer systems are commercially available, such as the EUDRAGIT polymers marketed by Evonik. One useful aspect of methacrylate polymers is that the properties of the composition are varied by incorporating various co-polymers. For example, poly(acrylic acid-co-methylmethacrylate) microparticles exhibit enhanced mucoadhesion properties as the carboxylic acid groups in the poly(acrylic acid) form hydrogen bonds with mucin (Park et al, Pharm. Res. (1987) 4(6):457-464). Variation of the ratio between acrylic acid and methylmethacrylate monomers serves to modulate the properties of the co-polymer. Methacrylate-based microparticles have also been used in protein therapeutic compositions (Naha et al, Journal of Microencapsulation 4 Feb. 2008 (online publication)). In one embodiment, the enhanced viscosity auris-acceptable compositions described herein comprises CNS modulating microspheres wherein the microspheres are formed from a methacrylate polymer or copolymer. In an additional embodiment, the enhanced viscosity composition described herein comprises CNS modulating microspheres wherein the microspheres are mucoadhesive. Other controlled-release systems, including incorporation or deposit of polymeric materials or matrices onto solid or hollow spheres containing CNS modulating agents, are also explicitly contemplated within the embodiments disclosed herein. The types of controlled-release systems available without significantly losing activity of the CNS modulating agent are determined using the teachings, examples, and principles disclosed herein An example of a conventional microencapsulation process for pharmaceutical preparations is shown in U.S. Pat. No. 3,737,337, incorporated herein by reference for such disclosure. The CNS modulating substances to be encapsulated or embedded are dissolved or dispersed in the organic solution of the polymer (phase A), using conventional mixers, including (in the preparation of dispersion) vibrators and high-speed stirrers, etc. The dispersion of phase (A), containing the core material in solution or in suspension, is carried out in the aqueous phase (B), again using conventional mixers, such as high-speed mixers, vibration mixers, or even spray nozzles, in that case the particle size of the microspheres will be determined not only by the concentration of phase (A), but also by the emulsate or microsphere size. With conventional techniques for the microencapsulation of a CNS modulating agents, the microspheres form when the solvent containing an active agent and a polymer is emulsified or dispersed in an immiscible solution by stirring, agitating, vibrating, or some other dynamic mixing technique, often for a relatively long period of time.

Methods for the construction of microspheres are also described in U.S. Pat. No. 4,389,330, and U.S. Pat. No. 4,530, 840, incorporated herein by reference for such disclosure. The desired CNS modulating agent is dissolved or dispersed in an appropriate solvent. To the agent-containing medium is added the polymeric matrix material in an amount relative to the active ingredient that gives a product of the desired loading of active agent. Optionally, all of the ingredients of the CNS modulating microsphere product can be blended in the solvent medium together. Suitable solvents for the agent and the polymeric matrix material include organic solvents such as acetone, halogenated hydrocarbons such as chloroform, methylene chloride and the like, aromatic hydrocarbon compounds, halogenated aromatic hydrocarbon compounds, cyclic ethers, alcohols, ethyl acetate and the like.

The mixture of ingredients in the solvent is emulsified in a continuous-phase processing medium; the continuous-phase medium being such that a dispersion of microdroplets containing the indicated ingredients is formed in the continuous-phase medium. Naturally, the continuous-phase processing medium and the organic solvent must be immiscible, and includes water although nonaqueous media such as xylene and toluene and synthetic oils and natural oils are optionally used. Optionally, a surfactant is added to the continuous-phase processing medium to prevent the microparticles from agglomerating and to control the size of the solvent microdroplets in the emulsion. A preferred surfactant-dispersing medium combination is a 1 to 10 wt. % poly(vinyl alcohol) in water mixture. The dispersion is formed by mechanical agitation of the mixed materials. An emulsion is optionally formed by adding small drops of the active agent-wall forming material solution to the continuous phase processing medium. The temperature during the formation of the emulsion is not especially critical but influences the size and quality of the microspheres and the solubility of the drug in the continuous phase. It is desirable to have as little of the agent in the continuous phase as possible. Moreover, depending on the solvent and continuous-phase processing medium employed, the temperature must not be too low or the solvent and processing medium will solidify or the processing medium will become too viscous for practical purposes, or too high that the processing medium will evaporate, or that the liquid processing medium will not be maintained. Moreover, the temperature of the medium cannot be so high that the stability of the particular agent being incorporated in the microspheres is adversely affected. Accordingly, the dispersion process is conducted at any temperature that maintains stable operating conditions, which preferred temperature being about 15° C. to 60° C., depending upon the drug and excipient selected.

The dispersion that is formed is a stable emulsion and from this dispersion the organic solvent immiscible fluid is optionally partially removed in the first step of the solvent removal process. The solvent is removed by techniques such as heating, the application of a reduced pressure or a combination of both. The temperature employed to evaporate solvent from the microdroplets is not critical, but should not be that high that it degrades the CNS modulating agent employed in the preparation of a given microparticle, nor should it be so high as to evaporate solvent at such a rapid rate to cause defects in the wall forming material. Generally, from 5 to 75%, of the solvent is removed in the first solvent removal step.

After the first stage, the dispersed microparticles in the solvent immiscible fluid medium are isolated from the fluid medium by any convenient means of separation. Thus, for example, the fluid is decanted from the microsphere or the microsphere suspension is filtered. Still other, various combinations of separation techniques are used if desired.

Following the isolation of the microspheres from the continuous-phase processing medium, the remainder of the solvent in the microspheres is removed by extraction. In this step, the microspheres are suspended in the same continuous-phase processing medium used in step one, with or without surfactant, or in another liquid. The extraction medium removes the solvent from the microspheres and yet does not dissolve the microspheres. During the extraction, the extraction medium with dissolved solvent is optionally removed and replaced with fresh extraction medium. This is best done on a continual basis. The rate of extraction medium replenishment of a given process is a variable that is determined at the time the process is performed and, therefore, no precise limits for the rate must be predetermined. After the majority of the solvent has been removed from the microspheres, the microspheres are dried by exposure to air or by other conventional drying techniques such as vacuum drying, drying over a desiccant, or the like. This process is very efficient in encapsulating the CNS modulating agent since core loadings of up to 80 wt. %, preferably up to 60 wt. % are obtained.

Alternatively, controlled-release microspheres containing a CNS modulating agent is prepared through the use of static mixers. Static or motionless mixers consist of a conduit or tube in that is received a number of static mixing agents. Static mixers provide homogeneous mixing in a relatively short length of conduit, and in a relatively short period of time. With static mixers, the fluid moves through the mixer, rather than some part of the mixer, such as a blade, moving through the fluid.

A static mixer is optionally used to create an emulsion. When using a static mixer to form an emulsion, several factors determine emulsion particle size, including the density and viscosity of the various solutions or phases to be mixed, volume ratio of the phases, interfacial tension between the phases, static mixer parameters (conduit diameter; length of mixing element; number of mixing elements), and linear velocity through the static mixer. Temperature is a variable because it affects density, viscosity, and interfacial tension. The controlling variables are linear velocity, sheer rate, and pressure drop per unit length of static mixer.

In order to create microspheres containing a CNS modulating agent using a static mixer process, an organic phase and an aqueous phase are combined. The organic and aqueous phases are largely or substantially immiscible, with the aqueous phase constituting the continuous phase of the emulsion. The organic phase includes a CNS modulating agent as well as a wall-forming polymer or polymeric matrix material. The organic phase is prepared by dissolving a CNS modulating agent in an organic or other suitable solvent, or by forming a dispersion or an emulsion containing the CNS modulating agent. The organic phase and the aqueous phase are pumped so that the two phases flow simultaneously through a static mixer, thereby forming an emulsion that comprises microspheres containing the CNS modulating agent encapsulated in the polymeric matrix material. The organic and aqueous phases are pumped through the static mixer into a large volume of quench liquid to extract or remove the organic solvent. Organic solvent is optionally removed from the microspheres while they are washing or being stirred in the quench liquid. After the microspheres are washed in a quench liquid, they are isolated, as through a sieve, and dried.

In one embodiment, microspheres are prepared using a static mixer. The process is not limited to the solvent extraction technique discussed above, but is used with other encapsulation techniques. For example, the process is optionally used with a phase separation encapsulation technique. To do so, an organic phase is prepared that comprises a CNS modulating agent suspended or dispersed in a polymer solution. The non-solvent second phase is free from solvents for the polymer and active agent. A preferred non-solvent second phase is silicone oil. The organic phase and the non-solvent phase are pumped through a static mixer into a non-solvent quench liquid, such as heptane. The semi-solid particles are quenched for complete hardening and washing. The process of microencapsulation includes spray drying, solvent evaporation, a combination of evaporation and extraction, and melt extrusion.

In another embodiment, the microencapsulation process involves the use of a static mixer with a single solvent. This process is described in detail in U.S. application Ser. No. 08/338,805, herein incorporated by reference for such disclosure. An alternative process involves the use of a static mixer with co-solvents. In this process, biodegradable microspheres comprising a biodegradable polymeric binder and a CNS modulating agent are prepared, which comprises a blend of at least two substantially non-toxic solvents, free of halogenated hydrocarbons to dissolve both the agent and the polymer. The solvent blend containing the dissolved agent and polymer is dispersed in an aqueous solution to form droplets. The resulting emulsion is then added to an aqueous extraction medium preferably containing at least one of the solvents of the blend, whereby the rate of extraction of each solvent is controlled, whereupon the biodegradable microspheres containing the pharmaceutically active agent are formed. This process has the advantage that less extraction medium is required because the solubility of one solvent in water is substantially independent of the other and solvent selection is increased, especially with solvents that are particularly difficult to extract.

Nanoparticles are also contemplated for use with the CNS modulating agents disclosed herein. Nanoparticles are material structures of about 100 nm or less in size. One use of nanoparticles in pharmaceutical compositions is the formation of suspensions as the interaction of the particle surface with solvent is strong enough to overcome differences in density. Nanoparticle suspensions are sterilized as the nanoparticles are small enough to be subjected to sterilizing filtration (see, e.g., U.S. Pat. No. 6,139,870, herein incorporated by reference for such disclosure). Nanoparticles comprise at least one hydrophobic, water-insoluble and water-indispersible polymer or copolymer emulsified in a solution or aqueous dispersion of surfactants, phospholipids or fatty acids. The CNS modulating agent is optionally introduced with the polymer or the copolymer into the nanoparticles.

Lipid nanocapsules as controlled-release structures, as well for penetrating the round window membrane and reaching auris interna and/or auris media targets, is also contemplated herein. Lipid nanocapsules are optionally formed by emulsifying capric and caprylic acid triglycerides (Labrafac WL 1349; avg. mw 512), soybean lecithin (LIPOID® S75-3; 69% phosphatidylcholine and other phospholipids), surfactant (for example, Solutol HS15), a mixture of polyethylene glycol 660 hydroxystearate and free polyethylene glycol 660; NaCl and water. The mixture is stirred at room temperature to obtain an oil emulsion in water. After progressive heating at a rate of 4° C./min under magnetic stirring, a short interval of transparency should occur close to 70° C., and the inverted phase (water droplets in oil) obtained at 85° C. Three cycles of cooling and heating is then applied between 85° C. and 60° C. at the rate of 4° C./min, and a fast dilution in cold water at a temperature close to 0° C. to produce a suspension of nanocapsules. To encapsulate the CNS modulating agents, the agent is optionally added just prior to the dilution with cold water.

CNS modulating agents are also inserted into the lipid nanocapsules by incubation for 90 minutes with an aqueous micellar solution of the auris active agent. The suspension is then vortexed every 15 minutes, and then quenched in an ice bath for 1 minute.

Suitable auris-acceptable surfactants are, by way of example, cholic acid or taurocholic acid salts. Taurocholic acid, the conjugate formed from cholic acid and taurine, is a fully metabolizable sulfonic acid surfactant. An analog of taurocholic acid, tauroursodeoxycholic acid (TUDCA), is a naturally occurring bile acid and is a conjugate of taurine and ursodeoxycholic acid (UDCA). Other naturally occurring anionic (e.g., galactocerebroside sulfate), neutral (e.g., lactosylceramide) or zwitterionic surfactants (e.g., sphingomyelin, phosphatidyl choline, palmitoyl carnitine) are optionally used to prepare nanoparticles.

The auris-acceptable phospholipids are chosen, by way of example, from natural, synthetic or semi-synthetic phospholipids; lecithins (phosphatidylcholine) such as, for example, purified egg or soya lecithins (lecithin E100, lecithin E80 and phospholipons, for example phospholipon 90), phosphatidylethanolamine, phosphatidylserine, phosphatidylinositol, phosphatidylglycerol, dipalmitoylphosphatidylcholine, dipalmitoylglycerophosphatidylcholine, dimyristoylphosphatidylcholine, distearoylphosphatidylcholine and phosphatidic acid or mixtures thereof are used more particularly.

Fatty acids for use with the auris-acceptable compositions are chosen from, by way of example, lauric acid, mysristic acid, palmitic acid, stearic acid, isostearic acid, arachidic acid, behenic acid, oleic acid, myristoleic acid, palmitoleic acid, linoleic acid, alpha-linoleic acid, arachidonic acid, eicosapentaenoic acid, erucic acid, docosahexaenoic acid, and the like.

Suitable auris-acceptable surfactants are selected from known organic and inorganic pharmaceutical excipients. Such excipients include various polymers, low molecular weight oligomers, natural products, and surfactants. Preferred surface modifiers include nonionic and ionic surfactants. Two or more surface modifiers are used in combination.

Representative examples of auris-acceptable surfactants include cetyl pyridinium chloride, gelatin, casein, lecithin (phosphatides), dextran, glycerol, gum acacia, cholesterol, tragacanth, stearic acid, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters; dodecyl trimethyl ammonium bromide, polyoxyethylenestearates, colloidal silicon dioxide, phosphates, sodium dodecylsulfate, carboxymethylcellulose calcium, hydroxypropyl cellulose (HPC, HPC-SL, and HPC-L), hydroxypropyl methylcellulose (HPMC), carboxymethylcellulose sodium, methylcellulose, hydroxyethylcellulose, hydroxypropylcellulose, hydroxypropylmethyl-cellulose phthalate, noncrystalline cellulose, magnesium aluminum silicate, triethanolamine, polyvinyl alcohol (PVA), polyvinylpyrrolidone (PVP), 4-(1,1,3,3-tetaamethylbutyl)-phenol polymer with ethylene oxide and formaldehyde (also known as tyloxapol, superione, and triton), poloxamers, poloxamines, a charged phospholipid such as dimyristoyl phophatidyl glycerol, dioctylsulfosuccinate (DOSS); Tetronic® 1508, dialkylesters of sodium sulfosuccinic acid, Duponol P, Tritons X-200, Crodestas F-110, p-isononylphenoxypoly-(glycidol), Crodestas SL-40 (Croda, Inc.); and SA9OHCO, which is $C_{18}H_{37}CH_2$ $(CON(CH_3)$—$CH_2$ $(CHOH)_4$ $(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; and the like. Most of these surfactants are known pharmaceutical excipients and are described in detail in the Handbook of Pharmaceutical Excipients, published jointly by the American Pharmaceutical Association and The Pharmaceutical Society of Great Britain (The Pharmaceutical Press, 1986), specifically incorporated by reference for such disclosure.

The hydrophobic, water-insoluble and water-indispersible polymer or copolymer may be chosen from biocompatible and biodegradable polymers, for example lactic or glycolic acid polymers and copolymers thereof, or polylactic/polyethylene (or polypropylene) oxide copolymers, preferably with molecular weights of between 1000 and 200,000, polyhydroxybutyric acid polymers, polylactones of fatty acids containing at least 12 carbon atoms, or polyanhydrides.

The nanoparticles may be obtained by coacervation, or the technique of evaporation of solvent, from an aqueous dispersion or solution of phospholipids and of an oleic acid salt into that is added an immiscible organic phase comprising the active principle and the hydrophobic, water-insoluble and water-indispersible polymer or copolymer. The mixture is pre-emulsified and then subjected to homogenization and evaporation of the organic solvent to obtain an aqueous suspension of very small-sized nanoparticles.

A variety of methods are optionally employed to fabricate the CNS modulating nanoparticles that are within the scope of the embodiments. These methods include vaporization methods, such as free jet expansion, laser vaporization, spark erosion, electro explosion and chemical vapor deposition; physical methods involving mechanical attrition (e.g., "pearl-milling" technology, Elan Nanosystems), super critical CO2 and interfacial deposition following solvent displacement. In one embodiment, the solvent displacement method is used. The size of nanoparticles produced by this method is sensitive to the concentration of polymer in the organic solvent; the rate of mixing; and to the surfactant employed in the process. Continuous flow mixers provide the necessary turbulence to ensure small particle size. One type of continuous flow mixing device that is optionally used to prepare nanoparticles has been described (Hansen et al J Phys Chem 92, 2189-96, 1988). In other embodiments, ultrasonic devices, flow through homogenizers or supercritical CO2 devices may be used to prepare nanoparticles.

If suitable nanoparticle homogeneity is not obtained on direct synthesis, then size-exclusion chromatography is used to produce highly uniform drug-containing particles that are freed of other components involved in their fabrication. Size-exclusion chromatography (SEC) techniques, such as gel-filtration chromatography, is used to separate particle-bound CNS modulating agent or other pharmaceutical compound from free CNS modulating agent or other pharmaceutical compound, or to select a suitable size range of CNS modulating-containing nanoparticles. Various SEC media, such as Superdex 200, Superose 6, Sephacryl 1000 are commercially available and are employed for the size-based fractionation of such mixtures. Additionally, nanoparticles are optionally purified by centrifugation, membrane filtration and by use of other molecular sieving devices, crosslinked gels/materials and membranes.

Auris-Acceptable Cyclodextrin and Other Stabilizing Compositions

In a specific embodiment, the auris-acceptable compositions alternatively comprises a cyclodextrin. Cyclodextrins are cyclic oligosaccharides containing 6, 7, or 8 glucopyranose units, referred to as α-cyclodextrin, β-cyclodextrin, or γ-cyclodextrin respectively: Cyclodextrins have a hydrophilic exterior, which enhances water-soluble, and a hydrophobic interior that forms a cavity. In an aqueous environment, hydrophobic portions of other molecules often enter the hydrophobic cavity of cyclodextrin to form inclusion compounds. Additionally, cyclodextrins are also capable of other types of nonbonding interactions with molecules that are not inside the hydrophobic cavity. Cyclodextrins have three free hydroxyl groups for each glucopyranose unit, or 18 hydroxyl groups on α-cyclodextrin, 21 hydroxyl groups on β-cyclodextrin, and 24 hydroxyl groups on γ-cyclodextrin. One or more of these hydroxyl groups can be reacted with any of a number of reagents to form a large variety of cyclodextrin derivatives, including hydroxypropyl ethers, sulfonates, and sulfoalkylethers. Shown below is the structure of β-cyclodextrin and the hydroxypropyl-β-cyclodextrin (HPβCD).

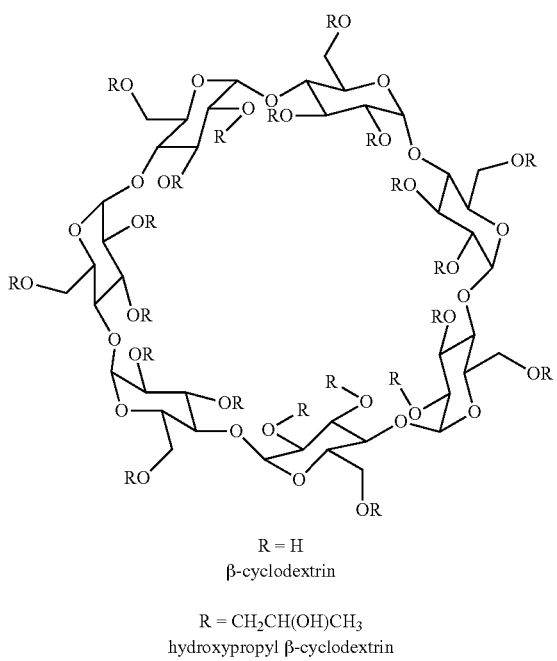

R = H
β-cyclodextrin

R = $CH_2CH(OH)CH_3$
hydroxypropyl β-cyclodextrin

In some embodiments, the use of cyclodextrins in the pharmaceutical compositions described herein improves the solubility of the drug. Inclusion compounds are involved in many cases of enhanced solubility; however other interactions between cyclodextrins and insoluble compounds also improves solubility. Hydroxypropyl-β-cyclodextrin (HP-βCD) is commercially available as a pyrogen free product. It is a nonhygroscopic white powder that readily dissolves in water. HPβCD is thermally stable and does not degrade at neutral pH. Thus, cyclodextrins improve the solubility of a therapeutic agent in a composition or composition. Accordingly, in some embodiments, cyclodextrins are included to increase the solubility of the auris-acceptable CNS modulating agents within the compositions described herein. In other embodiments, cyclodextrins in addition serve as controlled-release excipients within the compositions described herein.

By way of example only, cyclodextrin derivatives for use include α-cyclodextrin, cyclodextrin, γ-cyclodextrin, hydroxyethyl β-cyclodextrin, hydroxypropyl γ-cyclodextrin, sulfated β-cyclodextrin, sulfated α-cyclodextrin, sulfobutyl ether β-cyclodextrin.

The concentration of the cyclodextrin used in the compositions and methods disclosed herein varies according to the physiochemical properties, pharmacokinetic properties, side effect or adverse events, composition considerations, or other factors associated with the therapeutically active agent, or a salt or prodrug thereof, or with the properties of other excipients in the composition. Thus, in certain circumstances, the concentration or amount of cyclodextrin used in accordance with the compositions and methods disclosed herein will vary, depending on the need. When used, the amount of cyclodextrins needed to increase solubility of the CNS modulating agent and/or function as a controlled-release excipient in any of the compositions described herein is selected using the principles, examples, and teachings described herein.

Other stabilizers that are useful in the auris-acceptable compositions disclosed herein include, for example, fatty acids, fatty alcohols, alcohols, long chain fatty acid esters, long chain ethers, hydrophilic derivatives of fatty acids, polyvinyl pyrrolidones, polyvinyl ethers, polyvinyl alcohols, hydrocarbons, hydrophobic polymers, moisture-absorbing polymers, and combinations thereof. In some embodiments, amide analogues of stabilizers are also used. In further embodiments, the chosen stabilizer changes the hydrophobicity of the composition (e.g., oleic acid, waxes), or improves the mixing of various components in the composition (e.g., ethanol), controls the moisture level in the formula (e.g., PVP or polyvinyl pyrrolidone), controls the mobility of the phase (substances with melting points higher than room temperature such as long chain fatty acids, alcohols, esters, ethers, amides etc. or mixtures thereof; waxes), and/or improves the compatibility of the formula with encapsulating materials (e.g., oleic acid or wax). In another embodiment some of these stabilizers are used as solvents/co-solvents (e.g., ethanol). In other embodiments, stabilizers are present in sufficient amounts to inhibit the degradation of the CNS modulating agent. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Additional useful CNS modulating agent auris-acceptable compositions include one or more anti-aggregation additives to enhance stability of a CNS modulating agent compositions by reducing the rate of protein aggregation. The anti-aggregation additive selected depends upon the nature of the conditions to that the CNS modulating agents, for example CNS modulating agent antibodies are exposed. For example, certain compositions undergoing agitation and thermal stress require a different anti-aggregation additive than a composition undergoing lyophilization and reconstitution. Useful anti-aggregation additives include, by way of example only, urea, guanidinium chloride, simple amino acids such as glycine or arginine, sugars, polyalcohols, polysorbates, polymers such as polyethylene glycol and dextrans, alkyl saccharides, such as alkyl glycoside, and surfactants.

Other useful compositions optionally include one or more auris-acceptable antioxidants to enhance chemical stability where required. Suitable antioxidants include, by way of example only, ascorbic acid, methionine, sodium thiosulfate and sodium metabisulfite. In one embodiment, antioxidants are selected from metal chelating agents, thiol containing compounds and other general stabilizing agents.

Still other useful compositions include one or more auris-acceptable surfactants to enhance physical stability or for other purposes. Suitable nonionic surfactants include, but are not limited to, polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

In some embodiments, the auris-acceptable pharmaceutical compositions described herein are stable with respect to compound degradation over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 3 months, at least about 4 months, at least about 5 months, or at least about 6 months. In other embodiments, the compositions described herein are stable with respect to compound degradation over a period of at least about 1 week. Also described herein are compositions that are stable with respect to compound degradation over a period of at least about 1 month.

In other embodiments, an additional surfactant (co-surfactant) and/or buffering agent is combined with one or more of the pharmaceutically acceptable vehicles previously described herein so that the surfactant and/or buffering agent maintains the product at an optimal pH for stability. Suitable co-surfactants include, but are not limited to: a) natural and synthetic lipophilic agents, e.g., phospholipids, cholesterol, and cholesterol fatty acid esters and derivatives thereof; b) nonionic surfactants, which include for example, polyoxyethylene fatty alcohol esters, sorbitan fatty acid esters (Spans), polyoxyethylene sorbitan fatty acid esters (e.g., polyoxyethylene (20) sorbitan monooleate (Tween 80), polyoxyethylene (20) sorbitan monostearate (Tween 60), polyoxyethylene (20) sorbitan monolaurate (Tween 20) and other Tweens, sorbitan esters, glycerol esters, e.g., Myrj and glycerol triacetate (triacetin), polyethylene glycols, cetyl alcohol, cetostearyl alcohol, stearyl alcohol, polysorbate 80, poloxamers, poloxamines, polyoxyethylene castor oil derivatives (e.g., Cremophor® RH40, Cremphor A25, Cremphor A20, Cremophor® EL) and other Cremophors, sulfosuccinates, alkyl sulphates (SLS); PEG glyceryl fatty acid esters such as PEG-8 glyceryl caprylate/caprate (Labrasol), PEG-4 glyceryl caprylate/caprate (Labrafac Hydro WL 1219), PEG-32 glyceryl laurate (Gelucire 444/14), PEG-6 glyceryl mono oleate (Labrafil M 1944 CS), PEG-6 glyceryl linoleate (Labrafil M 2125 CS); propylene glycol mono- and di-fatty acid esters, such as propylene glycol laurate, propylene glycol caprylate/caprate; Brij® 700, ascorbyl-6-palmitate, stearylamine, sodium lauryl sulfate, polyoxethyleneglycerol triiricinoleate, and any combinations or mixtures thereof; c) anionic surfactants include, but are not limited to, calcium carboxymethylcellulose, sodium carboxymethylcellulose, sodium sulfosuccinate, dioctyl, sodium alginate, alkyl polyoxyethylene sulfates, sodium lauryl sulfate, triethanolamine stearate, potassium laurate, bile salts, and any combinations or mixtures thereof; and d) cationic surfactants such as cetyltrimethylammonium bromide, and lauryldimethylbenzyl-ammonium chloride.

In a further embodiment, when one or more co-surfactants are utilized in the auris-acceptable compositions of the present disclosure, they are combined, e.g., with a pharmaceutically acceptable vehicle and is present in the final composition, e.g., in an amount ranging from about 0.1% to about 20%, from about 0.5% to about 10%.

In one embodiment, the surfactant has an HLB value of 0 to 20. In additional embodiments, the surfactant has an HLB value of 0 to 3, of 4 to 6, of 7 to 9, of 8 to 18, of 13 to 15, of 10 to 18.

In one embodiment, diluents are also used to stabilize the CNS modulating agent or other pharmaceutical compounds because they provide a more stable environment. Salts dissolved in buffered solutions (that also can provide pH control or maintenance) are utilized as diluents, including, but not limited to a phosphate buffered saline solution. In other embodiments, the gel composition is isotonic with the endolymph or the perilymph: depending on the portion of the cochlea that the CNS modulating agent composition is targeted. Isotonic compositions are provided by the addition of a tonicity agent. Suitable tonicity agents include, but are not limited to any pharmaceutically acceptable sugar, salt or any combinations or mixtures thereof, such as, but not limited to dextrose and sodium chloride. In further embodiments, the tonicity agents are present in an amount from about 100 mOsm/kg to about 500 mOsm/kg. In some embodiments, the tonicity agent is present in an amount from about 200 mOsm/ kg to about 400 mOsm/kg, from about 280 mOsm/kg to about 320 mOsm/kg. The amount of tonicity agents will depend on the target structure of the pharmaceutical composition, as described herein.

Useful tonicity compositions also include one or more salts in an amount required to bring osmolality of the composition into an acceptable range for the perilymph or the endolymph. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some embodiments, the auris-acceptable gel compositions disclosed herein alternatively or additionally contains preservatives to prevent microbial growth. Suitable auris-acceptable preservatives for use in the enhanced viscosity compositions described herein include, but are not limited to benzoic acid, boric acid, p-hydroxybenzoates, alcohols, quarternary compounds, stabilized chlorine dioxide, mercurials, such as merfen and thiomersal, mixtures of the foregoing and the like.

In a further embodiment, the preservative is, by way of example only, an antimicrobial agent, within the auris-acceptable compositions presented herein. In one embodiment, the composition includes a preservative such as by way of example only, methyl paraben, sodium bisulfite, sodium thiosulfate, ascorbate, chorobutanol, thimerosal, parabens, benzyl alcohol, phenylethanol and others. In another embodiment, the methyl paraben is at a concentration of about 0.05% to about 1.0%, about 0.1% to about 0.2%. In a further embodiment, the gel is prepared by mixing water, methylparaben, hydroxyethylcellulose and sodium citrate. In a further embodiment, the gel is prepared by mixing water, methylparaben, hydroxyethylcellulose and sodium acetate. In a further embodiment, the mixture is sterilized by autoclaving at 120° C. for about 20 minutes, and tested for pH, methylparaben concentration and viscosity before mixing with the appropriate amount of the CNS modulating agent disclosed herein.

Suitable auris-acceptable water soluble preservatives that are employed in the drug delivery vehicle include sodium bisulfite, sodium thiosulfate, ascorbate, chorobutanol, thimerosal, parabens, benzyl alcohol, Butylated hydroxytoluene (BHT), phenylethanol and others. These agents are present, generally, in amounts of about 0.001% to about 5% by weight and, preferably, in the amount of about 0.01 to about 2% by weight. In some embodiments, auris-compatible compositions described herein are free of preservatives.

Round Window Membrane Penetration Enhancers

In another embodiment, the composition further comprises one or more round window membrane penetration enhancers. Penetration across the round window membrane is enhanced by the presence of round window membrane penetration enhancers. Round window membrane penetration enhancers are chemical entities that facilitate transport of coadministered substances across the round window membrane. Round window membrane penetration enhancers are grouped according to chemical structure. Surfactants, both ionic and non-ionic, such as sodium lauryl sulfate, sodium laurate, polyoxyethylene-20-cetyl ether, laureth-9, sodium dodecylsulfate, dioctyl sodium sulfosuccinate, polyoxyethylene-9-lauryl ether (PLE), Tween® 80, nonylphenoxypolyethylene (NP-POE), polysorbates and the like, function as round window membrane penetration enhancers. Bile salts (such as sodium glycocholate, sodium deoxycholate, sodium taurocholate, sodium taurodihydrofusidate, sodium glycodihydrofusidate and the like), fatty acids and derivatives (such as oleic acid, caprylic acid, mono- and di-glycerides, lauric acids, acylcholines, caprylic acids, acylcarnitines, sodium caprates and the like), chelating agents (such as EDTA, citric acid, salicylates and the like), sulfoxides (such as dimethyl sulfoxide (DMSO), decylmethyl sulfoxide and the like), and alcohols (such as ethanol, isopropanol, glycerol, propanediol and the like) also function as round window membrane penetration enhancers.

In some embodiments, the auris acceptable penetration enhancer is a surfactant comprising an alkyl-glycoside wherein the alkyl glycoside is tetradecyl-β-D-maltoside. In some embodiments, the auris acceptable penetration enhancer is a surfactant comprising an alkyl-glycoside wherein the alkyl glycoside is dodecyl-maltoside. In certain instances, the penetration enhancing agent is a hyaluronidase. In certain instances, a hyaluronidase is a human or bovine hyaluronidase. In some instances, a hyaluronidase is a human hyaluronidase (e.g., hyaluronidase found in human sperm, PH20 (Halozyme), Hyelenex® (Baxter International, Inc.)). In some instances, a hyaluronidase is a bovine hyaluronidase (e.g., bovine testicular hyaluronidase, Amphadase® (Amphastar Pharmaceuticals), Hydase® (PrimaPharm, Inc). In some instances, a hyaluronidase is an ovine hyaluronidase, Vitrase® (ISTA Pharmaceuticals). In certain instances, a hyaluronidase described herein is a recombinant hyaluronidase. In some instances, a hyaluronidase described herein is a humanized recombinant hyaluronidase. In some instances, a hyaluronidase described herein is a pegylated hyaluronidase (e.g., PEGPH20 (Halozyme)). In addition, the peptide-like penetration enhancers described in U.S. Pat. Nos. 7,151,191, 6,221,367 and 5,714,167, herein incorporated by references for such disclosure, are contemplated as an additional embodiment. These penetration enhancers are amino-acid and peptide derivatives and enable drug absorption by passive transcellular diffusion without affecting the integrity of membranes or intercellular tight junctions.

Round Window Membrane Permeable Liposomes

Liposomes or lipid particles may also be employed to encapsulate the CNS modulating agent compositions or compositions. Phospholipids that are gently dispersed in an aqueous medium form multilayer vesicles with areas of entrapped aqueous media separating the lipid layers. Sonication, or turbulent agitation, of these multilayer vesicles results in the formation of single layer vesicles, commonly referred to as liposomes, with sizes of about 10-1000 nm. These liposomes have many advantages as CNS modulating agents or other pharmaceutical agent carriers. They are biologically inert, biodegradable, non-toxic and non-antigenic. Liposomes are formed in various sizes and with varying compositions and surface properties. Additionally, they are able to entrap a wide variety of agents and release the agent at the site of liposome collapse.

Suitable phospholipids for use in auris-acceptable liposomes here are, for example, phosphatidyl cholines, ethanolamines and serines, sphingomyelins, cardiolipins, plasmalogens, phosphatidic acids and cerebrosides, in particular those that are soluble together with the CNS modulating agents herein in non-toxic, pharmaceutically acceptable organic solvents. Preferred phospholipids are, for example, phosphatidyl choline, phosphatidyl ethanolmine, phosphatidyl serine, phosphatidyl inositol, lysophosphatidyl choline, phosphatidyl glycerol and the like, and mixtures thereof especially lecithin, e.g. soya lecithin. The amount of phospholipid used in the present composition range from about 10 to about 30%, preferably from about 15 to about 25% and in particular is about 20%.

Lipophilic additives may be employed advantageously to modify selectively the characteristics of the liposomes.

Examples of such additives include by way of example only, stearylamine, phosphatidic acid, tocopherol, cholesterol, cholesterol hemisuccinate and lanolin extracts. The amount of lipophilic additive used range from 0.5 to 8%, preferably from 1.5 to 4% and in particular is about 2%. Generally, the ratio of the amount of lipophilic additive to the amount of phospholipid ranges from about 1:8 to about 1:12 and in particular is about 1:10. Said phospholipid, lipophilic additive and the CNS modulating agent and other pharmaceutical compounds are employed in conjunction with a non-toxic, pharmaceutically acceptable organic solvent system that dissolve said ingredients. Said solvent system not only must dissolve the CNS modulating agent completely, but it also has to allow the composition of stable single bilayered liposomes. The solvent system comprises dimethylisosorbide and tetraglycol (glycofurol, tetrahydrofurfuryl alcohol polyethylene glycol ether) in an amount of about 8 to about 30%. In said solvent system, the ratio of the amount of dimethylisosorbide to the amount of tetraglycol range from about 2:1 to about 1:3, in particular from about 1:1 to about 1:2.5 and preferably is about 1:2. The amount of tetraglycol in the final composition thus vary from 5 to 20%, in particular from 5 to 15% and preferably is approximately 10%. The amount of dimethylisosorbide in the final composition thus range from 3 to 10%, in particular from 3 to 7% and preferably is approximately 5%.

The term "organic component" as used hereinafter refers to mixtures comprising said phospholipid, lipophilic additives and organic solvents. The CNS modulating agent may be dissolved in the organic component, or other means to maintain full activity of the agent. The amount of a CNS modulating agent in the final composition may range from 0.1 to 5.0%. In addition, other ingredients such as anti-oxidants may be added to the organic component. Examples include tocopherol, butylated hydroxyanisole, butylated hydroxytoluene, ascorbyl palmitate, ascorbyl oleate and the like.

Liposomal compositions are alternatively prepared, for CNS modulating agents or other pharmaceutical agents that are moderately heat-resistant, by (a) heating the phospholipid and the organic solvent system to about 60-80° C. in a vessel, dissolving the active ingredient, then adding any additional formulating agents, and stirring the mixture until complete dissolution is obtained; (b) heating the aqueous solution to 90-95° C. in a second vessel and dissolving the preservatives therein, allowing the mixture to cool and then adding the remainder of the auxiliary formulating agents and the remainder of the water, and stirring the mixture until complete dissolution is obtained; thus preparing the aqueous component; (c) transferring the organic phase directly into the aqueous component, while homogenizing the combination with a high performance mixing apparatus, for example, a high-shear mixer; and (d) adding a viscosity enhancing agent to the resulting mixture while further homogenizing. The aqueous component is optionally placed in a suitable vessel that is equipped with a homogenizer and homogenization is effected by creating turbulence during the injection of the organic component. Any mixing means or homogenizer that exerts high shear forces on the mixture may be employed. Generally, a mixer capable of speeds from about 1,500 to 20,000 rpm, in particular from about 3,000 to about 6,000 rpm may be employed. Suitable viscosity enhancing agents for use in process step (d) are for example, xanthan gum, hydroxypropyl cellulose, hydroxypropyl methylcellulose or mixtures thereof. The amount of viscosity enhancing agent depends on the nature and the concentration of the other ingredients and in general ranges from about 0.5 to 2.0%, or approximately 1.5%. In order to prevent degradation of the materials used during the preparation of the liposomal composition, it is advantageous to purge all solutions with an inert gas such as nitrogen or argon, and to conduct all steps under an inert atmosphere. Liposomes prepared by the above described method usually contain most of the active ingredient bound in the lipid bilayer and separation of the liposomes from unencapsulated material is not required.

In other embodiments, the auris-acceptable compositions, including gel compositions and viscosity-enhanced compositions, further include excipients, other medicinal or pharmaceutical agents, carriers, adjuvants, such as preserving, stabilizing, wetting or emulsifying agents, solution promoters, salts, solubilizers, an antifoaming agent, an antioxidant, a dispersing agent, a wetting agent, a surfactant, and combinations thereof.

Suitable carriers for use in an auris-acceptable composition described herein include, but are not limited to, any pharmaceutically acceptable solvent compatible with the targeted auris structure's physiological environment. In other embodiments, the base is a combination of a pharmaceutically acceptable surfactant and solvent.

In some embodiments, other excipients include, sodium stearyl fumarate, diethanolamine cetyl sulfate, isostearate, polyethoxylated castor oil, nonoxyl 10, octoxynol 9, sodium lauryl sulfate, sorbitan esters (sorbitan monolaurate, sorbitan monooleate, sorbitan monopalmitate, sorbitan monostearate, sorbitan sesquioleate, sorbitan trioleate, sorbitan tristearate, sorbitan laurate, sorbitan oleate, sorbitan palmitate, sorbitan stearate, sorbitan dioleate, sorbitan sesqui-isostearate, sorbitan sesquistearate, sorbitan tri-isostearate), lecithin pharmaceutical acceptable salts thereof and combinations or mixtures thereof.

In other embodiments, the carrier is a polysorbate. Polysorbates are nonionic surfactants of sorbitan esters. Polysorbates useful in the present disclosure include, but are not limited to polysorbate 20, polysorbate 40, polysorbate 60, polysorbate 80 (Tween 80) and any combinations or mixtures thereof. In further embodiments, polysorbate 80 is utilized as the pharmaceutically acceptable carrier.

In one embodiment, water-soluble glycerin-based auris-acceptable enhanced viscosity compositions utilized in the preparation of pharmaceutical delivery vehicles comprise at least one CNS modulating agent containing at least about 0.1% of the water-soluble glycerin compound or more. In some embodiments, the percentage of a CNS modulating agent is varied between about 1% and about 95%, between about 5% and about 80%, between about 10% and about 60% or more of the weight or volume of the total pharmaceutical composition. In some embodiments, the amount of the compound(s) in each therapeutically useful CNS modulating agent composition is prepared in such a way that a suitable dosage will be obtained in any given unit dose of the compound. Factors such as solubility, bioavailability, biological half-life, route of administration, product shelf life, as well as other pharmacological considerations are contemplated herein.

If desired, the auris-acceptable pharmaceutical gels also contain co-solvents, preservatives, cosolvents, ionic strength and osmolality adjustors and other excipients in addition to buffering agents. Suitable auris-acceptable water soluble buffering agents are alkali or alkaline earth metal carbonates, phosphates, bicarbonates, citrates, borates, acetates, succinates and the like, such as sodium phosphate, citrate, borate, acetate, bicarbonate, carbonate and tromethamine (TRIS). These agents are present in amounts sufficient to maintain the pH of the system at 7.4±0.2 and preferably, 7.4. As such, the buffering agent is as much as 5% on a weight basis of the total composition.

Cosolvents are used to enhance CNS modulating agent solubility, however, some CNS modulating agents or other pharmaceutical compounds are insoluble. These are often suspended in the polymer vehicle with the aid of suitable suspending or viscosity enhancing agents.

Moreover, some pharmaceutical excipients, diluents or carriers are potentially ototoxic. For example, benzalkonium chloride, a common preservative, is ototoxic and therefore potentially harmful if introduced into the vestibular or cochlear structures. In formulating a controlled-release CNS modulating agent composition, it is advised to avoid or combine the appropriate excipients, diluents or carriers to lessen or eliminate potential ototoxic components from the composition, or to decrease the amount of such excipients, diluents or carriers. Optionally, a controlled-release CNS modulating agent composition includes otoprotective agents, such as antioxidants, alpha lipoic acid, calcium, fosfomycin or iron chelators, to counteract potential ototoxic effects that may arise from the use of specific therapeutic agents or excipients, diluents or carriers.

The following are examples of therapeutically acceptable otic compositions:

of drug in that high levels of drug are found in the serum and correspondingly lower levels are found at the inner ear.

Intratympanic injection of therapeutic agents is the technique of injecting a therapeutic agent behind the tympanic membrane into the middle and/or inner ear. In one embodiment, the compositions described herein are administered directly onto the round window membrane via transtympanic injection. In another embodiment, the CNS modulating agent auris-acceptable compositions described herein are administered onto the round window membrane via a non-transtympanic approach to the inner ear. In additional embodiments, the composition described herein is administered onto the round window membrane via a surgical approach to the round window membrane comprising modification of the crista fenestrae cochleae.

In one embodiment the delivery system is a syringe and needle apparatus that is capable of piercing the tympanic membrane and directly accessing the round window membrane or crista fenestrae cochleae of the auris interna. In some embodiments, the needle on the syringe is wider than a 18 gauge needle. In another embodiment, the needle gauge is from 18 gauge to 31 gauge. In a further embodiment, the needle gauge is from 25 gauge to 30 gauge. Depending upon the thickness or viscosity of the CNS modulating agent compositions or compositions, the gauge level of the syringe or

| Example Composition | Example Characteristics |
|---|---|
| Chitosan glycerophosphate (CGP) | tunable degradation of matrix in vitro<br>tunable TACE inhibitor release in vitro: e.g., ~50% of drug released after 24 hrs<br>biodegradable<br>compatible with drug delivery to the inner ear<br>suitable for macromolecules and hydrophobic drugs |
| PEG-PLGA-PEG triblock polymers | tunable high stability: e.g., maintains mechanical integrity >1 month in vitro<br>tunable fast release of hydrophilic drugs: e.g., ~50% of drug released after 24 hrs, and remainder released over ~5 days<br>tunable slow release of hydrophobic drugs: e.g., ~80% released after 8 weeks<br>biodegradable<br>subcutaneous injection of solution: e.g., gel forms within seconds and is intact after 1 month |
| PEO-PPO-PEO triblock copolymers (e.g., Pluronic or Poloxameres) (e.g., F127) | Tunable sol-gel transition temperature: e.g., decreases with increasing F127 concentration |
| Chitosan glycerophosphate with drug-loaded liposomes | CGP composition tolerates liposomes: e.g., up to 15 uM/ml liposomes.<br>liposomes tunably reduce drug release time (e.g., up to 2 weeks in vitro).<br>increase in liposome diameter optionally reduces drug release kinetics (e.g., liposome size between 100 and 300 nm)<br>release parameters are controlled by changing composition of liposomes |

The compositions disclosed herein alternatively encompass an otoprotectant agent in addition to the at least one active agent and/or excipients, including but not limited to such agents as antioxidants, alpha lipoic acid, calcium, fosfomycin or iron chelators, to counteract potential ototoxic effects that may arise from the use of specific therapeutic agents or excipients, diluents or carriers.

Modes of Treatment

Dosing Methods and Schedules

Drugs delivered to the inner ear have been administered systemically via oral, intravenous or intramuscular routes. However, systemic administration for pathologies local to the inner ear increases the likelihood of systemic toxicities and adverse side effects and creates a non-productive distribution hypodermic needle may be varied accordingly. In another embodiment, the internal diameter of the needle can be increased by reducing the wall thickness of the needle (commonly referred as thin wall or extra thin wall needles) to reduce the possibly of needle clogging while maintaining an adequate needle gauge.

In another embodiment, the needle is a hypodermic needle used for instant delivery of the gel composition. The hypodermic needle may be a single use needle or a disposable needle. In some embodiments, a syringe may be used for delivery of the pharmaceutically acceptable gel-based CNS modulating agent-containing compositions as disclosed herein wherein the syringe has a press-fit (Luer) or twist-on (Luer-lock) fitting. In one embodiment, the syringe is a hypodermic syringe. In another embodiment, the syringe is made of plastic or glass. In yet another embodiment, the hypodermic syringe is a single use syringe. In a further embodiment, the glass syringe is capable of being sterilized. In yet a further embodiment, the sterilization occurs through an autoclave. In another embodiment, the syringe comprises a cylindrical syringe body wherein the gel composition is stored before use. In other embodiments, the syringe comprises a cylindrical syringe body wherein the CNS modulating agent pharmaceutically acceptable gel-based compositions as disclosed herein is stored before use that conveniently allows for mixing with a suitable pharmaceutically acceptable buffer. In other embodiments, the syringe may contain other excipients, stabilizers, suspending agents, diluents or a combination thereof to stabilize or otherwise stably store the CNS modulating agent or other pharmaceutical compounds contained therein.

In some embodiments, the syringe comprises a cylindrical syringe body wherein the body is compartmentalized in that each compartment is able to store at least one component of the auris-acceptable CNS modulating agent gel composition. In a further embodiment, the syringe having a compartmentalized body allows for mixing of the components prior to injection into the auris media or auris interna. In other embodiments, the delivery system comprises multiple syringes, each syringe of the multiple syringes contains at least one component of the gel composition such that each component is pre-mixed prior to injection or is mixed subsequent to injection. In a further embodiment, the syringes disclosed herein comprise at least one reservoir wherein the at least one reservoir comprises a CNS modulating agent, or a pharmaceutically acceptable buffer, or a viscosity enhancing agent, such as a gelling agent or a combination thereof. Commercially available injection devices are optionally employed in their simplest form as ready-to-use plastic syringes with a syringe barrel, needle assembly with a needle, plunger with a plunger rod, and holding flange, to perform an intratympanic injection.

In some embodiments, the delivery device is an apparatus designed for administration of therapeutic agents to the middle and/or inner ear. By way of example only: GYRUS Medical Gmbh offers micro-otoscopes for visualization of and drug delivery to the round window niche; Arenberg has described a medical treatment device to deliver fluids to inner ear structures in U.S. Pat. Nos. 5,421,818; 5,474,529; and 5,476,446, each of that is incorporated by reference herein for such disclosure. U.S. patent application Ser. No. 08/874,208, which is incorporated herein by reference for such disclosure, describes a surgical method for implanting a fluid transfer conduit to deliver therapeutic agents to the inner ear. U.S. Patent Application Publication 2007/0167918, which is incorporated herein by reference for such disclosure, further describes a combined otic aspirator and medication dispenser for intratympanic fluid sampling and medicament application.

The compositions described herein, and modes of administration thereof, are also applicable to methods of direct instillation or perfusion of the inner ear compartments. Thus, the compositions described herein are useful in surgical procedures including, by way of non-limiting examples, cochleostomy, labyrinthotomy, mastoidectomy, stapedectomy, endolymphatic sacculotomy or the like.

The auris-acceptable compositions or compositions containing the CNS modulating agent compound(s) described herein are administered for prophylactic and/or therapeutic treatments. In therapeutic applications, the CNS modulating agent compositions are administered to a patient already suffering from a disorder disclosed herein, in an amount sufficient to cure or at least partially arrest the symptoms of the disease, disorder or condition. Amounts effective for this use will depend on the severity and course of the disease, disorder or condition, previous therapy, the patient's health status and response to the drugs, and the judgment of the treating physician.

In the case wherein the patient's condition does not improve, upon the doctor's discretion the administration of the CNS modulating agent compounds may be administered chronically, which is, for an extended period of time, including throughout the duration of the patient's life in order to ameliorate or otherwise control or limit the symptoms of the patient's disease or condition.

In the case wherein the patient's status does improve, upon the doctor's discretion the administration of the CNS modulating agent compounds may be given continuously; alternatively, the dose of drug being administered may be temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday may be from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's otic conditions has occurred, a maintenance CNS modulating agent dose is administered if necessary. Subsequently, the dosage or the frequency of administration, or both, is optionally reduced, as a function of the symptoms, to a level at that the improved disease, disorder or condition is retained. In certain embodiments, patients require intermittent treatment on a long-term basis upon any recurrence of symptoms.

The amount of a CNS modulating agent that will correspond to such an amount will vary depending upon factors such as the particular compound, disease condition and its severity, according to the particular circumstances surrounding the case, including, e.g., the specific CNS modulating agent being administered, the route of administration, the condition being treated, the target area being treated, and the subject or host being treated. In general, however, doses employed for adult human treatment will typically be in the range of 0.02-50 mg per administration, preferably 1-15 mg per administration. The desired dose is presented in a single dose or as divided doses administered simultaneously (or over a short period of time) or at appropriate intervals.

In some embodiments, the initial administration is a particular CNS modulating agent and the subsequent administration a different composition or CNS modulating agent.

Implants of Exogenous Materials

In some embodiments, the pharmaceutical formulations, compositions and devices described herein are used in combination with (e.g., implantation, short-term use, long-term use, or removal of) the implantation of an exogenous material (e.g., a medical device or a plurality of cells (e.g., stem cells)). As used herein, the term "exogenous material" includes auris-interna or auris-media medical devices (e.g., hearing sparing devices, hearing improving devices, short electrodes, microprostheses or piston-like prostheses); needles; drug delivery devices, and cells (e.g., stem cells). In some instances, the implants of exogenous materials are used in conjunction with a patient experiencing hearing loss. In some instances, the hearing loss is present at birth. In some instances, the hearing loss is associated with conditions that develop or progress after birth (e.g., Merniere's disease) resulting in osteoneogenesis, nerve damage, obliteration of cochlear structures, or combinations thereof.

In some instances, the exogenous material is a plurality of cells. In some instances, the exogenous material is a plurality of stem cells.

In some instances, the exogenous material is an electronic device. In some embodiments, the electronic device has an external portion placed behind the ear, and a second portion that is surgically placed under the skin that helps provide a sense of sound to a person who is profoundly deaf or severely hard-of-hearing. By way of example only, such medical device implants bypass damaged portions of the ear and directly stimulate the auditory nerve. In some instances cochlear implants are used in single sided deafness. In some instances cochlear implants are used for deafness in both ears.

In some embodiments, administration of an active agent described herein in combination with the implantation of an exogenous material (e.g., a medical device implant or a stem cell transplant) delays or prevents damage of auris structures, e.g., irritation, cell death osteoneogeneis and/or further neuronal degeneration, caused by installation of an external device and/or a plurality cells (e.g., stem cells) in the ear. In some embodiments, administration of a composition or device described herein in combination with an implant allows for a more effective restoration of hearing loss compared to an implant alone.

In some embodiments, administration of an active agent described herein reduces damage to auris structures caused by underlying conditions allowing for successful implantation. In some embodiments, administration of an active agent described herein, in conjunction surgery and/or with the implantation of an exogenous material reduces or prevents negative side-effects (e.g., cell death).

In some embodiments, administration of an active agent described herein in conjunction with the implantation of an exogenous material has a trophic effect (i.e., promotes healthy growth of cells and healing of tissue in the area of an implant or transplant). In some embodiments, a trophic effect is desirable during otic surgery or during intratympanic injection procedures. In some embodiments, a trophic effect is desirable after installation of a medical device or after a cell (e.g., stem cell) transplant. In some of such embodiments, the compositions or devices described herein are administered via direct cochlear injection, through a chochleostomy or via deposition on the round window In some embodiments, administration of an active agent described herein reduces inflammation and/or infections associated with otic surgery, or implantation of an exogenous material (e.g., a medical device or a plurality of cells (e.g., stem cells)). In some instances, perfusion of a surgical area with a formulation described herein reduces or eliminates post-surgical and/or post-implantation complications (e.g., inflammation, hair cell damage, neuronal degeneration, osteoneogenesis or the like). In some instances, perfusion of a surgical area with a formulation described herein reduces post-surgery or post-implantation recuperation time.

In one aspect, the formulations described herein, and modes of administration thereof, are applicable to methods of direct perfusion of the inner ear compartments. Thus, the formulations described herein are useful in combination with surgical procedures including, by way of non-limiting examples, cochleostomy, labyrinthotomy, mastoidectomy, stapedectomy, stapedotomy, endolymphatic sacculotomy or the like. In some embodiments, the inner ear compartments are perfused with a formulation described herein prior to otic surgery, during otic surgery, after otic surgery, or a combination thereof. In some of such embodiments, the formulations described herein are substantially free of extended release components (e.g., gelling components such as polyoxyethylene-polyoxypropylene copolymers). In some of such embodiments, the formulations described herein contain less than 5% of the extended release components (e.g., gelling components such as polyoxyethylene-polyoxypropylene triblock copolymers) by weight of the formulation. In some of such embodiments, the formulations described herein contain less than 2% of the extended release components (e.g., gelling components such as polyoxyethylene-polyoxypropylene triblock copolymers) by weight of the formulation. In some of such embodiments, the formulations described herein contain less than 1% of the extended release components (e.g., gelling components such as polyoxyethylene-polyoxypropylene triblock copolymers) by weight of the formulation. In some of such embodiments, a composition described herein that is used for perfusion of a surgical area contains substantially no gelling component.

Pharmacokinetics of Controlled-Release Compositions

In one embodiment, the compositions disclosed herein additionally provides an immediate release of a CNS modulating agent from the composition, or within 1 minute, or within 5 minutes, or within 10 minutes, or within 15 minutes, or within 30 minutes, or within 60 minutes or within 90 minutes. In other embodiments, a therapeutically effective amount of at least one CNS modulating agent is released from the composition immediately, or within 1 minute, or within 5 minutes, or within 10 minutes, or within 15 minutes, or within 30 minutes, or within 60 minutes or within 90 minutes. In certain embodiments the composition comprises an auris-pharmaceutically acceptable gel composition providing immediate release of at least one CNS modulating agent. Additional embodiments of the composition may also include an agent that enhances the viscosity of the compositions included herein.

In other or further embodiments, the composition provides an extended release composition of at least one CNS modulating agent. In certain embodiments, diffusion of at least one CNS modulating agent from the composition occurs for a time period exceeding 5 minutes, or 15 minutes, or 30 minutes, or 1 hour, or 4 hours, or 6 hours, or 12 hours, or 18 hours, or 1 day, or 2 days, or 3 days, or 4 days, or 5 days, or 6 days, or 7 days, or 10 days, or 12 days, or 14 days, or 18 days, or 21 days, or 25 days, or 30 days, or 45 days, or 2 months or 3 months or 4 months or 5 months or 6 months or 9 months or 1 year. In other embodiments, a therapeutically effective amount of at least one CNS modulating agent is released from the composition for a time period exceeding 5 minutes, or 15 minutes, or 30 minutes, or 1 hour, or 4 hours, or 6 hours, or 12 hours, or 18 hours, or 1 day, or 2 days, or 3 days, or 4 days, or 5 days, or 6 days, or 7 days, or 10 days, or 12 days, or 14 days, or 18 days, or 21 days, or days, or 30 days, or 45 days, or 2 months or 3 months or 4 months or 5 months or 6 months or 9 months or 1 year.

In other embodiments, the composition provides both an immediate release and an extended release composition of a CNS modulating agent. In yet other embodiments, the composition contains a 0.25:1 ratio, or a 0.5:1 ratio, or a 1:1 ratio, or a 1:2 ratio, or a 1:3, or a 1:4 ratio, or a 1:5 ratio, or a 1:7 ratio, or a 1:10 ratio, or a 1:15 ratio, or a 1:20 ratio of immediate release and extended release compositions. In a further embodiment the composition provides an immediate release of a first CNS modulating agent and an extended release of a second CNS modulating agent or other therapeutic agent. In yet other embodiments, the composition provides an immediate release and extended release composition of at least one CNS modulating agent, and at least one therapeutic agent. In some embodiments, the composition provides a 0.25:1 ratio, or a 0.5:1 ratio, or a 1:1 ratio, or a 1:2 ratio, or a 1:3, or a 1:4 ratio, or a 1:5 ratio, or a 1:7 ratio, or a 1:10 ratio, or a 1:15 ratio, or a 1:20 ratio of immediate release and extended release compositions of a first CNS modulating agent and second therapeutic agent, respectively.

In a specific embodiment the composition provides a therapeutically effective amount of at least one CNS modulating agent at the site of disease with essentially no systemic exposure. In an additional embodiment the composition provides a therapeutically effective amount of at least one CNS modulating agent at the site of disease with essentially no detectable systemic exposure. In other embodiments, the composition provides a therapeutically effective amount of at least one CNS modulating agent at the site of disease with little or no detectable systemic exposure.

The combination of immediate release, delayed release and/or extended release CNS modulating agent compositions or compositions may be combined with other pharmaceutical agents, as well as the excipients, diluents, stabilizers, tonicity agents and other components disclosed herein. As such, depending upon the CNS modulating agent used, the thickness or viscosity desired, or the mode of delivery chosen, alternative aspects of the embodiments disclosed herein are combined with the immediate release, delayed release and/or extended release embodiments accordingly.

In certain embodiments, the pharmacokinetics of the CNS modulating agent compositions described herein are determined by injecting the composition on or near the round window membrane of a test animal (including by way of example, a guinea pig or a chinchilla). At a determined period of time (e.g., 6 hours, 12 hours, 1 day, 2 days, 3 days, 4 days, 5 days, 6 days, and 7 days for testing the pharmacokinetics of a composition over a 1 week period), the test animal is euthanized and a 5 mL sample of the perilymph fluid is tested. The inner ear removed and tested for the presence of the CNS modulating agent. As needed, the level of a CNS modulating agent is measured in other organs. In addition, the systemic level of the CNS modulating agent is measured by withdrawing a blood sample from the test animal. In order to determine whether the composition impedes hearing, the hearing of the test animal is optionally tested.

Alternatively, an inner ear is provided (as removed from a test animal) and the migration of the CNS modulating agent is measured. As yet another alternative, an in vitro model of a round window membrane is provided and the migration of the CNS modulating agent is measured.

The release of an active agent from any formulation, composition or device described herein is optionally tunable to the desired release characteristics. In some embodiments, a composition described herein is a solution that is substantially free of gelling components. In such instances, the composition provides essentially immediate release of an active agent. In some of such embodiments, the composition is useful in perfusion of otic structures, e.g., during surgery.

In some embodiments, a composition described herein is a solution that is substantially free of gelling components and comprises micronized otic agent. In some of such embodiments, the composition provides intermediate release of an active agent from about 2 day to about 4 days.

In some embodiments, a composition described herein comprises a gelling agent (e.g., poloxamer 407) and provides release of an active agent over a period of from about 1 day to about 3 days. In some embodiments, a composition described herein comprises a gelling agent (e.g., poloxamer 407) and provides release of an active agent over a period of from about 1 day to about 5 days. In some embodiments, a composition described herein comprises a gelling agent (e.g., poloxamer 407) and provides release of an active agent over a period of from about 2 days to about 7 days.

In some embodiments, a composition described herein comprises a gelling agent (e.g., poloxamer 407) in combination with micronized otic agent and provides extended sustained release. In some embodiments, a composition described herein comprises (a) about 14-17% of a gelling agent (e.g., poloxamer 407) and (b) a micronized otic agent; and provides extended sustained release over a period of from about 1 week to about 3 weeks. In some embodiments, a composition described herein comprises (a) about 16% of a gelling agent (e.g., poloxamer 407) and (b) a micronized otic agent; and provides extended sustained release over a period of from about 3 weeks. In some embodiments, a composition described herein comprises (a) about 18-21% of a gelling agent (e.g., poloxamer 407) and (b) a micronized otic agent; and provides extended sustained release over a period of from about 3 weeks to about 6 weeks. In some embodiments, a composition described herein comprises (a) about 20% of a gelling agent (e.g., poloxamer 407) and (b) a micronized otic agent; and provides extended sustained release over a period of from about 6 weeks. In some embodiments, the amount of gelling agent in a composition, and the particle size of an otic agent are tunable to the desired release profile of an otic agent from the composition.

In specific embodiments, compositions comprising micronized otic agents provide extended release over a longer period of time compared to compositions comprising non-micronized otic agents. In specific embodiments, selection of an appropriate particle size of the active agent (e.g., micronized active agent) in combination with the amount of gelling agent in the composition provides tunable extended release characteristics that allow for release of an active agent over a period of hours, days, weeks or months.

Kits/Articles of Manufacture

The disclosure also provides kits for preventing, treating or ameliorating the symptoms of a disease or disorder in a mammal. Such kits generally will comprise one or more of the CNS modulating agent controlled-release compositions or devices disclosed herein, and instructions for using the kit. The disclosure also contemplates the use of one or more of the CNS modulating agent controlled-release compositions, in the manufacture of medicaments for treating, abating, reducing, or ameliorating the symptoms of a disease, dysfunction, or disorder in a mammal, such as a human that has, is suspected of having, or at risk for developing an inner ear disorder.

In some embodiments, kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. In other embodiments, the containers are formed from a variety of materials such as glass or plastic.

The articles of manufacture provided herein contain packaging materials. Packaging materials for use in packaging pharmaceutical products are also presented herein. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected composition and intended mode of administration and treatment. A wide array of a CNS modulating agent compositions provided herein are contemplated as are a variety of treatments for any disease, disorder, or condition that would benefit by controlled-release administration of a CNS modulating agent to the inner ear.

In some embodiments, a kit includes one or more additional containers, each with one or more of various materials (such as reagents, optionally in concentrated form, and/or devices) desirable from a commercial and user standpoint for use of a composition described herein. Non-limiting examples of such materials include, but not limited to, buffers, diluents, filters, needles, syringes; carrier, package, container, vial and/or tube labels listing contents and/or instructions for use and package inserts with instructions for use. A set of instructions is optionally included. In a further embodiment, a label is on or associated with the container. In yet a further embodiment, a label is on a container when letters, numbers or other characters forming the label are attached, molded or etched into the container itself; a label is associated with a container when it is present within a receptacle or carrier that also holds the container, e.g., as a package insert. In other embodiments a label is used to indicate that the contents are to be used for a specific therapeutic application. In yet another embodiment, a label also indicates directions for use of the contents, such as in the methods described herein.

In certain embodiments, the pharmaceutical compositions are presented in a pack or dispenser device that contains one or more unit dosage forms containing a compound provided herein. In another embodiment, the pack for example contains metal or plastic foil, such as a blister pack. In a further embodiment, the pack or dispenser device is accompanied by instructions for administration. In yet a further embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. In another embodiment, such notice, for example, is the labeling approved by the U.S. Food and Drug Administration for prescription drugs, or the approved product insert. In yet another embodiment, compositions containing a compound provided herein formulated in a compatible pharmaceutical carrier are also prepared, placed in an appropriate container, and labeled for treatment of an indicated condition.

EXAMPLES

Example 1

Preparation of a Thermoreversible Gel Diazepam Composition

| Ingredient | Quantity (mg/g of composition) |
|---|---|
| Diazepam | 25.0 |
| methylparaben | 2.5 |
| Hypromellose | 25.0 |
| Poloxamer 407 | 450. |
| TRIS HCl buffer (0.1M) | 1997.5 |

Diazepam is supplied in 5 mg/ml pre-filled glass syringes.
A 10-g batch of gel composition containing 1.0% of diazepam is prepared by first suspending Poloxamer 407 (BASF Corp.) in TRIS HCl buffer (0.1M). The Poloxamer 407 and TRIS are mixed under agitation overnight at 4° C. to ensure complete dissolution of the Poloxamer 407 in the TRIS. The hypromellose, methylparaben and additional TRIS HCl buffer (0.1 M) is added. The composition is stirred until dissolution is observed. Diazepam is added and the composition is mixed until a homogenous gel is produced. The mixture is maintained below room temperature until use.

Example 2

Preparation of a Mucoadhesive, Thermoreversible Gel Diazepam Composition

| Ingredient | Quantity (mg/g of composition) |
|---|---|
| Diazepam | 25.0 |
| methylparaben | 2.5 |
| Hypromellose | 25.0 |
| Carbopol 934P | 5.0 |
| Poloxamer 407 | 450.0 |
| TRIS HCl buffer (0.1M) | 1992.5 |

A 10-g batch of mucoadhesive gel composition containing 1.0% of diazepam is prepared by first suspending Poloxamer 407 (BASF Corp.) and Carbopol 934P in IRIS HCl buffer (0.1 M). The Poloxamer 407, Carbopol 934P and TRIS are mixed under agitation overnight at 4° C. to ensure complete dissolution of the Poloxamer 407 and Carbopol 934P in the TRIS. The hypromellose, methylparaben and additional IRIS HCl buffer (0.1 M) is added. The composition is stirred until dissolution is observed. Diazepam is added and the composition is mixed until a homogenous gel is produced. The mixture is maintained below room temperature until use.

Example 3

Preparation of a Hydrogel-Based Lidocaine Composition

| Ingredient | Quantity (mg/g of composition) |
|---|---|
| Lidocaine HCl | 30.0 |
| paraffin oil | 600 |
| trihydroxystearate | 30.0 |
| cetyl dimethicon copolyol | 90.0 |
| water | qs ad 1000 |
| phosphate buffer pH 7.4 | qs pH 7.4 |

The cream-type composition is first prepared by gently mixing Lidocaine HCl with water. Then, the oil base is prepared by mixing paraffin oil, trihydroxystearate and cetyl dimethicon copolyol at temperatures up to 60° C. The oil base is cooled to room temperature and the Lidocaine HCl solution is added. The two phases are mixed until a homogenous, monophasic hydrogel is formed.

Example 4

Preparation of a Gel Gabapentin Composition

| Ingredient | Quantity (mg/g of composition) |
|---|---|
| Gabapentin | 40.0 |
| chitosan | 20.0 |
| Glycerophosphate disodium | 80.0 |
| water | 840 |

A 5 ml solution of acetic acid is titrated to a pH of about 4.0. The chitosan is added to achieve a pH of about 5.5. The gabapentin is then dissolved in the chitosan solution. This solution is sterilized by filtration. A 5 ml aqueous solution of glycerophosphate disodium is also prepared and sterilized. The two solutions are mixed and within 2 h at 37° C., the desired gel is formed.

Example 5

Application of an Enhanced Viscosity Diazepam Composition onto the Round Window Membrane A composition according to Example 2 is prepared and loaded into 5 ml siliconized glass syringes attached to a 15-gauge luer lock disposable needle. Lidocaine is topically applied to the tympanic membrane, and a small incision made to allow visualization into the middle ear cavity. The needle tip is guided into place over the round window membrane, and the CNS Modulating composition applied directly onto the round-window membrane.

Example 6

Effect of pH on Degradation Products for Autoclaved 17% Poloxamer 407NF/2% Otic Agent in PBS Buffer A stock solution of a 17% poloxamer 407/2% otic agent is prepared by dissolving 351.4 mg of sodium chloride (Fisher Scientific), 302.1 mg of sodium phosphate dibasic anhydrous (Fisher Scientific), 122.1 mg of sodium phosphate monobasic anhydrous (Fisher Scientific) and an appropriate amount of an otic agent with 79.3 g of sterile filtered DI water. The solution is cooled down in a ice chilled water bath and then 17.05 g of poloxamer 407NF (SPECTRUM CHEMICALS) is sprinkled into the cold solution while mixing. The mixture is further mixed until the poloxamer is completely dissolved. The pH for this solution is measured.

17% Poloxamer 407/2% Otic Agent in PBS pH of 5.3.

Take an aliquot (approximately 30 mL) of the above solution and adjust the pH to 5.3 by the addition of 1 M HCl.

17% Poloxamer 407/2% Otic Agent in PBS pH of 8.0.

Take an aliquot (approximately 30 mL) of the above stock solution and adjust the pH to 8.0 by the addition of 1 M NaOH.

A PBS buffer (pH 7.3) is prepared by dissolving 805.5 mg of sodium chloride (Fisher Scientific), 606 mg of sodium phosphate dibasic anhydrous (Fisher Scientific), 247 mg of sodium phosphate monobasic anhydrous (Fisher Scientific), then QS to 200 g with sterile filtered DI water.

A 2% solution of an otic agent in PBS pH 7.3 is prepared by dissolving an appropriate amount of the otic agent in the PBS buffer and QS to 10 g with PBS buffer.

One mL samples are individually placed in 3 mL screw cap glass vials (with rubber lining) and closed tightly. The vials are placed in a Market Forge-sterilmatic autoclave (settings, slow liquids) and sterilized at 250° F. for 15 minutes. After the autoclave the samples are left to cool down to room temperature and then placed in refrigerator. The samples are homogenized by mixing the vials while cold.

Appearance (e.g., discoloration and/or precipitation) is observed and recorded. HPLC analysis is performed using an Agilent 1200 equipped with a Luna C18(2) 3 μm, 100 Å, 250×4.6 mm column) using a 30-80 acetonitrile gradient (1-10 min) of (water-acetonitrile mixture containing 0.05% TFA), for a total run of 15 minutes. Samples are diluted by taking 30 μL of sample and dissolved with 1.5 mL of a 1:1 acetonitrile water mixture. Purity of the otic agent in the autoclaved samples is recorded.

In general the composition should not have any individual impurity (e.g., degradation product of otic agent) of more than 2% and more preferably not more than one percent. In addition, the composition should not precipitate during storage or change in color after manufacturing and storage.

Compositions comprising alprazolam, clonazepam, diazepam, or micronized diazepam, prepared according to the procedure in Example 6, are tested using the above procedure to determine the effect of pH on degradation during the autoclaving step.

Example 7

Effect of Autoclaving on The Release Profile and Viscosity of a 17% Poloxamer 407NF/2% Otic Agent in PBS An aliquot of the sample from example 6 (autoclaved and not autoclaved) is evaluated for release profile and viscosity measurement to evaluate the impact of heat sterilization on the properties of the gel.

Dissolution is performed at 37° C. in snapwells (6.5 mm diameter polycarbonate membrane with a pore size of 0.4 μm). 0.2 mL of gel is placed into snapwell and left to harden, then 0.5 mL is placed into reservoir and shaken using a Labline orbit shaker at 70 rpm. Samples are taken every hour (0.1 mL withdrawn and replace with warm buffer). Samples are analyzed for poloxamer concentration by UV at 624 nm using the cobalt thiocyanate method, against an external calibration standard curve. In brief, 20 μL of the sample is mixed with 1980 μL of a 15 mM cobalt thiocyanate solution and absorbance measured at 625 nm, using a Evolution 160 UV/V is spectrophotometer (Thermo Scientific).

The released otic agent is fitted to the Korsmeyer-Peppas equation $$\frac{Q}{Q_\alpha} = kt^n + b$$

where Q is the amount of otic agent released at time t, $Q_\alpha$ is the overall released amount of otic agent, k is a release constant of the nth order, n is a dimensionless number related to the dissolution mechanism and b is the axis intercept, characterizing the initial burst release mechanism wherein n=1 characterizes an erosion controlled mechanism. The mean dissolution time (MDT) is the sum of different periods of time the drug molecules stay in the matrix before release, divided by the total number of molecules and is calculated by:

$$MDT = \frac{nk^{\frac{-1}{n}}}{n+1}$$

Viscosity measurements are performed using a Brookfield viscometer RVDV-II+P with a CPE-51 spindle rotated at 0.08 rpm (shear rate of 0.31 s$^{-1}$), equipped with a water jacketed temperature control unit (temperature ramped from 15-34° C. at 1.6° C./min). Tgel is defined as the inflection point of the curve where the increase in viscosity occurs due to the sol-gel transition.

Compositions comprising alprazolam, clonazepam, diazepam, or micronized diazepam prepared according to the procedure in Example 6, are tested using the procedure described above to determine Tgel.

Example 8

Effect of Addition of a Secondary Polymer on the Degradation Products and Viscosity Of a Composition Containing 2% Otic Agent and 17% Poloxamer 407NF after Heat Sterilization (Autoclaving)

Solution A.

A solution of pH 7.0 comprising sodium carboxymethylcellulose (CMC) in PBS buffer is prepared by dissolving 178.35 mg of sodium chloride (Fisher Scientific), 300.5 mg of sodium phosphate dibasic anhydrous (Fisher Scientific), 126.6 mg of sodium phosphate monobasic anhydrous (Fisher Scientific) dissolved with 78.4 of sterile filtered DI water, then 1 g of Blanose 7M65 CMC (Hercules, viscosity of 5450 cP@2%) is sprinkled into the buffer solution and heated to aid dissolution, and the solution is then cooled down.

A solution of pH 7.0 comprising 17% poloxamer 407NF/1% CMC/2% otic agent in PBS buffer is made by cooling down 8.1 g of solution A in a ice chilled water bath and then adding an appropriate amount of an otic agent followed by mixing. 1.74 g of poloxamer 407NF (Spectrum Chemicals) is sprinkled into the cold solution while mixing. The mixture is further mixed until all the poloxamer is completely dissolved.

Two mL of the above sample is placed in a 3 mL screw cap glass vial (with rubber lining) and closed tightly. The vial is placed in a Market Forge-sterilmatic autoclave (settings, slow liquids) and sterilized at 250° F. for 25 minutes. After autoclaving the sample is left to cool down to room temperature and then placed in refrigerator. The sample is homogenized by mixing while the vials are cold.

Precipitation or discoloration are observed after autoclaving. HPLC analysis is performed using an Agilent 1200 equipped with a Luna C18(2) 3 µm, 100 Å, 250×4.6 mm column) using a 30-80 acetonitrile gradient (1-10 min) of (water-acetonitrile mixture containing 0.05% TFA), for a total run of 15 minutes. Samples are diluted by taking 30 µL of sample and dissolving with 1.5 mL of a 1:1 acetonitrile water mixture. Purity of the otic agent in the autoclaved samples is recorded.

Viscosity measurements are performed using a Brookfield viscometer RVDV-II+P with a CPE-51 spindle rotated at 0.08 rpm (shear rate of 0.31 s$^{-1}$), equipped with a water jacketed temperature control unit (temperature ramped from 15-34° C. at 1.6° C./min). Tgel is defined as the inflection point of the curve where the increase in viscosity occurs due to the sol-gel transition.

Dissolution is performed at 37° C. for the non-autoclaved sample in snapwells (6.5 mm diameter polycarbonate membrane with a pore size of 0.4 µm), 0.2 mL of gel is placed into snapwell and left to harden, then 0.5 mL is placed into reservoir and shaken using a Labline orbit shaker at 70 rpm. Samples are taken every hour (0.1 mL withdrawn and replaced with warm buffer). Samples are analyzed for otic agent concentration by UV at 245 nm, against an external calibration standard curve.

Compositions comprising alprazolam, clonazepam, diazepam, or micronized diazepam are tested using the above procedure to determine the effect addition of a secondary polymer on the degradation products and viscosity of a composition containing 2% otic agent and 17% poloxamer 407NF after heat sterilization (autoclaving).

Example 9

Effect of Buffer Type on the Degradation Products for Compositions Containing Poloxamer 407NF after Heat Sterilization (Autoclaving)

A TRIS buffer is made by dissolving 377.8 mg of sodium chloride (Fisher Scientific), and 602.9 mg of Tromethamine (Sigma Chemical Co.) then QS to 100 g with sterile filtered DI water, pH is adjusted to 7.4 with 1M HCl.

Stock Solution Containing 25% Poloxamer 407 Solution in TRIS Buffer:

Weigh 45 g of TRIS buffer, chill in an ice chilled bath then sprinkle into the buffer, while mixing, 15 g of poloxamer 407 NF (Spectrum Chemicals). The mixture is further mixed until all the poloxamer is completely dissolved.

A series of compositions is prepared with the above stock solution. An appropriate amount of otic agent (or salt or prodrug thereof) and/or otic agent as micronized/coated/liposomal particles (or salt or prodrug thereof) is used for all experiments.

Stock Solution (pH 7.3) Containing 25% Poloxamer 407 Solution in PBS Buffer:

PBS buffer is prepared by dissolving 704 mg of sodium chloride (Fisher Scientific), 601.2 mg of sodium phosphate dibasic anhydrous (Fisher Scientific), 242.7 mg of sodium phosphate monobasic anhydrous (Fisher Scientific) with 140.4 g of sterile filtered DI water. The solution is cooled down in an ice chilled water bath and then 50 g of poloxamer 407NF (SPECTRUM CHEMICALS) is sprinkled into the cold solution while mixing. The mixture is further mixed until the poloxamer is completely dissolved.

A series of compositions is prepared with the above stock solution. An appropriate amount of otic agent (or salt or prodrug thereof) and/or otic agent as micronized/coated/liposomal particles (or salt or prodrug thereof) is used for all experiments.

Tables 2 and 3 list samples prepared using the procedures described above. An appropriate amount of otic agent is added to each sample to provide a final concentration of 2% otic agent in the sample.

TABLE 2

Preparation of samples containing TRIS buffer

| Sample | pH | 25% Stock Solution (g) | TRIS Buffer (g) |
| --- | --- | --- | --- |
| 20% P407/2 otic agent/TRIS | 7.45 | 8.01 | 1.82 |
| 18% P407/2 otic agent/TRIS | 7.45 | 7.22 | 2.61 |
| 16% P407/2 otic agent/TRIS | 7.45 | 6.47 | 3.42 |
| 18% P4072 otic agent/TRIS | 7.4 | 7.18 | 2.64 |
| 4% otic agent/TRIS | 7.5 | — | 9.7 |
| 2% otic agent/TRIS | 7.43 | — | 5 |
| 1% otic agent/TRIS | 7.35 | — | 5 |
| 2% otic agent/TRIS (suspension) | 7.4 | — | 4.9 |

TABLE 3

Preparation of samples containing PBS buffer (pH of 7.3)

| Sample | 25% Stock Solution in PBS (g) | PBS Buffer (g) |
| --- | --- | --- |
| 20% P407/2 otic agent/PBS | 8.03 | 1.82 |
| 18% P407/2 otic agent/PBS | 7.1 | 2.63 |
| 16% P407/2 otic agent/PBS | 6.45 | 3.44 |
| 18% P407/2 otic agent/PBS | — | 2.63 |
| 2% otic agent/PBS | — | 4.9 |

One mL samples are individually placed in 3 mL screw cap glass vials (with rubber lining) and closed tightly. The vials are placed in a Market Forge-sterilmatic autoclave (setting, slow liquids) and sterilized at 250° F. for 25 minutes. After the autoclaving the samples are left to cool down to room temperature. The vials are placed in the refrigerator and mixed while cold to homogenize the samples.

HPLC analysis is performed using an Agilent 1200 equipped with a Luna C18(2) 3 μM, 100 Å, 250×4.6 mm column) using a 30-80 acetonitrile gradient (1-10 min) of (water-acetonitrile mixture containing 0.05% TFA), for a total run of 15 minutes. Samples are diluted by taking 30 μL of sample and dissolving with 1.5 mL of a 1:1 acetonitrile water mixture. Purity of the otic agent in the autoclaved samples is recorded. The stability of compositions in TRIS and PBS buffers is compared.

Viscosity measurements are performed using a Brookfield viscometer RVDV-II+P with a CPE-51 spindle rotated at 0.08 rpm (shear rate of $0.31\ s^{-1}$), equipped with a water jacketed temperature control unit (temperature ramped from 15-34° C. at 1.6° C./min). Tgel is defined as the inflection point of the curve where the increase in viscosity occurs due to the sol-gel transition. Only compositions that show no change after autoclaving are analyzed.

Compositions comprising. Compositions comprising alprazolam, clonazepam, diazepam, or micronized diazepam are tested using the above procedure to determine the effect addition of a secondary polymer on the degradation products and viscosity of a composition containing 2% otic agent and 17% poloxamer 407NF after heat sterilization (autoclaving). Stability of compositions containing micronized otic agent is compared to non-micronized otic agent composition counterparts.

Example 10

Pulsed Release Otic Compositions

Diazepam is used to prepare a pulsed release otic agent composition using the procedures described herein. A 17% poloxamer solution is prepared by dissolving 351.4 mg of sodium chloride (Fisher Scientific), 302.1 mg of sodium phosphate dibasic anhydrous (Fisher Scientific), 122.1 mg of sodium phosphate monobasic anhydrous (Fisher Scientific) and an appropriate amount of an otic agent with 79.3 g of sterile filtered DI water. The solution is cooled down in a ice chilled water bath and then 17.05 g of poloxamer 407NF (SPECTRUM CHEMICALS) is sprinkled into the cold solution while mixing. The mixture is further mixed until the poloxamer is completely dissolved. The pH for this solution is measured. 20% of the delivered dose of diazepam is solubilized in the 17% poloxamer solution with the aid of beta-cyclodextrins. The remaining 80% of the otic agent is then added to the mixture and the final composition is prepared using any procedure described herein.

Pulsed release compositions comprising Compositions comprising alprazolam, clonazepam, diazepam, or micronized diazepam prepared according to the procedures and examples described herein, are tested using procedures described herein to determine pulse release profiles.

Example 11

Preparation of a 17% Poloxamer 407/2% Otic Agent/78 Ppm Evans Blue in PBS

A Stock solution of Evans Blue (5.9 mg/mL) in PBS buffer is prepared by dissolving 5.9 mg of Evans Blue (Sigma Chemical Co) with 1 mL of PBS buffer. PBS buffer is prepared by dissolving 704 mg of sodium chloride (Fisher Scientific), 601.2 mg of sodium phosphate dibasic anhydrous (Fisher Scientific), 242.7 mg of sodium phosphate monobasic anhydrous (Fisher Scientific) with 140.4 g of sterile filtered DI water.

A Stock solution containing 25% Poloxamer 407 solution in PBS buffer (as in Example 9) is used in this study. An appropriate amount of an otic agent is added to the 25% Poloxamer 407 solution stock solution to prepare compositions comprising 2% of an otic agent (Table 4).

TABLE 4

Preparation of poloxamer 407 samples containing Evans Blue

| Sample ID | 25% P407 in PBS (g) | PBS Buffer (g) | Evans Blue Solution (μL) |
| --- | --- | --- | --- |
| 17% P407/2 otic agent/EB | 13.6 | 6 | 265 |
| 20% P407/2 otic agent/EB | 16.019 | 3.62 | 265 |
| 25% P407/2 otic agent/EB | 19.63 | — | 265 |

Compositions comprising alprazolam, clonazepam, diazepam, or micronized diazepam are prepared according to the procedures in Example 12 and are sterile filtered through 0.22 μm PVDF syringe filters (Millipore corporation), and autoclaved.

The above compositions are dosed to guinea pigs in the middle ear by procedures described herein and the ability of compositions to gel upon contact and the location of the gel is identified after dosing and at 24 hours after dosing.

Example 12

Terminal Sterilization of Poloxamer 407 Compositions with and without a Visualization Dye 17% Poloxamer 407/2% Otic Agent/in Phosphate Buffer, pH 7.3:

Dissolve 709 mg of sodium chloride (Fisher Scientific), 742 mg of sodium phosphate dibasic dehydrate USP (Fisher Scientific), 251.1 mg of sodium phosphate monobasic monohydrate USP (Fisher Scientific) and an appropriate amount of an otic agent with 158.1 g of sterile filtered DI water. The solution is cooled down in an ice chilled water bath and then 34.13 g of poloxamer 407NF (Spectrum chemicals) is sprinkled into the cold solution while mixing. The mixture is further mixed until the poloxamer is completely dissolved.

17% Poloxamer 407/2% Otic Agent/59 Ppm Evans Blue in Phosphate Buffer:

Take two mL of the 17% poloxamer 407/2% otic agent/in phosphate buffer solution and add 2 mL of a 5.9 mg/mL Evans blue (Sigma-Aldrich chemical Co) solution in PBS buffer.

25% Poloxamer 407/2% Otic Agent/in Phosphate Buffer:

Dissolve 330.5 mg of sodium chloride (Fisher Scientific), 334.5 mg of sodium phosphate dibasic dehydrate USP (Fisher Scientific), 125.9 mg of sodium phosphate monobasic monohydrate USP (Fisher Scientific) and an appropriate amount of an otic agent with 70.5 g of sterile filtered DI water.

The solution is cooled down in an ice chilled water bath and then 25.1 g of poloxamer 407NF (Spectrum chemicals) is sprinkled into the cold solution while mixing. The mixture is further mixed until the poloxamer is completely dissolved.

25% Poloxamer 407/2% Otic Agent/59 Ppm Evans Blue in Phosphate Buffer:

Take two mL of the 25% poloxamer 407/2% otic agent/in phosphate buffer solution and add 2 mL of a 5.9 mg/mL Evans blue (Sigma-Aldrich chemical Co) solution in PBS buffer.

Place 2 mL of composition into a 2 mL glass vial (Wheaton serum glass vial) and seal with 13 mm butyl str (kimble stoppers) and crimp with a 13 mm aluminum seal. The vials are placed in a Market Forge-sterilmatic autoclave (settings, slow liquids) and sterilized at 250° F. for 25 minutes. After the autoclaving the samples are left to cool down to room temperature and then placed in refrigeration. The vials are placed in the refrigerator and mixed while cold to homogenize the samples. Sample discoloration or precipitation after autoclaving is recorded.

HPLC analysis is performed using an Agilent 1200 equipped with a Luna C18(2) 3 µm, 100 Å, 250×4.6 mm column) using a 30-95 methanol:acetate buffer pH 4 gradient (1-6 min), then isocratic for 11 minutes, for a total run of 22 minutes. Samples are diluted by taking 30 µL of sample and dissolved with 0.97 mL of water. The main peaks are recorded in the table below. Purity before autoclaving is always greater than 99% using this method.

Viscosity measurements are performed using a Brookfield viscometer RVDV-II+P with a CPE-51 spindle rotated at 0.08 rpm (shear rate of 0.31 s$^{-1}$), equipped with a water jacketed temperature control unit (temperature ramped from 15-34° C. at 1.6° C./min). Tgel is defined as the inflection point of the curve where the increase in viscosity occurs due to the sol-gel transition.

Compositions comprising alprazolam, clonazepam, diazepam, or micronized diazepam prepared according to the procedure in Example 11, are tested using the above procedures to determine stability of the compositions.

Example 13

In Vitro Comparison of Release Profile

Dissolution is performed at 37° C. in snapwells (6.5 mm diameter polycarbonate membrane with a pore size of 0.4 µm), 0.2 mL of a gel composition described herein is placed into snapwell and left to harden, then 0.5 mL buffer is placed into reservoir and shaken using a Labline orbit shaker at 70 rpm. Samples are taken every hour (0.1 mL withdrawn and replace with warm buffer). Samples are analyzed for otic agent concentration by UV at 245 nm against an external calibration standard curve. Pluronic concentration is analyzed at 624 nm using the cobalt thiocyanate method. Relative rank-order of mean dissolution time (MDT) as a function of % P407 is determined. A linear relationship between the compositions mean dissolution time (MDT) and the P407 concentration indicates that the otic agent is released due to the erosion of the polymer gel (poloxamer) and not via diffusion. A non-linear relationship indicates release of otic agent via a combination of diffusion and/or polymer gel degradation.

Alternatively, samples are analyzed using the method described by Li Xin-Yu paper [Acta Pharmaceutica Sinica 2008, 43(2):208-203] and Rank-order of mean dissolution time (MDT) as a function of % P407 is determined.

Compositions comprising alprazolam, clonazepam, diazepam, or micronized diazepam prepared according to the procedures described herein, are tested using the above procedure to determine the release profile of the otic agents.

Example 14

In Vitro Comparison of Gelation Temperature

The effect of Poloxamer 188 and an otic agent on the gelation temperature and viscosity of Poloxamer 407 compositions is evaluated with the purpose of manipulating the gelation temperature.

A 25% Poloxamer 407 stock solution in PBS buffer (as in Example 9) and a PBS solution (as in Example 11) are used. Poloxamer 188NF from BASF is used. An appropriate amount of otic agent is added to the solutions described in Table 5 to provide a 2% composition of the otic agent.

TABLE 5

Preparation of samples containing poloxamer 407/poloxamer 188

| Sample | 25% P407 Stock Solution (g) | Poloxamer 188 (mg) | PBS Buffer (g) |
|---|---|---|---|
| 16% P407/10% P188 | 3.207 | 501 | 1.3036 |
| 17% P407/10% P188 | 3.4089 | 500 | 1.1056 |
| 18% P407/10% P188 | 3.6156 | 502 | 0.9072 |
| 19% P407/10% P188 | 3.8183 | 500 | 0.7050 |
| 20% P407/10% P188 | 4.008 | 501 | 0.5032 |
| 20% P407/5% P188 | 4.01 | 256 | 0.770 |

Mean dissolution time, viscosity and gel temperature of the above compositions are measured using procedures described herein.

An equation is fitted to the data obtained and can be utilized to estimate the gelation temperature of F127/F68 mixtures (for 17-20% F127 and 0-10% F68).

$$T_{gel} = -1.8(\%F127) + 1.3(\%F68) + 53$$

An equation is fitted to the data obtained and can be utilized to estimate the Mean Dissolution Time (hr) based on the gelation temperature of F127/F68 mixtures (for 17-25% F127 and 0-10% F68), using results obtained in example 13 and 15.

$$MDT=-0.2(T_{gel})+8$$

Compositions comprising alprazolam, clonazepam, diazepam, or micronized diazepam are prepared by addition of an appropriate amount of otic agents to the solutions described in Table 5. The gel temperature of the compositions is determined using the procedure described above.

Example 15

Determination of Temperature Range for Sterile Filtration

The viscosity at low temperatures is measured to help guide the temperature range at that the sterile filtration needs to occur to reduce the possibility of clogging.

Viscosity measurements are performed using a Brookfield viscometer RVDV-II+P with a CPE-40 spindle rotated at 1, 5 and 10 rpm (shear rate of 7.5, 37.5 and 75 s$^{-1}$), equipped with a water jacketed temperature control unit (temperature ramped from 10-25° C. at 1.6° C./min).

The Tgel of a 17% Pluronic P407 is determined as a function of increasing concentration of otic agent. The increase in Tgel for a 17% pluronic composition is estimated by:

$$\Delta T_{gel}=0.93[\% \text{ otic agent}]$$

Compositions comprising alprazolam, clonazepam, diazepam, or micronized diazepam prepared according to procedures described herein, are tested using the above procedure to determine the temperature range for sterile filtration. The effect of addition of increased amounts of otic agent on the Tgel, and the apparent viscosity of the compositions is recorded.

Example 16

Determination of Manufacturing Conditions

TABLE 6

Viscosity of potential compositions at manufacturing/filtration conditions.

| Sample | Apparent Viscosity$^a$ (cP) | | Temperature @ |
| --- | --- | --- | --- |
| | 5° C. below Tgel | 20° C. | 100 cP |
| Placebo | 52 cP @ 17° C. | 120 cP | 19° C. |
| 17% P407/2% otic agent | 90 cP @ 18° C. | 147 cP | 18.5° C. |
| 17% P407/6% otic agent | 142 cP @ 22° C. | 105 cP | 19.7° C. |

$^a$Viscosity measured at a shear rate of 37.5 s$^{-1}$

An 8 liter batch of a 17% P407 placebo is manufactured to evaluate the manufacturing/filtration conditions. The placebo is manufactured by placing 6.4 liters of DI water in a 3 gallon SS pressure vessel, and left to cool down in the refrigerator overnight. The following morning the tank was taken out (water temperature 5° C., RT 18° C.) and 48 g of sodium chloride, 29.6 g of sodium phosphate dibasic dehydrate and 10 g of sodium phosphate monobasic monohydrate is added and dissolved with an overhead mixer (IKA RW20@1720 rpm). Half hour later, once the buffer is dissolved (solution temperature 8° C., RT 18° C.), 1.36 kg of poloxamer 407 NF (spectrum chemicals) is slowly sprinkled into the buffer solution in a 15 minute interval (solution temperature 12° C., RT 18° C.), then speed is increased to 2430 rpm. After an additional one hour mixing, mixing speed is reduced to 1062 rpm (complete dissolution).

The temperature of the room is maintained below 25° C. to retain the temperature of the solution at below 19° C. The temperature of the solution is maintained at below 19° C. up to 3 hours of the initiation of the manufacturing, without the need to chill/cool the container.

Three different Sartoscale (Sartorius Stedim) filters with a surface area of 17.3 cm$^2$ are evaluated at 20 psi and 14° C. of solution 1) Sartopore 2, 0.2 μm 5445307HS-FF (PES), flow rate of 16 mL/min
2) Sartobran P, 0.2 μm 5235307HS-FF (cellulose ester), flow rate of 12 mL/min
3) Sartopore 2 XLI, 0.2 μm 5445307IS-FF (PES), flow rate of 15 mL/min Sartopore 2 filter 5441307H4-SS is used, filtration is carried out at the solution temperature using a 0.45, 0.2 μm Sartopore 2 150 sterile capsule (Sartorius Stedim) with a surface area of 0.015 m$^2$ at a pressure of 16 psi. Flow rate is measured at approximately 100 mL/min at 16 psi, with no change in flow rate while the temperature is maintained in the 6.5-14° C. range Decreasing pressure and increasing temperature of the solution causes a decrease in flow rate due to an increase in the viscosity of the solution. Discoloration of the solution is monitored during the process.

TABLE 7

Predicted filtration time for a 17% poloxamer 407 placebo at a solution temperature range of 6.5-14° C. using Sartopore 2, 0.2 μm filters at a pressure of 16 psi of pressure.

| Filter | Size (m$^2$) | Estimated flow rate (mL/min) | Time to filter 8 L (estimated) |
| --- | --- | --- | --- |
| Sartopore 2, size 4 | 0.015 | 100 mL/min | 80 min |
| Sartopore 2, size 7 | 0.05 | 330 mL/min | 24 min |
| Sartopore 2, size 8 | 0.1 | 670 mL/min | 12 min |

Viscosity, Tgel and UV/V is absorption is check before filtration evaluation. Pluronic UV/V is spectra are obtained by a Evolution 160 UV/V is (Thermo Scientific). A peak in the range of 250-300 nm is attributed to BHT stabilizer present in the raw material (poloxamer). Table 8 lists physicochemical properties of the above solutions before and after filtration.

TABLE 8

Physicochemical properties of 17% poloxamer 407 placebo solution before and after filtration

| Sample | Tgel (° C.) | Viscosity$^a$ @ 19° C. (cP) | Absorbance @ 274 nm |
| --- | --- | --- | --- |
| Before filtration | 22 | 100 | 0.3181 |
| After filtration | 22 | 100 | 0.3081 |

$^a$Viscosity measured at a shear rate of 37.5 s$^{-1}$

The above process is applicable for manufacture of 17% P407 compositions, and includes temperature analysis of the room conditions. Preferably, a maximum temperature of 19° C. reduces cost of cooling the container during manufacturing. In some instances, a jacketed container is used to further control the temperature of the solution to ease manufacturing concerns.

Example 17

In Vitro Release of Otic Agent from an Autoclaved Micronized Sample

17% poloxamer 407/1.5% otic agent in TRIS buffer: 250.8 mg of sodium chloride (Fisher Scientific), and 302.4 mg of Tromethamine (Sigma Chemical Co.) is dissolved in 39.3 g of sterile filtered DI water, pH is adjusted to 7.4 with 1M HCl. 4.9 g of the above solution is used and an appropriate amount of micronized otic agent is suspended and dispersed well. 2 mL of the composition is transferred into a 2 mL glass vial (Wheaton serum glass vial) and sealed with 13 mm butyl styrene (kimble stoppers) and crimped with a 13 mm aluminum seal. The vial is placed in a Market Forge-sterilmatic autoclave (settings, slow liquids) and sterilized at 250° F. for 25 minutes. After the autoclaving the sample is left to cool down to room temperature. The vial is placed in the refrigerator and mixed while cold to homogenize the sample. Sample discoloration or precipitation after autoclaving is recorded.

Dissolution is performed at 37° C. in snapwells (6.5 mm diameter polycarbonate membrane with a pore size of 0.4 μm), 0.2 mL of gel is placed into snapwell and left to harden, then 0.5 mL PBS buffer is placed into reservoir and shaken using a Labline orbit shaker at 70 rpm. Samples are taken every hour [0.1 mL withdrawn and replaced with warm PBS buffer containing 2% PEG-40 hydrogenated castor oil (BASF) to enhance otic agent solubility]. Samples are analyzed for otic agent concentration by UV at 245 nm against an external calibration standard curve. The release rate is compared to other compositions disclosed herein. MDT time is calculated for each sample.

Solubilization of otic agent in the 17% poloxamer system is evaluated by measuring the concentration of the otic agent in the supernatant after centrifuging samples at 15,000 rpm for 10 minutes using an eppendorf centrifuge 5424. Otic agent concentration in the supernatant is measured by UV at 245 nm against an external calibration standard curve.

Compositions comprising alprazolam, clonazepam, diazepam, or micronized diazepam prepared according to the procedures described herein, are tested using the above procedures to determine release rate of the otic agent from each composition.

Example 18

Release Rate or MDT and Viscosity of Composition Containing Sodium Carboxymethyl Cellulose 17% Poloxamer 407/2% Otic Agent/1% CMC (Hercules Blanose 7M):

A sodium carboxymethylcellulose (CMC) solution (pH 7.0) in PBS buffer is prepared by dissolving 205.6 mg of sodium chloride (Fisher Scientific), 372.1 mg of sodium phosphate dibasic dihydrate (Fisher Scientific), 106.2 mg of sodium phosphate monobasic monohydrate (Fisher Scientific) in 78.1 g of sterile filtered DI water. 1 g of Blanose 7M CMC (Hercules, viscosity of 533 cP@2%) is sprinkled into the buffer solution and heated to ease solution, solution is then cooled down and 17.08 g poloxamer 407NF (Spectrum Chemicals) is sprinkled into the cold solution while mixing. A composition comprising 17% poloxamer 407NF/1% CMC/2% otic agent in PBS buffer is made adding/dissolving an appropriate amount of otic agent to 9.8 g of the above solution, and mixing until all the otic agent is completely dissolved.

17% Poloxamer 407/2% Otic Agent/0.5% CMC (Blanose 7M65):

A sodium carboxymethylcellulose (CMC) solution (pH 7.2) in PBS buffer is prepared by dissolving 257 mg of sodium chloride (Fisher Scientific), 375 mg of sodium phosphate dibasic dihydrate (Fisher Scientific), 108 mg of sodium phosphate monobasic monohydrate (Fisher Scientific) in 78.7 g of sterile filtered DI water. 0.502 g of Blanose 7M65 CMC (Hercules, viscosity of 5450 cP@2%) is sprinkled into the buffer solution and heated to ease solution, solution is then cooled down and 17.06 g poloxamer 407NF (Spectrum Chemicals) is sprinkled into the cold solution while mixing. A 17% poloxamer 407NF/1% CMC/2% otic agent solution in PBS buffer is made adding/dissolving an appropriate amount of otic agent to 9.8 g of the above solution, and mixing until the otic agent is completely dissolved.

17% Poloxamer 407/2% Otic Agent/0.5% CMC (Blanose 7H9):

A sodium carboxymethylcellulose (CMC) solution (pH 7.3) in PBS buffer is prepared by dissolving 256.5 mg of sodium chloride (Fisher Scientific), 374 mg of sodium phosphate dibasic dihydrate (Fisher Scientific), 107 mg of sodium phosphate monobasic monohydrate (Fisher Scientific) in 78.6 g of sterile filtered DI water, then 0.502 g of Blanose 7H$_9$CMC (Hercules, viscosity of 5600 cP@1%) is sprinkled to the buffer solution and heated to ease solution, solution is then cooled down and 17.03 g poloxamer 407NF (Spectrum Chemicals) is sprinkled into the cold solution while mixing. A 17% poloxamer 407NF/1% CMC/2% otic agent solution in PBS buffer is made adding/dissolving an appropriate amount of otic agent to 9.8 of the above solution, and mixing until the otic agent is completely dissolved.

Viscosity measurements are performed using a Brookfield viscometer RVDV-II+P with a CPE-40 spindle rotated at 0.08 rpm (shear rate of 0.6 s$^{-1}$), equipped with a water jacketed temperature control unit (temperature ramped from 10-34° C. at 1.6° C./min). Tgel is defined as the inflection point of the curve where the increase in viscosity occurs due to the sol-gel transition.

Dissolution is performed at 37° C. in snapwells (6.5 mm diameter polycarbonate membrane with a pore size of 0.4 μm). 0.2 mL of gel is placed into snapwell and left to harden, then 0.5 mL PBS buffer is placed into reservoir and shaken using a Labline orbit shaker at 70 rpm. Samples are taken every hour, 0.1 mL withdrawn and replaced with warm PBS buffer. Samples are analyzed for otic agent concentration by UV at 245 nm against an external calibration standard curve. MDT time is calculated for each of the above compositions.

Compositions comprising alprazolam, clonazepam, diazepam, or micronized diazepam prepared according to procedures described above, are tested using the above procedures to determine relationship between release rate and/or mean dissolution time and viscosity of composition containing sodium carboxymethyl cellulose. Any correlation between the mean dissolution time (MDT) and the apparent viscosity (measured at 2° C. below the gelation temperature) is recorded.

Example 19

Application of an Enhanced Viscosity CNS Modulating Agent Composition onto the Round Window Membrane A composition according to Example 2 is prepared and loaded into 5 ml siliconized glass syringes attached to a 15-gauge luer lock disposable needle. Lidocaine is topically applied to the tympanic membrane, and a small incision made to allow visualization into the middle ear cavity. The needle tip is guided into place over the round window membrane, and the composition applied directly onto the round-window membrane.

Example 20

In Vivo Testing of Intratympanic Injection of a CNS Modulating Composition in a Guinea Pig A cohort of 21 guinea pigs (Charles River, females weighing 200-300 g) is intratympanically injected with 50 µL of different P407-DSP compositions described herein, containing 0 to 6% of an otic agent. The gel elimination time course for each composition is determined. A faster gel elimination time course of a composition indicates lower mean dissolution time (MDT). Thus the injection volume and the concentration of an CNS modulating agent in a composition are tested to determine optimal parameters for preclinical and clinical studies.

Example 22

In Vivo Extended Release Kinetics

A cohort of 21 guinea pigs (Charles River, females weighing 200-300 g) is intratympanically injected with 50 µL 17% Pluronic F-127 composition buffered at 280 mOsm/kg and containing 1.5% to 4.5% of a CNS modulating agent by weight of the composition. Animals are dosed on day 1. The release profile for the compositions is determined based on analysis of the perilymph.

Example 23

Evaluation of Diazepam in an Endolymphatic Hydrops Animal Model

Induction of Endolymphatic Hydrops
Female albino National Institutes of Health-Swiss mice (Harlan Sprague-Dawley, Inc., Indianapolis, Inc.) weighing 20 to 24 g are used. Artificial endolymph is injected into the cochlear duct.
Treatment
The endolymphatic mice and control mice are sorted into two groups (n=10 in each group). The CNS modulating composition of Example 5 containing diazepam is applied to the round window membrane of one group of animals. Control composition containing no diazepam is applied to the second group. The CNS modulating and control compositions are reapplied three days after the initial application. The animals are sacrificed after the seventh day of treatment.
Electrophysiologic Testing
The hearing threshold for the auditory brainstem response threshold (ABR) to click stimuli for each ear of each animal is initially measured and 1 week after the experimental procedure. The animals are placed in a single-walled acoustic booth (Industrial Acoustics Co, Bronx, N.Y., USA) on a heating pad. Subdermal electrodes (Astro-Med, Inc. Grass Instrument Division, West Warwick, R.I., USA) were inserted at the vertex (active electrode), the mastoid (reference), and the hind leg (ground). Click stimuli (0.1 millisecond) are computer generated and delivered to a Beyer DT 48, 200 Ohm speaker fitted with an ear speculum for placement in the external auditory meatus. The recorded ABR is amplified and digitized by a battery-operated preamplifier and input to a Tucker-Davis Technologies ABR recording system that provides computer control of the stimulus, recording, and averaging functions (Tucker Davis Technology, Gainesville, Fla., USA). Successively decreasing amplitude stimuli are presented in 5-dB steps to the animal, and the recorded stimulus-locked activity is averaged (n=512) and displayed. Threshold is defined as the stimulus level between the record with no visibly detectable response and a clearly identifiable response.

Example 24

Clinical Trial of Diazepam as a Treatment for Tinnitus

Dosage
The dosage of diazepam is 10 ng delivered in 10 µL of a thermoreversible gel. Release of diazepam is controlled-release and occurs over thirty (30) days.
Administration
The diazepam compositions are administered by intratympanic injection once every thirty days for 3 months.
Inclusion Criteria
Male and female subjects between the 18 and 64 years of age.
Subjects experiencing subjective tinnitus.
Duration of tinnitus is greater than 3 months.
No treatment of tinnitus within 4 weeks.
Study Design
Subjects are divided into three treatment groups. The first group is the safety sample. The second group is the intent-to-treat (ITT) sample. The third group is the valid for efficacy (VfE) group.
For each group, one half of subjects to be given diazepam and the remainder to be given placebo.
Statistical Methods
The primary efficacy analysis is based on the total score of the Tinnitus Questionnaire in the ITT sample. The statistical analysis is based on an analysis of covariance (ANCOVA) with baseline as covariant and the last observation carried forward value as dependent variable. Factor is "treatment." The homogeneity of regression slopes is tested. The analysis is repeated for the VfE sample.
Audiometric measurements (mode, frequency, loudness of the tinnitus, pure tone audiogram, speech audiogram) as well as quality of life are also analyzed via the aforementioned model. The appropriateness of the model is not tested. P values are exploratory and are not adjusted for multiplicity.

While preferred embodiments of the present invention have been shown and described herein, such embodiments are provided by way of example only. Various alternatives to the embodiments described herein are optionally employed in practicing the inventions. It is intended that the following claims define the scope of the invention and that methods and structures within the scope of these claims and their equivalents be covered thereby.

We claim:
1. A method of treating an otic disease or condition comprising administering an intratympanic composition on or near the round window membrane of an individual in need thereof, the intratympanic composition comprising:
between about 0.01% to about 20% by weight of a micronized Central Nervous System (CNS) modulator, or pharmaceutically acceptable salt thereof; and
a polyoxyethylene-polyoxypropylene copolymer in an amount sufficient to provide a gelation temperature between about 19° C. to about 42° C., and a gelation viscosity between about 15,000 cP and about 1,000,000 cP; and the intratympanic composition having an osmolarity of less than about 1000 mOsm/L;

wherein the intratympanic composition provides a sustained release of a therapeutically effective amount of the CNS modulator across the round window membrane into the cochlea for a period of at least 5 days after a single administration.

2. The method of claim 1, wherein the CNS modulator is a GABA receptor modulator or an antihistamine.

3. The method of claim 2, wherein the antihistamine is selected from meclizine, diphenhydramine, dimenhydrinate, loratadine, quetiapine, mepyramine, piperoxan, antazoline, carbinoxamine, doxylamine, clemastine, pheniramine, chlorphenamine, chlorpheniramine, dexchlorpheniramine, brompheniramine, triprolidine, cyclizine, chlorcyclizine, hydroxyzine, promethazine, alimemazine, trimeprazine, cyproheptadine, azatadine, ketotifen, oxatomide and betahistine.

4. The method of claim 2, wherein the GABA receptor modulator agonizes the activity of a GABA receptor.

5. The method of claim 2, wherein the GABA receptor modulator partially or fully inhibits the repolarization of a neuron.

6. The method of claim 2, wherein the GABA receptor modulator is selected from a benzodiazepine, a loop diuretic, or a GABA analogue.

7. The method of claim 2, wherein the GABA receptor modulator is selected from alprazolam, bromazepam, brotizolam, chlordiazepoxide, clonazepam, clorazepate, diazepam, estazolam, flunitrazepam, flurazepam, loprazolam, lorazepam, lormetazepam, idazolam, nimetazepam, nitrazepam, oxazepam, prazepam, temazepam, and triazolam or combinations thereof.

8. The method of claim 1, wherein the otic disease or condition is endolymphatic hydrops, kinetosis, labyrinthitis, mal de debarquement, Meniere's disease, Meniere's syndrome, Ramsay Hunt's syndrome (Herpes zoster infection), recurrent vestibulopathy, tinnitus, vertigo, microvascular compression syndrome, utricular dysfunction, vestibular neuronitis, benign paroxysmal positional vertigo, or combinations thereof.

9. The method of claim 1, wherein the otic disease or condition is tinnitus.

* * * * *